United States Patent
Meijboom et al.

(10) Patent No.: US 9,676,801 B2
(45) Date of Patent: Jun. 13, 2017

(54) USE OF SILVER(I) COMPLEXES AS ANTICANCER AGENTS

(71) Applicant: University of Johannesburg, Johassesburg (ZA)

(72) Inventors: Reinout Meijboom, Johannesburg (ZA); Marianne Jacqueline Cronje, Roodepoort (ZA)

(73) Assignee: UNIVERSITY OF JOHANNESBURG (ZA)

( * ) Notice: Subject to any disclaimer, the term of this patent is extended or adjusted under 35 U.S.C. 154(b) by 0 days.

(21) Appl. No.: 14/363,542

(22) PCT Filed: Dec. 6, 2012

(86) PCT No.: PCT/IB2012/057029
§ 371 (c)(1),
(2) Date: Jun. 6, 2014

(87) PCT Pub. No.: WO2013/084185
PCT Pub. Date: Jun. 13, 2013

(65) Prior Publication Data
US 2015/0037256 A1    Feb. 5, 2015

(30) Foreign Application Priority Data

Dec. 6, 2011 (ZA) .................................. 11/08944

(51) Int. Cl.
*A61K 9/00* (2006.01)
*C07F 9/54* (2006.01)
*A61K 33/38* (2006.01)
*A61K 31/66* (2006.01)
*A61K 49/00* (2006.01)

(52) U.S. Cl.
CPC ............ *C07F 9/5442* (2013.01); *A61K 31/66* (2013.01); *A61K 33/38* (2013.01); *A61K 49/0004* (2013.01)

(58) Field of Classification Search
CPC .................................................... C07F 9/5442
See application file for complete search history.

(56) References Cited

U.S. PATENT DOCUMENTS 4,857,549 A    8/1989  Hill et al.
2003/0207568 A1   11/2003  Byun et al.

FOREIGN PATENT DOCUMENTS

EP           0372313 A2    6/1990
WO      WO 2010/084315    7/2010
WO      WO 2011/089780    7/2011

OTHER PUBLICATIONS

Zartilas et al, Tetrameric 1:1 and monomeric 1:3 complexes of silver(I) halides with tri(p-tolyl)-phosphine: A structural and biological study, Inorganica Chimica Acta, 2009, 362, 1003-1010.*

(Continued)

*Primary Examiner* — Paul Dickinson
(74) *Attorney, Agent, or Firm* — Knobbe, Martens, Olson & Bear, LLP

(57) ABSTRACT

The present invention relates to the use of silver(I) monophosphine complexes as Active Pharmaceutical Ingredients (API's), including anticancer agents, for the treatment, diagnosis and/or prevention of cancer. The present invention also relates to pharmaceutical compositions containing such complexes and further extends to a method of treating or diagnosing a subject/patient suffering from cancer.

8 Claims, 35 Drawing Sheets

(56) References Cited

OTHER PUBLICATIONS

Barnard, P.J., et al., (2007) Targeting the mitochondrial cell death pathway with gold compounds. Co-ordination Chemistry Reviews 251 (13-14): 1889-1902.
Bayir, H., et al., (2008) Bench-to-bedside review: Mitochondrial injury, oxidative stress and apoptosis—there is nothing more practical than a good theory. Critical Care 12: 206.
Bello, B.O., et al. (2011). "Trends in lung cancer mortality in South Africa: 1995-2006." BMC Public Health 11(1): 209.
Berners-Price, S.J., et al., (1988) Structure and bonding, Phosphine and metal phosphine complexes: Relationship of chemistry to anticancer and other biological activity. Bioinorganic Chemistry, Springer Berlin/Heidelberg, 70 p. 27-102.
Berners-Price, S.J., et al., (1998) J. Chem. Soc., Dalton Transactions (11): 1743-1750.
Berners-Price, S.J., et al., (1999) Structural and solution chemistry of gold(I) and silver(I) complexes of bidentate pyridyl phosphines: selective antitumour agents: Coordination Chemistry Reviews 185-186, 823-836.
Bird-Lieberman, E.L., et al., (2009) Early diagnosis of oesophageal cancer. British Journal of Cancer 101: 1-6.
Bold, R.J., et al., (1997) Apoptosis, cancer and cancer therapy. Surgical Oncology 6: 133-142.
Brandys, M.C., et al., (2002), Polymeric complexes of silver(I) with diphosphine ligands: self-assembly of a puckered sheet network structure. Journal of the American Chemical Society 124(15): 3946-3950.
Bressac-de-Paillerets, B., et al., (2002) Genetic and environmental factors in cutaneous malignant melanoma. Biochimie 84(1): 67-74.
Cancer Facts & Figures; (2007). Atlanta, GA: American Cancer Society.
Chabner, B.A., et al., (2005) Chemotherapy and the war on cancer. Nature Reviews 5: 65-72.
Chowdhury, I., et al., (2008) Caspases—an update. Comparative Biochemistry and Physiology. Part B. 151: 10-27.
Cotter, T.G.; (2009) Apoptosis and cancer: the genesis of a research field. Nature Reviews Cancer 9(7): 501-597.
Danial, N.N., et al., (2004) Cell death: critical control points. Cell 116: 205-219.
Elmore, S.; (2007) Apoptosis: A Review of Programmed Cell Death: Toxicological Pathology 35: 495-516.
Enzinger, P.C., et al., (2003) Esophageal Cancer. National English Journal of Medicine, 349: 2241-52.
Ferlay, J. (2010). "Estimates of worldwide burden of cancer in 2008: GLOBOCAN 2008". International Journal of Cancer 127(12): 2893-2917.
Ferlay, J., et al., (2008) v1 .2, Cancer Incidence and Mortality Worldwide: IARC CancerBase No. 10 [Internet]. Lyon, France: International Agency for Research on Cancer; 2010. Available from: http://globocan.iarc.fr, accessed on Apr. 18, 2012. Cancer Incidence and Mortality Worldwide.
Festjens, N., et al., (2006) Necrosis, a well-orchestrated form of cell demise: Signalling cascades, important mediators and concomitant immune response. Biochimica et Biophysica Acta. 1757: 1371-1387.
Fischer, S.J., et al., (2008) Cisplatin and dimethyl sulfoxide react to form an adducted compound with reduced cytotoxicity and neurotoxicity: Neurotoxicology 29: 444-452.
Fischer, U., et al., (2005) Apoptosis-based therapies and drug targets. Cell Death and Differentiation 12: 942-961.
Garbe, C., et al., (2010) Diagnosis and treatment of melanoma: Europeanconsensus-based interdisciplinary guideline. European Journal of Cancer 46: 270-283.
Garcia, M., et al., (2007) Global Cancer Facts & Figures 2007. Atlanta, GA: American Cancer Association.
Giblin, A.V., et al., (2007) Incidence, morality and survival in cutaneous melanoma. Journal of Plastic, Reconstructive and Aesthetic Surgery 60(1): 32-40.
Golstein, P., et al., (2007) Cell death by necrosis: Towards a molecular definition. Trends in Biochemical Sciences 32: 37-43.
Hanahan, D., et al., (2000) The hallmarks of cancer. Cell 100: 57-70.
Holdenrieder, S., et al., (2004) Apoptotic markers in cancer. Clinical Biochemistry 37: 605-617.
International Search Report mailed Mar. 6, 2013 for PCT Application No. PCT/IB2012/057029.
Jimenez Del Rio, M., et al., (2004) Transition metal induced apoptosis in lymphocytes via hydroxyl radical generation, mitochondria dysfunction and caspase-3 activation: an in vitro model for neurodegeneration. Medical Research 35(3): 185-193.
Kerr, J.F.R., (1972) Apoptosis: a basic biological phenomenon with wide-ranging implication in tissue kinetics. British Journal of Cancer 26: 239-257.
Kerr, J.F.R.; (1994) Apoptosis: Its significance in cancer and cancer therapy. Cancer 73 (8): 2013-2022.
Khumalo, N.M., et al., (2010) Acta Cryst., E66, m451.
King, K.L. et al., (1998) Cell cycle regulation and apoptosis. Annual Review of Physiology 60: 601-617.
Kroemer, G., et al., (2009) Classification of cell death: recommendations of the Nomenclature Committee on Cell Death 2009. Cell Death and Differentiation 16: 3-11.
Kroemer, G., et al., (2007) Mitochondrial membrane permeabilization in cell death. Physiological Reviews 87: 99-163.
Kyros, L. Et al., Structural properties, cytotoxicity, and anti-inflammatory activity of silver(I) complexes with tris(p-tolyl) phosphine and 5-chloro-2-mercaptobenzothiazole, Bioinorganic Chemistry and Applications, 386860, 2010, pp. 1-12.
Lin, A.W., et al., (2000), Apoptosis in cancer. Carcinogenesis 21: 485-495.
Liu, J.J., et al., (2008) In vitro antitumour and hepatotoxicity profiles of Au(I) and Ag(I) bidentate pyridyl phosphine complexes and relationships to cellular uptake. Journal of Inorganic Biochemistry 102(2): 303-310.
Lowe, S.W., et al., (2004) Intrinsic tumour suppression. Nature 432: 307-315.
Mann, F.G., et al., (1937) J. Chem. Soc. 1828.
McCabe, M.L., et al., (2005) The molecular mechanisms of oesophageal cancer. International Pharmacology 5: 1113-1130.
Meijboom, R., et al., (2009) Coordination complexes of silver(I) with tertiary phosphine and related ligands. Coord. Chem. Rev., 253, 325-342.
Mizushima, N.; (2004) Methods for monitoring autophagy. The International Journal of Biochemistry & Cell Biology 36: 2491-2502.
Nguyen, J.T., et al., (2003) Direct activation of the apoptosis machinery as a mechanism to target cancer cells. Proceedings of the National Academy of Sciences 100: 7533-7538.
Omondi, B., et al., (2010) Acta Cryst., B66, 69. A third polymorph has also been observed. R. Meijboom, B. Omondi, unpublished results.
Poulter, Neil, et al., An organo-silver compound that shows antimicrobial activity against Pseudomonas aeruginosa as a monomer and plasma deposited film, Chemical Communications, No. 47, Dec. 21, 2009, pp. 7312-7314.
Poyraz, M., et al., Synthesis, structural characterization and biological studies of novel mixed ligan Ag(I) complexes with triphenylphoshine and aspirin or salicylic acid, Inorganica Chimica Acta, vol. 375, No. 1, Apr. 201 ,2011, pp. 114-121.
Piao, M.J., et al., (2010) Silver nanoparticles down-regulate Nrf2-mediated 8-oxoguanine DNA glycosylase 1 through inactivation of extracellular regulated kinase and protein kinase B in human Chang liver cells. Toxicology Letters 207:143-148.
Piao, M.J., et al., (2011) Silver nanoparticles induce oxidative cell damage in human liver cells through inhibition of reduced glutathione and induction of mitochondria-involved apoptosis: Toxicology Letters 201 : 92-100.
Pitot, H.C.; (2002) Fundamentals of Oncology. $4^{th}$ Ed Macel Dekker Inc, NY USA pp. 27, 901.
Rackham, D., et al., (2007) Gold(I) phosphine complex selectivity induces apoptosis in breast cancer cells: Implication for Anti-cancer therapeutics targeted to mitochondria. Biochemical Pharmacology 74: 992-1002.

(56) References Cited

OTHER PUBLICATIONS

Reed. J.C.; (1999) Dysregulation of apoptosis in cancer. Journal of Clinical Oncology 17: 2941-2953.
Reedijk, J.; (2003) New clues for platinum antitumor chemistry: Kinetically controlled metal binding to DNA. Proceedings of the National Academy of Sciences (100) 7: 3611-3616.
Sadler, P.J..et al., (1998) Metal complexes in medicine: Design and mechanism of action. Pure and Applied Chemistry 70 4 863-875.
Santini, C. et al., In vitro antitumor activity of water soluble Cu(I), Ag(I) and Au(I) complexes supported by hydrophilic alkyl phosphine ligands, Journal of Inorganiz Biochemistry, vol. 105, No. 2, Feb. 1, 2011, pp. 232-240.
Sawamura, M.; Hamashima, H.; Ito, Y.; (1990) The asymmetric a!dol reaction of tosylmethyl isocyanide and aldehydes catalyzed by chiral silver(I) complexes. Journal of Organic Chemistry. 55(24), 5935-5936.
Scherer, D., et al., (2010) Genetics of pigmentation in skin cancer—A review. Mutation Research 705: 141-153.
Segapelo, T.V., et al., (2009) (Pyrazolylmethyl) Pyridine platinum (II) and gold (III) complexes: synthesis structures and evaluation as anticancer agents. Inorganica Chemica Acta 362: 3316-3324.
Simstein, R., et al., (2003) Apoptosis, chemoresistance and breast cancer: Insights from the MCF-7 cell model system. Experimental Biology and Medicine 228: 995-1003.
Teodoro, J.S., et al., (2011) Assessment of the toxicity of silver nanoparticles in vitro: A mitochondrial perspective. Toxicology in vitro 25664-670.
Venter, G.J.S., et al., (2007) Acta Cryst., E63 m3076.
Vogelstein, B., et al., (2004) Cancer genes and the pathways they control. Nature Medicine 10 (8): 5 789-799.
Vorobiof, DA., et al., (2001) Breast cancer incidence in South Africa. Journal of Clinical Oncology 19: 125s-127s.
Wang, Z.-B., et al., (2005) Pathways to caspase activation. Cell Biology International 29: 489-496.
Zartilas, S., et al., (2009) Tetrameric 1:1 and monomeric 1:3 complexes of silver (I) halides with tri 9p-tolyl) phosphine: a structural and biological study. Inorganica Chemica Acta 362: 1003-1010.
Zhang, A., et al., (2004) Apoptosis—A Brief Review. Neuroembryology 5 (3): 47-59.
Zhivotovsky, B., et al., (2004) Apoptosis and genomic instability. Nature Reviews Molecular Cell Biology 5:752-762.
Zimmermann, K.C., et al., (2001) The machinery of programmed cell death. Pharmacology and Therapeutics 92: 57-70.
Zong, W.-X., et al., (2006) Necrotic death as a cell fate. Genes and Development 20: 1-15.

\* cited by examiner

USE OF SILVER(I) COMPLEXES AS ANTICANCER AGENTS

CROSS-REFERENCE TO RELATED APPLICATIONS

This application is a U.S. National Stage Application of International Application No. PCT/IB2012/057029 filed Dec. 6, 2012, published as WO2013/084185A1, which claims priority from South Africa Patent Application No. 2011/08944, filed Dec. 6, 2011, which are incorporated herein by reference in entirety.

FIELD OF THE INVENTION

The present invention relates to the use of silver(I) monophosphine complexes as Active Pharmaceutical Ingredients (API's), including anticancer agents, for the treatment, diagnosis and/or prevention of cancer. The present invention also relates to pharmaceutical compositions containing such complexes and further extends to a method of treating or diagnosing a subject/patient suffering from cancer.

BACKGROUND TO THE INVENTION

There are more than 100 different types of cancers known in the art to date. It has been suggested that the vast catalogue of cancer cell genotypes is a manifestation of six essential alterations in cell physiology that collectively dictate malignant growth. One of these is the ability to evade apoptosis, a form of programmed cell death occurring in metazoans (Hanahan and Weinberg, 2000). This acquired resistance to apoptosis is a hallmark of most and perhaps all types of cancer. When components of the apoptotic machinery are altered, the dynamics of tumour progression are drastically altered. Resistance to apoptosis can be acquired by cancer cells through a variety of strategies, but the most commonly occurring loss of a pro-apoptotic regulator is through the mutation of the tumour suppressor genes. The resulting functional inactivation of their products (oncoproteins) is seen in greater than 50% of human cancers and results in the removal of a key component of the DNA damage sensor that can induce the apoptotic effector cascade. Most regulatory and effector components are present in redundant form. This redundancy holds important implications for the development of novel types of anti-tumour therapy, since tumour cells that have lost pro-apoptotic components are likely to retain other similar ones (Zhivotovsky and Kroemer, 2004).

Oesophageal cancer (OC) or the cancer of the oesophagus is one of the least studied and deadliest cancers worldwide. In 2008, it was estimated that approximately 488 084 new oesophageal cancer cases had emerged with a mortality of 412 628. In the year 2030, these numbers could double exponentially (Ferlay et al., 2010). It is caused by various factors but mainly by oxidative damage such as tobacco smoking, excessive alcohol consumption, human papillomaviruses (HPV), fungal mycotoxin contamination in food, nutritional deficiencies in vitamins such as zinc, nicotinic acid, magnesium, riboflavin, selenium, and a lack of fruit and vegetables in the diet. The incidences vary globally where it is the highest in the East-Africa, South-Africa, China and central Asia regions and the lowest in the Western Africa, South-East Asia, United States and South American regions (Garcia et al., 2007). It is more prominent in black men who have a higher incidence of the disease than men in other racial or ethnic groups. In South Africa, it is the second most common cancer among all South African men combined and the most common cancer in black males (especially those in the Transkei area). Epidemiologically, OC can occur in two different forms: the squamous cell carcinoma (SCC) and the oesophageal adenocarcinoma (AC). Squamous-cell carcinoma is caused mainly by factors such as the chronic irritation and inflammation of the oesophageal mucosa, excessive alcohol intake and smoking. Oesophageal adenocarcinoma is mainly caused by the existence of gastro-oesophageal reflux disease (GERD) defined by hiatal hernia, oesophageal ulcers and the presence of the *Helicobacter pylori* infection (strains for the CagA protein) in the gastrointestinal system (Bird-Lieberman and Fitzgerald, 2009; Enzinger et al., 2003; and McCabe et al., 2005).

Breast cancer is the most commonly diagnosed cancer and cause of death in women worldwide (Ferlay et al., 2008 and Garcia et al., 2007) and in 2007 there were 1,301,867 estimated new cases and 464,854 estimated deaths from breast cancer (Garcia et al., 2007). In South Africa, breast cancer is also the most commonly diagnosed cancer in women and it constitutes on average 20% of all cancers reported in South African females (Vorobiof et al., 2001). According to the National Cancer Registry of South Africa in 2001, breast cancer was the leading cancer in Coloured and Asian women with respectively 25.48% and 30.17% of all cancers reported being breast cancer. In black women, breast cancer is the second most commonly diagnosed at 17.25%, after cancer of the cervix and in white women at 18.41% second only to basal cell carcinoma.

Transformation of various epidermal cells can give rise to several types of skin neoplasms (abnormal tissue mass) that can be divided into two main categories, namely: 1) Non-Melanoma Skin Cancer (NMSC) predominantly arising from transformed keratinocytes and 2) Cutaneous Malignant Melanoma (CMM) predominantly arising from transformed melanocytes (Scherer and Kumar, 2010). Melanomas are usually heavily pigmented but can be amelanotic. CMM can be further sub-divided into four categories classified according to clinical and histological characteristics and they are: 1) Superficial Spreading Melanoma (SSM), 2) Nodular Melanoma (NM), 3) Lentigo Maligna Melanoma (LMM) and 4) Acral Lentiginous Melanoma (ALM) (Garbe et al., 2010).

CMM has been classified as a multifactorial disease where both environmental and genetic factors/mutations interact in concert to contribute to CMM susceptibility with CMM contributing to approximately 5% of all skin cancers and approximately 1% of all malignant tumours (Bressac-de-Paillerets et al., 2002). The World Health Organisation (WHO) estimated that 132 000 new cases of CMM arise per annum internationally with CMM incidence rates showing an increase of 28% in men and 12% increase in women worldwide. The highest CMM incidence rates worldwide are found in Australia and New Zealand where it has been classified as the third most common cancer in women and fourth in men. CMM has been reported to account for 90% of all deaths associated with cutaneous tumours (Garbe et al., 2010; Giblin and Thomas, 2007). Interestingly no papers on studies have been conducted on CMM incidence rates in South Africans nor is there a skin cancer registry currently present in South Africa; however, CANSA (Cancer Association of South Africa) has reported that skin cancer is the most common cancer in this country with an estimated 20 000 new cases being reported per annum.

Lung cancer is generally caused by smoking and in minor cases, exposure to carcinogens. In South Africa, lung cancer accounted for 67% deaths in men for 2006 while 32% in women. Of the newly diagnosed cases during 2008 worldwide, lung cancer contributed 13% (Ferlay, Shin et al., 2010; Bello, Fadahun et al., 2011).

In cancer, the normal mechanisms of cell cycle regulation are dysfunctional, oncogene and tumor-suppressor gene mutations drive the neoplastic process by increasing tumor cell number through over-proliferation of cells or the inhibition of cell death or cell-cycle arrest (King and Cidlowski, 1998; Vogelstein and Kinzler, 2004; and Lowe et al., 2004). The increase can be caused by activating genes that drive the cell cycle or by inhibiting normal apoptotic processes. In healthy breast cells, apoptosis occurs at varying rates during the estrus cycle in response to changes in hormone levels. Apoptosis is however also regulated by non-hormonal signals.

Apoptosis was first characterized in 1972 when Kerr et al., (1994) published their research recognizing apoptosis as an occurrence in adults relevant to health and disease (Kroemer et al., 2007). It is now defined as a discrete sequence of well coordinated and strictly controlled energy-requiring processes in which ligand binding to death receptors or cytotoxic insults result in the activation of several proteases and other hydrolytic enzymes (Bayir and Kagan, 2008). This cascade of cell signaling and Caspase-mediated events regulating proapoptotic and antiapoptotic proteins leads to proteolysis, rounding-up of the cell and shrinkage or reduction of cellular volume, chromatin condensation (pyknosis) and segregation along the nuclear membrane, classically little or no ultrastructural modifications of cytoplasmic organelles, nuclear fragmentation (karyorrhexis) and DNA fragmentation into mono- and oligonucleosomal units, plasma membrane blebbing—although the membrane is well maintained and does not release its contents or influence behavior of adjacent cells (Simstein et al., 2003; Holdenrieder and Stieber, 2004; Elmore, 2007; Golstein and Kroemer, 2007; and Kroemer et al., 2009). Resulting cell fragments, or apoptotic bodies, are phagocytosed by macrophages and surrounding cells. Loss of phospholipid asymmetry in the plasma membrane and phosphatidylserine externalization plays an important role in the opsonization of apoptotic bodies and subsequent phagocytosis (Zimmermann et al., 2001; Danial and Korsmeyer, 2004; and Holdenrieder and Stieber, 2004).

While apoptosis involves the activation of catabolic enzymes leading to the demolition of cellular structures and organelles, autophagy is a type of cell death in which parts of the cytoplasm are sequestered within double-membraned vacuoles and finally digested by lysosomal hydrolases. Autophagy is considered to be required for the starvation response and normal turnover of cellular components and in addition may be involved in a certain type of cell death (Mizushima, 2004; Festjens et al., 2006). Autophagy is characterized by the sequestration of cytoplasmic material within autophagosomes, which are double membrane structures containing undigested cytoplasmic material including organelles and cytosol, for bulk degradation by lysosomes. The fusion between autophagosomes and lysosomes generates autolysosomes, single membrane structures in which both the autophagosome inner membrane and its luminal content are degraded by acidic lysosomal hydrolases. Autophagosomes and autolysosomes are generalized as autophagic vacuoles and, unfortunately, it is sometimes difficult to distinguish autophagic vacuoles from other structures just by morphology. Morphologically, autophagic cell death is defined (especially by transmission electron microscopy) by massive autophagic vacuolization of the cytoplasm and the absence of chromatin condensation (Kroemer et al., 2009). The functional relationship between apoptosis and autophagy is complex, and autophagy may either contribute to cell death or constitute a cellular defense against acute stress, in particular induced by deprivation of nutrients or obligate growth factors (Kroemer et al., 2007).

Necrotic cell death or necrosis is morphologically characterized by a gain in cell volume (oncosis), distended endoplasmic reticulum; formation of cytoplasmic blebs; condensed, swollen or ruptured mitochondria; disaggregation and detachment of ribosomes; disrupted organelle membranes; swollen and ruptured lysosomes; plasma membrane rupture and subsequent loss of intracellular contents. Necrosis has been considered as an accidental, uncontrolled form of cell death (Zong and Thompson, 2006; Elmore, 2007; and Kroemer et al., 2007), but evidence is accumulating that the susceptibility to undergo necrosis is partially determined by the cell (and not only by the stimulus) and that the necrotic process involves an active contribution of cellular enzymes, implying that execution of necrotic cell death may be finely regulated by a set of signal transduction pathways and catabolic mechanisms. Necrotic cell death is not the result of one well-described signaling cascade but is the consequence of extensive crosstalk between several biochemical and molecular events at different cellular levels. Recent data indicate that the serine/threonine kinase, receptor interacting protein 1 (RIP1), which contains a death domain, may act as a central initiator (Golstein and Kroemer, 2007; and Kroemer et al., 2009). Calcium and reactive oxygen species (ROS) are main players during the propagation and execution phases of necrotic cell death, directly or indirectly provoking damage to proteins, lipids and DNA, which culminates in the disruption of organelle and cell integrity. Necrotic cell death is still largely identified in negative terms by the absence of apoptotic or autophagic markers, in particular when the cells undergo early plasma membrane permeabilization as compared with its delayed occurrence in late-stage apoptosis. There is however often a continuum of apoptosis and necrosis in response to a given death stimulus. Many insults induce apoptosis at lower doses and necrosis at higher doses. Necrosis is considered to be harmful because it is often associated with pathological cell loss and because of the ability of necrotic cells to promote local inflammation that may support tumor growth. Since apoptotic cells are rapidly phagocytosed prior to the release of intracellular contents without induction of an inflammatory response (Zimmermann et al., 2001; Holdenrieder and Stieber, 2004), apoptosis is usually the preferred method of cell death.

The central component of apoptosis is a proteolytic system involving a family of proteases called Caspases or cysteine aspartate-specific proteases (Zimmermann et al., 2001). Members of the mammalian Caspase family can be divided into three subgroups depending on inherent substrate specificity, domain composition or the presumed role they play in apoptosis. They include initiators in apoptosis. Caspase-2, 8, 9 and 10 executioners in apoptosis. Caspase-3, 6 and 7 and the Caspases that participate in cytokine maturation and inflammatory responses. Caspase-1, 4, 5, 13, 11, 12, and 14 (Zhang et al., 2004; Elmore, 2007; and Chowdhury et al., 2008).

Initiator Caspases are able to activate effector Caspases or amplify the Caspase cascades by increased activation of initiator Caspases. The effector Caspases then cleave intracellular substrates, culminating in cell death and the typical biochemical and morphological features of apoptosis (Zimmermann et al., 2001). They are all expressed as single-chain proenzymes (30-50 kDa) that contain three domains:

an NH$_2$-terminal domain, a large subunit (approx. 20 kDa) and a small subunit (approx. 10 kDa). Caspases are synthesized as inactive zymogens (proenzymes) which require a minimum of two cleavages, one separating the prodomain from the large subunit and another separating the large and small subunits, to convert it to the mature enzyme (Zimmermann et al., 2001; Zhang et al., 2004; Wang et al., 2005; and Chowdhury et al., 2008). All of these cleavages involve Asp-X bonds and the cleavage between the large and small subunits precedes removal of the prodomain. Eventually a heterodimeric enzyme is formed with both fragments contributing to the formation of the catalytic machinery. Initiator Caspases possess long N-terminal prodomains that contain recognizable protein—protein interaction motifs while effector Caspases have short or no prodomains. Usually, initiator Caspases, once activated, will activate the downstream effector Caspases in a cascade-like pattern. The effector Caspases then cleave their substrates which are usually either regulatory proteins that function in the homeostatic pathways or proteins involved in the organization and maintenance of cell structures. Caspases can modify the function of their target substrates either by inactivating their normal biochemical function, activating them by removal of regulatory domains, alter or invert their function or play a proteolytic role in the disassembly of the structural components of the cytoskeleton and nuclear scaffold. The cleavage of the proteins results ultimately in cellular, morphological and biochemical alterations characteristic of apoptosis (Zimmermann et al., 2001; Zhang et al., 2004; Wang et al., 2005; and Chowdhury et al., 2008).

Although morphologically similar, there are several distinct subtypes of apoptosis that can be triggered through several molecular pathways. The two major biochemical pathways are the extrinsic or death receptor pathway and the intrinsic or mitochondrial pathway (Zimmermann et al., 2001). In the extrinsic pathway, apoptosis is activated through ligation of extrinsic signals to 'death receptors' (DR) at the cell surface which triggers intracellular signaling that leads to Caspase-8 activation (Zimmermann et al., 2001). The intrinsic pathway involves pro-apoptotic signals that translocate to the mitochondria, resulting in mitochondrial membrane permeabilization (Zimmermann et al., 2001). This, in turn, provides a route for the release of intermembrane space proteins such as cytochrome C into the cytosol which promotes the formation of the apoptosome, a molecular platform for the activation of Caspase-9. There are additional apoptotic pathways, the granzyme A-mediated pathway, the granzyme B-mediated pathway and the endoplasmic reticulum (ER)-mediated pathway.

Following initial induction, the extrinsic, granzyme B- and ER-mediated pathways merge at the level of the effector Caspases which cleave specific cellular substrates such as regulatory enzymes that result in the processing of intracellular structural proteins and eventually leads to apoptotic cell death.

The term "chemotherapy" was first introduced by Paul Ehrlich who defined it as the systematic treatment of both infectious disease and neoplasia. Chemotherapy began in 1942, when it was discovered that nitrogen mustard was an effective treatment for cancer. Cancer chemotherapy aims to treat cancer with chemicals that maximize the killing of neoplastic cells while minimizing the killing of most/all other host cells (Chabner and Roberts, 2005 and Pitot, 2002). Typical chemotherapeutic agents used today include dexamethasone, Cisplatin, etoposide, cytosine arabinoside, taxol, 5-fluorouracil, doxorubicin, topotecan and bleomycin. Most chemotherapeutic agents induce programmed cell death/apoptosis via the endogenous or intrinsic mitochondrial pathway. Chemotherapy is able to induce apoptosis in four stages (Bold et al., 1997), namely:

(i) Chemotherapeutic agent disrupts cellular homeostasis through a specific interaction with an intracellular target;
(ii) Recognition by the cell of the disruption of homeostasis;
(iii) Cell deciphers the severity of the injury and decides either to repair the injury or to proceed with apoptotic cell death; and
(iv) Initiation of apoptosis leading to cell death.

In recent years, a re-examination of the knowledge of chemotherapeutic-induced cell death has been revisited due to the complexity of cell death mechanisms (e.g. autophagy, senescence). The idea is to perhaps precisely activate or inhibit molecules that mediate the diverse forms of cell death, aiming ultimately to develop less toxic and more effective chemotherapeutic regimens. Certainly most current therapies are of a 'blunderbuss' nature (Cotter, 2009), and the designing of target-specific chemotherapeutic drugs are desirable.

Tertiary phosphine complexes of silver(I) were first prepared in 1937 (Mann et al., 1937). These coordination complexes of silver(I) salts display a rich diversity of structural types. The potential application as anti-cancer drugs of silver(I) salts follows from the analogy of the chemistry of silver(I) salts with that of gold(I) salts. Notably, however, literature on silver(I) complexes as potential anti-cancer drugs is limited to a small number of analogues of the so-called cationic lipophylic complexes. These complexes typically consist of a coinage metal (gold, silver, copper) chelated between bidentate phosphines causing a tetrahedral environment. Silver(I) complexes of bidentate pyridylphosphines were of particular interest to Meijboom et al., 2009 in their context as potential antitumour agents (Berners-Price, 1998 and Liu, 2008). The interaction between bidentate diphosphines $R_2P(R')_nPR_2$ and silver salts has attracted a great deal of interest because the resultant complexes have found some application in homogeneous catalysis (Sawamura, 1990) and also as antitumour compounds (Berners-Price, 1988 and Barnard, 2007). However, the interplay of various parameters such as the geometrical flexibility of Ag(I), the bite angle and the electronic properties of the phosphine as well as the coordination mode of the supporting ligands, often renders predictions concerning the structural properties of silver-phosphine complexes difficult (Berners-Price, 1988), both in solution and in the solid state (Brandys, 2002). This difficulty is exemplified by the crystallisation of these complexes in more than one polymorph. Generally, a tetrahedral environment around the silver(I) atom is preferred in the solid state, however many exceptions to this tetrahedral environment have been observed. To date, little systematic work has been reported on the interaction between silver salts and diphosphines characterized by different spacers (lR') or substituents R. Despite the obviously interesting structural chemistry of silver(I), and the potential of these complexes as anti-cancer agents, cognizance should be had to the fact that relatively few publications on silver(I) complexes as anti-cancer agents have been reported in literature.

While little systematic work is reported on the interaction of diphosphines with silver, and their resulting applications as anti-cancer agents, even less has been reported on the use of monophosphines. To date, the only systematic studies on monophosphines with silver are two series of papers by White et al. on the coordination ability of PPh$_3$ and PCy$_3$ to silver(I). These papers (reviewed in Meijboom, 2009) dealt exclusively with the structural chemistry of the resulting complexes and did not report any (potential) applications. What became clear from these papers, however, is that the coordination chemistry of silver(I) complexes is an extremely rich and varied field, with a range of structural types (nineteen different structural types have been identified in Meijboom, 2009). A comprehensive (and ongoing) search of the literature revealed only two papers by Zartilas et al. (2009) on the coordination of P(4-MeC$_6$H$_4$) to silver halides reporting extremely limited data on anti-cancer testing (IC50 values only).

In the light of the foregoing, it is apparent that there is a clear need in the art to explore the potential of silver(I) monophosphine complexes as anti-cancer agents with a view to understanding the molecular mechanisms through which these complexes induce cell death and the mechanism of cytotoxicity of these complexes.

SUMMARY OF THE INVENTION

According to a first aspect thereof, the present invention provides for use of an effective amount of a silver(I) complex of the general Formula (I):

$$[(Ag)X(L)_m]_n \quad (I)$$

or pharmaceutically acceptable salts, polymorphs or derivatives thereof, as an Active Pharmaceutical Ingredient (API), including an anticancer agent, for the treatment, diagnosis and/or prevention of cancer in a subject, wherein:

Ag is silver in its oxidation state of one;

X is a coordinating or non-coordinating anion selected from the group consisting of Cl$^-$; Br$^-$, I$^-$, F$^-$, CN$^-$, PO$_4^{3-}$, NO$_3^-$, NO$_2^-$, ClO$_4^-$, BF$_4^-$, PF$_6^-$, SO$_4^{2-}$, CO$_3^{2-}$, H$_3$CCO$_2^-$, F$_3$CCO$_2^-$ and F$_3$CSO$_3^-$;

L is a mono-dentate phosphine ligand (PR$_3$);

m is an integer from 1 to 4, both inclusive; and n is an integer from 1 to ∞, both inclusive.

According to the invention, the R groups may either be the same or different. The R groups may be independently selected from the group of substituents consisting of hydrogen, C$_1$ to C$_{12}$ straight or branched or cyclic alkyl moieties, C$_6$ aryl moieties, metallocene moieties and adamantyl moieties, wherein the said moieties may be unsubstituted or substituted by one or more substituents selected from the group consisting of C$_1$ to C$_{12}$ straight or branched or cyclic alkyl moieties, alkoxy moieties, haloalkyl moieties, hydroxyl moieties, carbonyl moieties, aldehyde moieties, haloformyl moieties, carboxylic moieties, ester moieties, amine moieties, imine moieties and sulfide moieties.

Non limiting examples of the R groups are provided herein under as follows.

Where R is an alkyl group or a substituted alkyl group, the alkyl group may comprise 1 to 6 carbon atoms, more preferably 1 to 4 carbon atoms and most preferably 1 to 2 carbon atoms. R may be selected from the group consisting of methyl, ethyl, propyl, isopropyl, 1,2-dimethylpropyl (3-methyl-2-butyl), 1,2,2-trimethylpropyl(R/S-3,3-dimethyl-2-butyl), allyl, butyl, tertiary-butyl, sec-butyl, pentyl, isopentyl, neopentyl and hexyl.

Where R is an aryl group or a substituted aryl group, R may be selected from the group consisting of phenyl, 1-methylphenyl, 2-methylphenyl, 3-methylphenyl, 4-methylphenyl, 2,6-dimethyl-phenyl, 2-methoxyphenyl, 3-methoxyphenyl, 4-methoxyphenyl, 4-tertiary-butylphenyl, 4-nitrophenyl, 4-fluorophenyl, 4-chlorophenyl and 4-methoxyphenyl.

Where R is a cyclic alkyl group or a substituted cyclic alkyl group, R may be selected from the group consisting of cyclopropyl, cyclobutyl, cyclopentyl, cyclohexyl, cycloheptyl, cyclo-octyl, cyclononyl, cyclodecyl, 2-methylcyclohexyl, 3-methylcyclohexyl, 4-methylcyclohexyl 2,6-dimethylcyclohexyl, 2-ethylcyclohexyl and 2-isopropylcyclohexyl.

In terms of one embodiment of the instant invention. X is SCN$^-$ and L is PR$_3$ wherein each R group is the same. In terms of this embodiment, each R group is either a C$_6$ aryl group or a substituted C$_6$ aryl group. Preferably, each R group is selected from the group consisting of phenyl, 4-methylphenyl, 4-fluorophenyl, 4-chlorophenyl and 4-methoxyphenyl. In terms of this embodiment, m is 2.

Illustrative, non-limiting examples of silver(I) thiocyanate phosphine complexes of Formula (I) that may be employed in the present invention include:

[AgSCN(PPh$_3$)$_2$]$_2$;
[AgSCN{P(4-MeC$_6$H$_4$)$_3$}$_2$]$_2$;
[AgSCN{P(4-FC$_6$H$_4$)$_3$}$_2$]$_2$;
[AgSCN{P(4-ClC$_6$H$_4$)$_3$}$_2$]$_2$; and
[AgSCN{P(4-MeOC$_6$H$_4$)$_3$}$_2$]$_n$.

In terms of a further embodiment of the instant invention, X is NO$_3^-$; and L is PR$_3$ wherein each R group is the same. In terms of this embodiment, each R group is a C$_6$ aryl group and m is either, 1, 2, 3 or 4.

Illustrative, non-limiting examples of silver(I) nitrate triphenylphosphine complexes of Formula (I) that may be employed in the present invention include:

AgNO$_3$(PPh$_3$);
AgNO$_3$(PPh$_3$)$_2$;
AgNO$_3$(PPh$_3$)$_3$, and
AgNO$_3$(PPh$_3$)$_4$.

In terms of a further embodiment of the instant invention. X is Cl$^-$; Br$^-$ or CN$^-$ and L is PR$_3$ wherein each R group is the same. In terms of this embodiment, each R group is a C$_6$ aryl group and m is 3.

Illustrative, non-limiting examples of silver(I) chloride triphenylphosphine complexes, silver(I) bromide triphenylphosphine complexes and silver(I) cyanide triphenylphosphine complexes of Formula (I) that may be employed in the present invention include:

AgCl(PPh$_3$)$_3$;
AgBr(PPh$_3$)$_3$; and
AgCN(PPh$_3$)$_3$.

Thus, according to the invention, the silver(I) monophosphine complexes in accordance with Formula (I) or pharmaceutically acceptable salts, polymorphs or derivatives thereof, may be used as Active Pharmaceutical Ingredients (API's) including anticancer agents for selectively inhibiting the activity of cancer cells.

According to a second aspect of the invention, there is provided a pharmaceutical composition comprising a silver (I) monophosphine complex according to Formula (I) or pharmaceutically acceptable salts, polymorphs or derivatives thereof, as herein before described, in combination with one or more pharmaceutically acceptable excipients, additives or carriers. The excipients are preferably inert and in any event non-toxic to the subject/patient for which the pharmaceutical composition is intended.

In an embodiment of this aspect of the invention, the pharmaceutical excipients, additives and carriers may include, but are not limited to including, proteins, peptides, amino acids, lipids, and carbohydrates (e.g. sugars, including monosaccharides, di-, tri-, tetra-, and oligosaccharides; derivatized sugars such as alditols, aldonic acids, esterified sugars and the like; and polysaccharides or sugar polymers), which can be present singly or in combination.

According to a third aspect of the invention, there is provided the use of a silver(I) monophosphine complex according to Formula (I) or pharmaceutically acceptable salts, polymorphs or derivatives thereof, as herein before described, in the manufacture of a medicament for the treatment, diagnosis and/or prevention of cancer.

The invention further provides for the use of a silver(I) monophosphine complex according to Formula (I) or pharmaceutically acceptable salts, polymorphs or derivatives thereof, as herein before described, for selectively inhibiting the activity of cancer cells.

In terms of the present invention, the cancer may be selected from the group consisting of breast cancer, oesophageal cancer, lung cancer, colon cancer, ovarian cancer, leukaemia, renal cancer, melanoma cancer, prostrate cancer, CNS cancer, carcinoma, lymphoma, blastoma, sarcoma, leukemia, gastric or stomach cancer, gastrointestinal cancer, pancreatic cancer, gliobiastoma, cervical cancer, ovarian cancer, liver cancer, bladder cancer, cancer of the urinary tract, hepatoma, rectal cancer, colorectal cancer, endometrial or uterine carcinoma, salivary gland carcinoma, vulval cancer, thyroid cancer, hepatic carcinoma, anal carcinoma and penile carcinoma.

It will be appreciated that the scope of the present invention is not limited to the cancer types identified herein.

According to a fourth aspect of the invention, there is provided a method of treating or diagnosing a subject/patient suffering from cancer comprising administering to a subject patient in need thereof an effective amount of the silver(I) monophosphine complex according to Formula (I) or pharmaceutically acceptable salts, polymorphs or derivatives thereof, as herein before described.

The invention also provides a method of inhibiting metastasis of cancer comprising administering to a subject in need thereof an effective amount of the silver(I) monophosphine complex according to Formula (I) or pharmaceutically acceptable salts, polymorphs or derivatives thereof, as described herein.

The invention further provides a method of reducing cell growth of cancer comprising administering to a subject in need thereof an effective amount of the silver(I) monophosphine complex according to Formula (I) or pharmaceutically acceptable salts, polymorphs or derivatives thereof, as described herein.

The pharmaceutical composition described herein may be delivered by a variety of suitable drug delivery systems known and described in the art. Non-limiting examples of drug delivery systems and technologies for administering the pharmaceutical composition of the present invention in order to achieve the desired therapeutic effect include, but are not limited to, oral, nasal, and topical administration, administration by way of inhalation, administration by way of injection and administration by way of nanobiotechnology pharmaceutical delivery systems and devices.

The invention further provides for the pharmaceutical composition, as described herein, to optionally include a therapeutic agent.

The invention yet further provides for the pharmaceutical composition, as described herein, to optionally be administered together with an additional pharmaceutical preparation or a therapeutic agent.

According to a further aspect of the present invention, there is provided a composition including the silver(I) monophosphine complex according to Formula (I) or pharmaceutically acceptable salts, polymorphs or derivatives thereof, as identified herein, for use as a diagnostic agent.

According to a yet further aspect of the present invention, there is provided for one or more kits including the silver(I) monophosphine complex according to Formula (I) or pharmaceutically acceptable salts, polymorphs or derivatives thereof, as identified herein, for the detection of cancer in a subject/patient.

According to the invention, the effective dosage of the silver(I) monophosphine complex according to Formula (I) is at least ten times more effective in inducing cell death when compared to dosages of known chemotherapeutic drugs, such as Cisplatin.

According to a yet further aspect of the invention, there is provided a process for preparing a silver(I) monophosphine complex as defined according to Formula (I), for use as an anticancer agent, the process including the steps of:

(a) providing a silver(I) salt selected from the group consisting of AgCl; AgBr, AgI, AgF, AgCN, AgSCN, $Ag_3PO_4$, $AgNO_3$, $AgNO_2$, $AgClO_4$, $AgBF_4$, $AgPF_6$, $Ag_2SO_4$, $Ag_2CO_3$, $AgH_3CCO_2$, $AgF_3CCO_2$ and $AgF_3CSO_3$;

(b) providing a source of a mono-dentate phosphine ($PR_3$) ligand; and (c) combining the silver(I) salt and the source of the mono-dentate phosphine ligand to obtain a silver(I) monophosphine complex of Formula (I) as herein before described and identified.

According to an embodiment of this aspect of the invention, 1 mmol to 4 mmol of the phosphine ligand is added to 1 mmol of the silver(I) salt.

The molar ratio of the silver(I) salt:phosphine ligand may either be 1:1, 1:2, 1:3 or 1:4 in respect of complexes of Formula (I).

The silver(I) salt of step (a) and the source of the mono-dentate phosphine ligand of step (b) may be combined in any manner known in the art. In an embodiment of the invention, the silver(I) salt and the source of the mono-dentate phosphine ligand are co-dissolved in a solvent. Solvents such as acetonitrile, pyridine, ethanol and methanol may be used. In a preferred form of the invention, the solvent mixture is acetonitrile.

These and other objects, features and advantages of the invention will become apparent to those skilled in the art following the detailed description of the invention as set out in the Examples and as is depicted in the accompanying Figures.

Figure 1A:
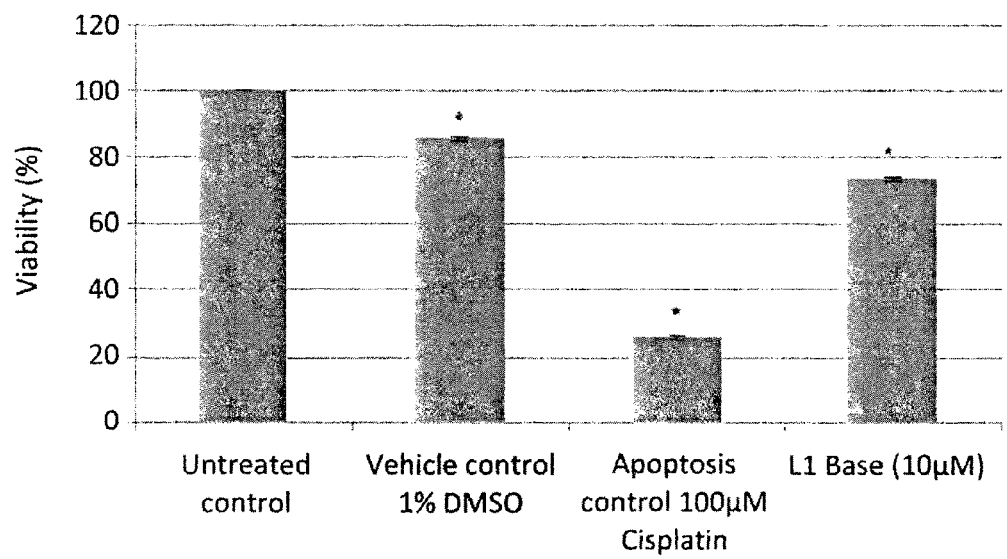
FIG. 1A: Graph depicting the percentage viability of control samples determined by the AlamarBlue® viability and proliferation assay.
Figure 1A:
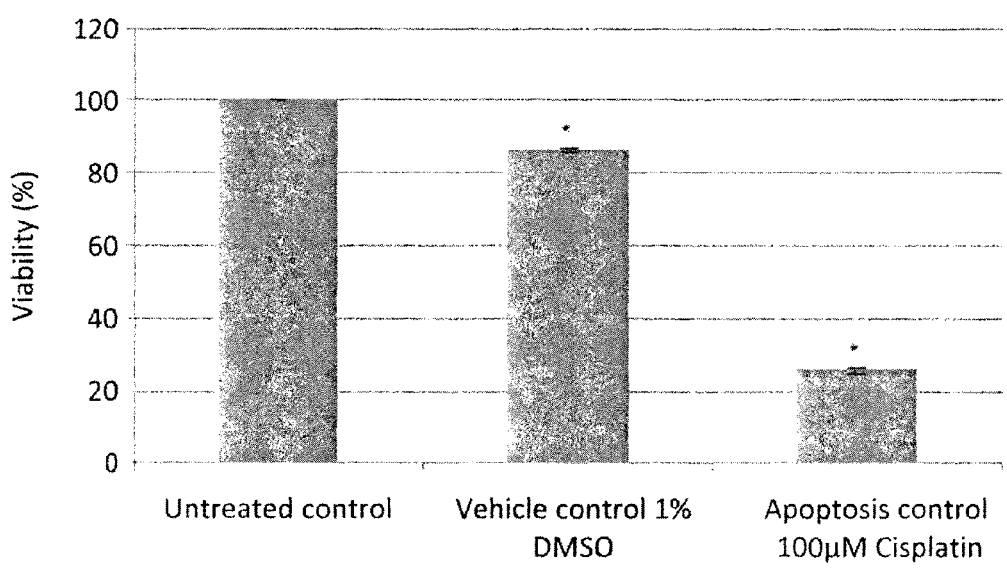

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

EXAMPLES

A: Silver(I) Thiocyanate Phosphine Complexes of the Invention and the Toxicity Evaluation Thereof on MCF-7 Breast Cancer Cells and SNO-Oesophageal Cancer Cells 1. General The silver(I)thiocyanate salt, the various phosphine ligands and acetonitrile were purchased from Sigma-Aldrich and used as received. 31P NMR spectra of the silver(I) phosphine complexes were recorded in deuterated chloroform on Bruker AC 300 spectrometer at 121.4 MHz. Melting points were determined on a Mettler Toledo DSC822e device. The fast atomic bombardment (FAB) mass spectra were recorded on a Micromass VG70SEQ instrument at the University of the Witwatersrand, RSA.

For the biological studies. MCF-7 breast cancer cells were obtained from an immortal cell line from human adenocarcinoma from (primary site) mammary gland and (metastatic site) pleural effusion (ATCC no HTB-22).

SNO-oesophageal cancer cells were a gift from the University of Pretoria, RSA. Dulbecco's modified Eagles media (DMEM), Foetal Bovine Serum (FBS), and the antibiotic supplements were all purchased from Highveld Biological (Kelvin, RSA). Cell culture graded dimethyl sulpoxide (DMSO) was obtained from AppliChem (Darmstad, Germany). Cisplatin (CDDP) was purchased from Molekula (Dorset, UK) while hydrogen peroxide ($H_2O_2$) was purchased from Minema (Gauteng, RSA). AlamarBlue® dye and the Annexin-V FITC assay kit were obtained from Serotec (Oxford, UK). All reagents were used as supplied.

2. Synthesis of Complexes

Preparation of Silver(I) Thiocyanate Phosphine Complexes of the Invention

Example 1

[AgSCN(PPh$_3$)$_2$]$_2$ Complex (1)

Solid AgSCN (0.0517 g, 0.31 mmol) was added to the solution of triphenyl phosphine (PPh$_3$) (0.2481 g, 0.95 mmol) in ethanol (40 cm$^3$) and DMSO (30 cm$^3$). The reaction mixture was heated under reflux for 5.5 h at 87° C. The solution was filtered hot and the ethanol was evaporated. The solution was placed in a freezer which resulted in a frozen mixture and upon melting small white crystals were isolated and recrystallized from DCM. Yield: 0.0892 g, 30%; mp 170-173° C. IR: $v_{max}$/in cm$^{-1}$: 2058.32 (v(SCN), s); 1477.36, 1432.25 (v(C=C aromatic), s); 1307.63 (w); 1155.06 (w); 1090.38, 1059.97 (asymm, m); 1026.02, 997.43 (m); 744.26 (v(aromatic, C—H bend), s); 692.39 (v(aromatic, C—H bend, meta), s). $^1$H NMR: (400 MHz, CDCl$_3$) δ (ppm) 7.31 (m, 45H, H-aromatic). $^{13}$C {H} NMR: (100 MHz, CDCl$_3$) δ (ppm) 128.80 (d, $δ_1$=128.756, $δ_2$=128.844, $^1$J(P—C)=6.6 Hz, meta C); 129.81 (para C); 133.77 (d, $δ_1$=133.692, $δ_2$=133.862, $^1$J(P—C)=12.7 Hz, ipso C). $^{31}$P NMR: in CDCl$_3$ δ (ppm) 4.58. Elemental Analysis: Anal. Calcd for AgSCN:PPh$_3$ (1:3): C, 69.33; H, 4.76; N, 1.47; S, 3.37. Found: C, 69.36; H, 5.31; N, 1.48; S, 3.42.

Example 2

[AgSCN{P(4-MeC$_6$H$_4$)$_3$}$_2$]$_2$ Complex (2)

In a 100 ml round bottomed flask, 100 mg of AgSCN (0.603 mmol, 165.95 g/mol) and 0.367 mg (1.206 mmol, 304.37 g/mol) of [P(p-MeC$_6$H$_4$)$_3$] were dissolved in 30 ml of pyridine. The reaction mixture was stirred under reflux (115° C.) overnight. After filtration, the pyridine solution was allowed to stand at room temperature and a solid crashed out. The latter was collected and recrystallized in acetonitrile. Yield: 0.314 g; mp (DSC): 181° C.; $^1$H NMR: (CDCl$_3$, δ, 300 MHz): 2.47 (s, 3H); 7.22 (d, 2H); 7.35 (d, 2H). $^{13}$C NMR: (CDCl$_3$, δ, 75.5 MHz): 21.76; 129.00; 129.39; 134.22; 140.69. $^{31}$P NMR: (CDCl$_3$, δ, 121.4 MHz): 7.48; MS (M/z): 717.3=Ag[P(p-CH$_3$C$_6$H$_4$)$_3$]$_2$; 411.1=AgP(p-CH$_3$C$_6$H$_4$)$_3$ EA: % H, 5.46 (Calculated); 5.29 (Found); % N, 1.81 (calculated); 1.55 (Found); % C, 62.70 (Calculated); 63.40 (Found).

Example 3

[AgSCN{P(4-FC$_6$H$_4$)$_3$}$_2$]$_2$ Complex (3)

To a suspension of AgSCN (1 mmol) in acetonitrile (10 cm$^3$) was added a solution of P(4-FC$_6$H$_4$)$_3$ (1-4 mmol) in acetonitrile (20 cm$^3$). The mixture was heated under reflux until all solids dissolved. The mixture was cooled to room-temperature and the product allowed to crystallize out. The solids were isolated by filtration and dried in vacuo to give the respective product. mp 210-215° C.; Solid IR (v in cm$^{-1}$): 3029 (v(=C—H), w); 2360 (v(C—H), w); 2081 (v(SCN), m); 1586, 1558, 1541 (v(C=C aromatic), asymm, s); 1492 (asymm, s) 1394 (v(C=C aromatic), m); 1299, 1273, 1224, 1158 (v(OCH$_3$), s); 1093 (s), 1043 (m) 1012 (s); 824 (v(aromatic, δ C—H para), asymm, s); 707 (v(aromatic, δ C—H mono), asymm, s). $^1$H NMR: (400 MHz, CDCl$_3$): δ (ppm) 6.940 (t); 7.280 (t). $^{31}$P NMR: (161 MHz, CDCl$_3$): δ (ppm) 2.82. $^{13}$C{H} NMR: (100 MHz, CDCl$_3$): δ (ppm) 116.36 (q); 128.22 (q); 135.73 (q); 169.05 (d).

Example 4

[AgSCN{P(4-ClC$_6$H$_4$)$_3$}$_2$]$_2$ Complex (4)

A 0.025 g of AgSCN was weighed and added to a solution of 100 mg g, 0.0003M tris parachlorophenyl phosphine ligand [P(p-ClC$_6$H$_4$)$_3$] in 40 ml acetonitrile. The solution was then refluxed for 1 hour, hot filtered on a whatman 3 filter paper. The solution was evaporated on a hot plate until the crystals started precipitating out. The complex was then allowed to stand for 24 hrs and the concentrated solvent decanted off. The sample was washed with two portions of fresh 2 ml acetonitrile solution. The product was obtained by drying under high vacuum and the product characterized as follows. IR: 3055w, 2075s (SCN), 1574m, 1560m, 1477s, 1385m, 1298w, 1180w, 1079s, 1011s, 813s, 744s, 704w, 630w. $^1$H NMR: (400 MHz, CDCl$_3$) δ=7.53 (s), 7.46-7.42, 7.28-7.21, 7.06-7.01. $^{13}$C NMR: (101 MHz, CDCl$_3$) δ (ppm) 137.01 ($s_1$ $d_4$) 134.85 ($d_1$, J=0.18 Hz) 130.85. $^{31}$P NMR: (162 MHz, CDCl$_3$) 6 (PPM) 2.45 (S). ($d_2$, J=0.189 Hz) 129.36 ($d_3$, J=0.097 Hz). Elemental Analysis: C, (49.53); H, (2.70); N, (1.556); S, (3.57). % found C, (49.42); H, (2.65); N, (1.75).

Example 5

[AgSCN{P(4-MeOC$_6$H$_4$)$_3$}$_2$]$_n$ Complex (5)

In a 100 ml round bottomed flask, 100 mg of AgSCN (0.603 mmol, 165.95 g/mol) and 0.4250 mg (1.206 mmol, 352.37 g/mol) of [P(p-MeOC$_6$H$_4$)$_3$] were dissolved in 30 ml of pyridine. The reaction mixture was stirred under reflux (115° C.) overnight. After filtration, the pyridine solution was allowed to stand at room temperature and a solid crashed out. The latter was collected and recrystallized in acetonitrile. Yield: 0.350 g; mp (DSC): 183° C.; $^1$H NMR: (CDCl$_3$, δ, 300 MHz): 3.90 (s, 3H); 6.93 (d, 2H); 7.40 (d, 2H). $^{13}$C NMR: (CDCl$_3$, 6, 75.5 MHz): 55.62; 114.80; 114.94; 135.72; 161.50. $^{31}$P NMR: (CDCl$_3$, 6, 121.4 MHz): 5.63; MS (M/z): 813.2=Ag[P(p-OCH$_3$C$_6$H$_4$)$_3$]$_2$; 459.1=AgP(p-OCH$_3$C$_6$H$_4$)$_3$; EA: % H, 4.86 (Calculated); 5.013 (Found); % N, 1.60 (Calculated); 1.40 (Found); % C, 59.36 (Calculated); 61.10 (Found).

For ease of reference, the chemical structures of complexes (1)-(5) are provided herein below:

Complex (1)
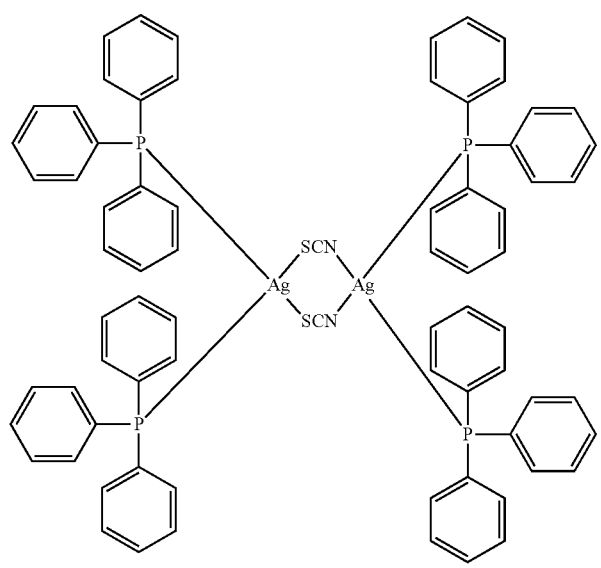
Complex (2)
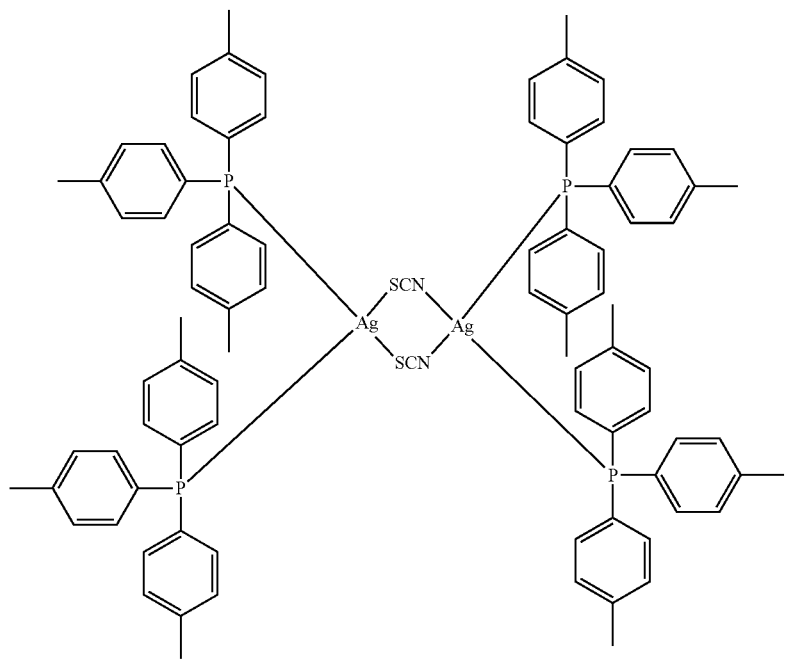

Complex (3)
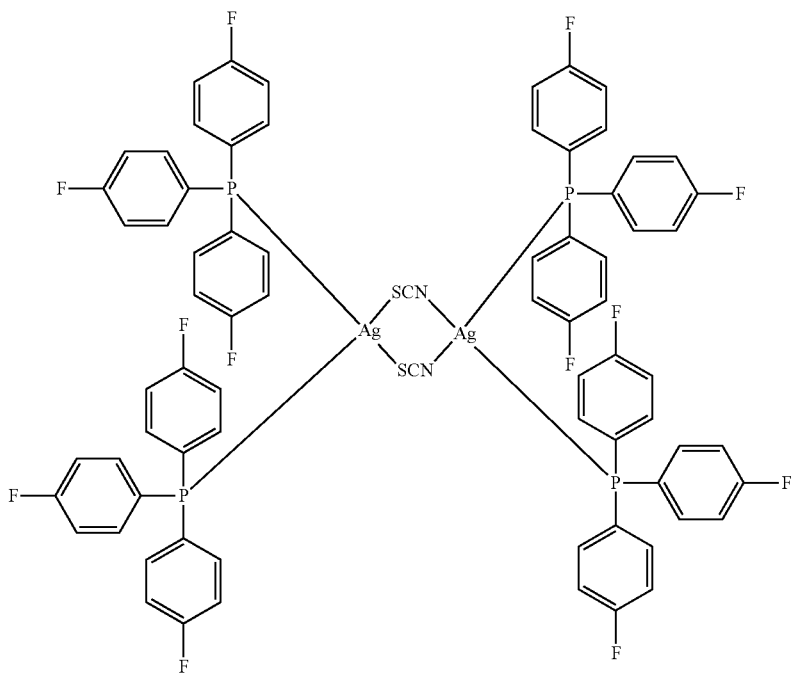
Complex (4)
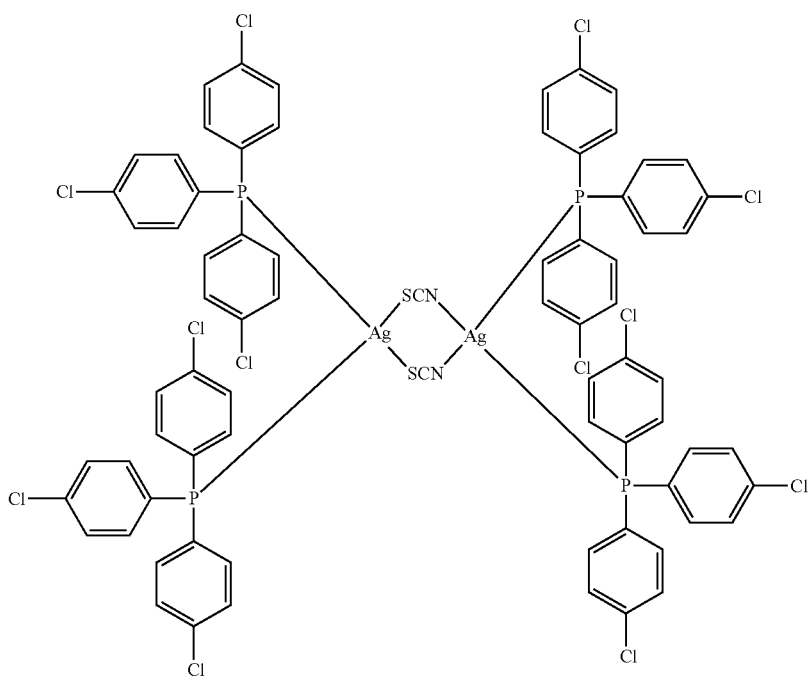

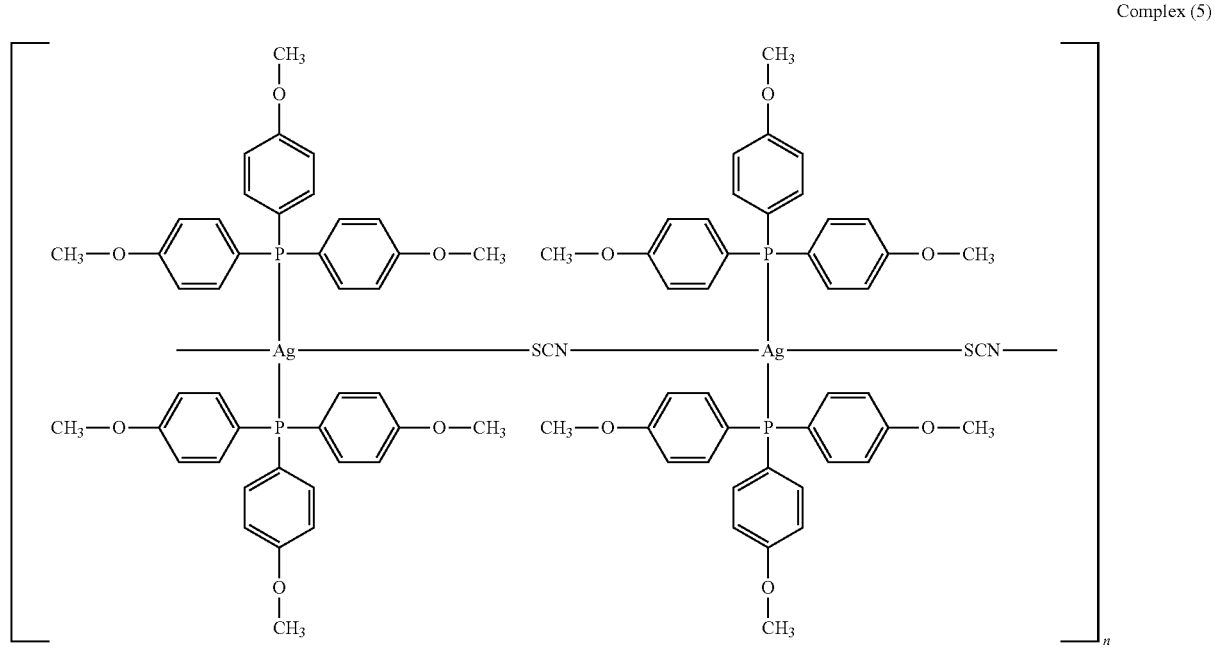

Complex (5)

3. Cell Culturing and Treatment

For the initial dose-responsive studies, complexes (1)-(5) were selected together with two cancer cell lines, namely, the MCF-7 breast cancer cells (as set forth in Item 4.1 below) and the SNO-oesophageal cancer cells (as set forth in Item 4.2 below).

MCF-7 breast cancer cells were cultured in Dulbecco's modified Eagle's medium (DMEM), 13.53 g/L with sodium bicarbonate (NaHCO$_3$). 3.7 g/L supplemented with 10% foetal bovine serum (FBS), 1% gentamycin and 5% Penecillin/Streptomycin/Fungizone in 75 cm$^3$ culture flasks. Cells were subcultured twice a week and incubated at 37° C. with 5% CO$_2$ in a humidified atmosphere. Hanks balanced salt solution (HBSS), supplemented DMEM media and trypsin versene were warmed to 37° C. prior to subculturing. Cells were washed twice with 10 ml Hanks balanced salt solution for 1 minute and were then incubated for 4.5 to 5 minutes at 37° C. with 6 ml trypsin versene to remove the cells from the culture flask. To inactivate the trypsin versene, 10 ml supplemented DMEM was added and the cells were pelleted by centrifugation at 1028 g for 4 minutes with an Allegra™ 25R Centrifuge. The pellet was resuspended in 1 ml supplemented DMEM and 500 of the cell suspension was then added to 25 ml of supplemented DMEM media in 75 cm$^3$ culture flasks.

The SNO-oesophageal cancer cells were cultured in Dulbecco's modified Eagles medium (DMEM) containing 10% Foetal bovine serum (FBS), 0.8% Penicillin/Streptomycin/Fungizone and 0.2% Gentamycin. The SNO-oesophageal cancer cells were subcultured every 48 hours and incubated at 37° C. under a 5% CO$_2$ humidified atmosphere. After 48 hours the cells were trypsinized and plated (6×10$^5$ cells) in 3.5 cm culture dishes and left to cultivate for 24 hours.

MCF-7 breast cancer cells, in terms of a first study, and SNO-oesophageal cancer cells, in terms of a second study, were treated with 10 µM silverthiocyanide complexes (1)-(5), as well as their ligands (Ligand-1 to Ligand-5) over a 24 hour incubation period. These complexes were dissolved in 0.1% Dimethyl sulfoxide (DMSO). The DMSO alone (vehicle control) decreased the viability with approximately 2.2%, signifying its minimal influence in cancer cell growth. For comparative purposes, 100 µM Cisplatin (CDDP) and 25% H$_2$O$_2$ was included which respectively serves as the apoptotic and necrotic controls. Cisplatin was prepared in 0.9% NaCl, whereas H$_2$O$_2$ was prepared in the supplemented DMEM media right before treatment. An untreated negative control (UT) was exposed to similar conditions as the treated cells and monitored during the experimental study.

Several assays were used to evaluate the effect of complexes (1)-(5) on cell death with respect to the MCF-7 breast cancer cells and the SNO-oesophageal cancer cells. These included cell viability assays such as the AlamarBlue® viability and proliferation assay and the Trypan blue exclusion assay, microscopy to evaluate cell morphology and flow cytometric analysis of apoptosis and/or necrosis.

4. Cell Viability and Morphological Studies

4.1 MCF-7 Breast Cancer Cell Assays

The AlamarBlue® Viability and Proliferation Assay of MCF-7 Breast Cancer Cells

The AlamarBlue® viability and proliferation assay of complexes (1)-(5) for the MCF-7 breast cancer cells is depicted in FIGS. 1A to 1F. The percentage viability of control samples determined by the AlamarBlue® viability and proliferation assay is depicted in FIG. 1A. MCF-7 cells were treated with 1% DMSO as a vehicle control as well as 00 µM Cisplatin as a positive apoptosis control. Untreated cells served as a negative control. The error bars represent the standard error of the mean (SEM n=9). A significant difference (P<0.001) between the control and the treated samples was calculated using Student's T-test and is indicated by an asterisk.

Figure 1B:
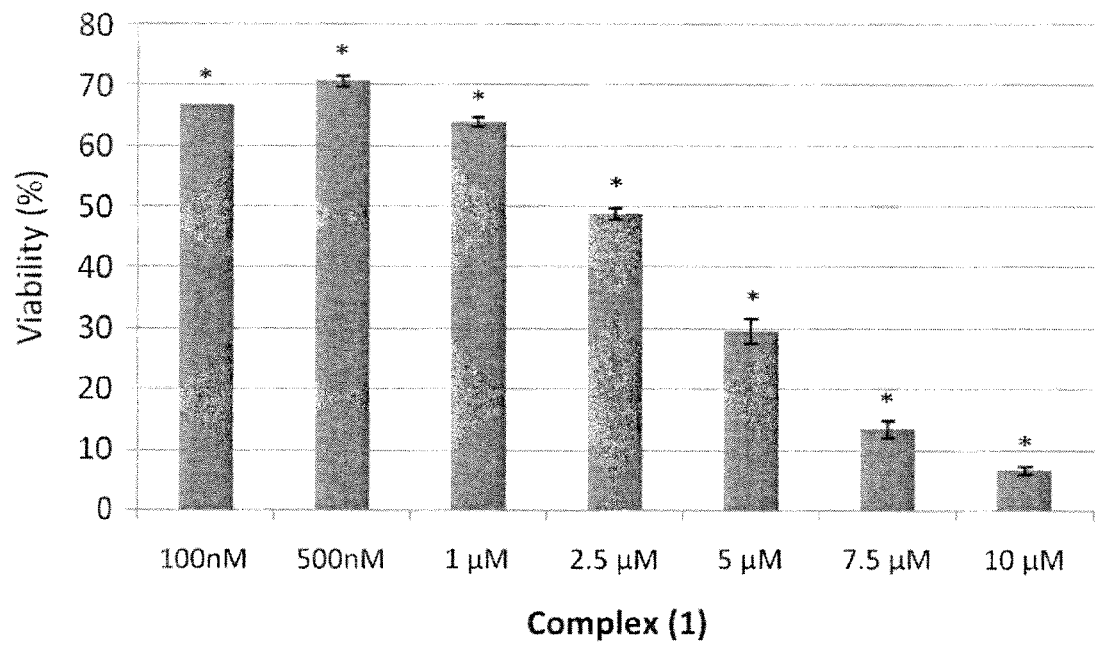
FIG. 1B: Graph depicting the dose dependant studies of complex (1) determined by the AlamarBlue® viability and proliferation assay.
Figure 1C:
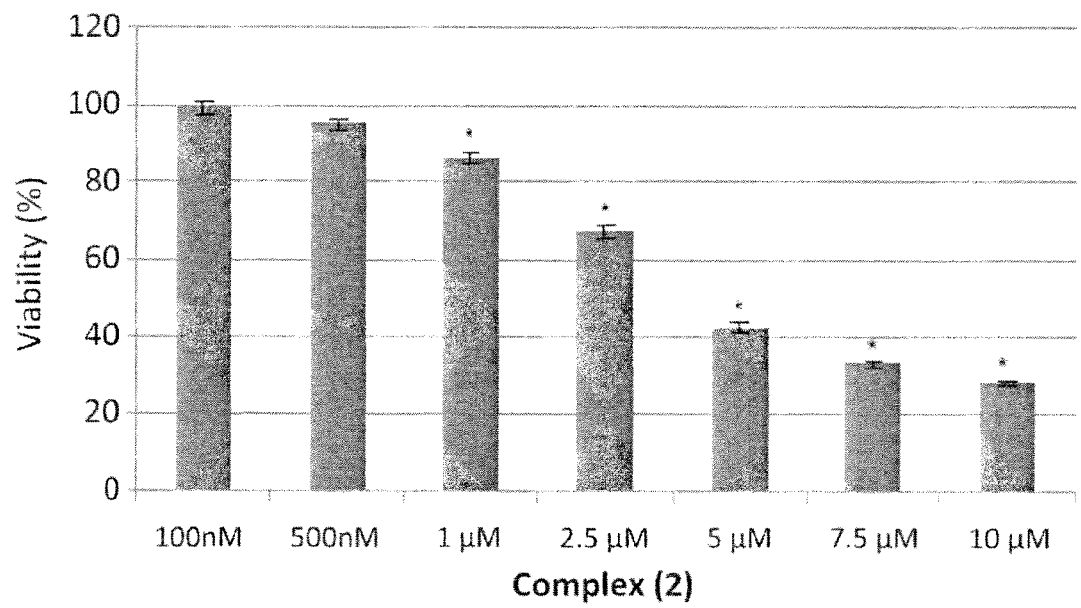
FIG. 1C: Graph depicting the dose dependant studies of complex (2) determined by the AlamarBlue® viability and proliferation assay. The SEM is indicated as error bars (n=9)
Figure 1D:
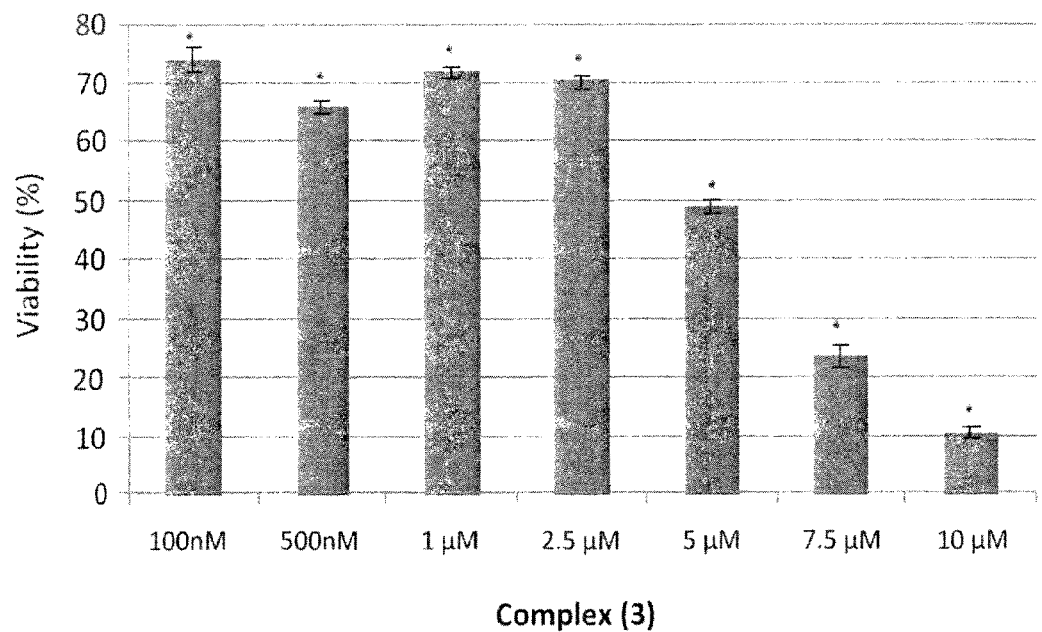
FIG. 1D: Graph depicting the dose dependant studies of complex (3) determined by the AlamarBlue® viability and proliferation assay. The SEM is indicated as error bars (n=5)
Figure 1E:
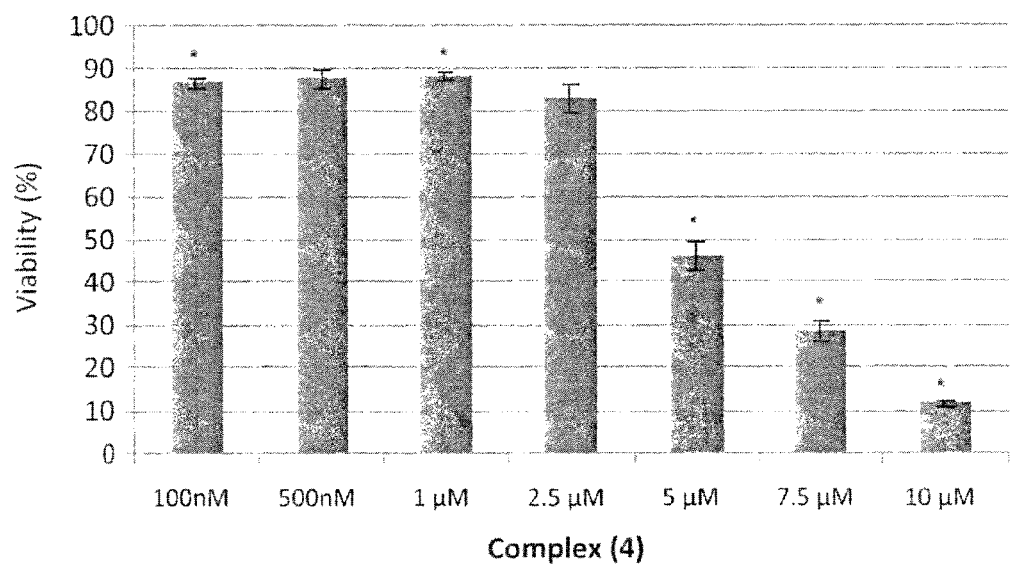
FIG. 1E: Graph depicting the dose dependant studies of complex (4) determined by the AlamarBlue® viability and proliferation assay. The SEM is indicated as error bars (n=9)
Figure 1F:
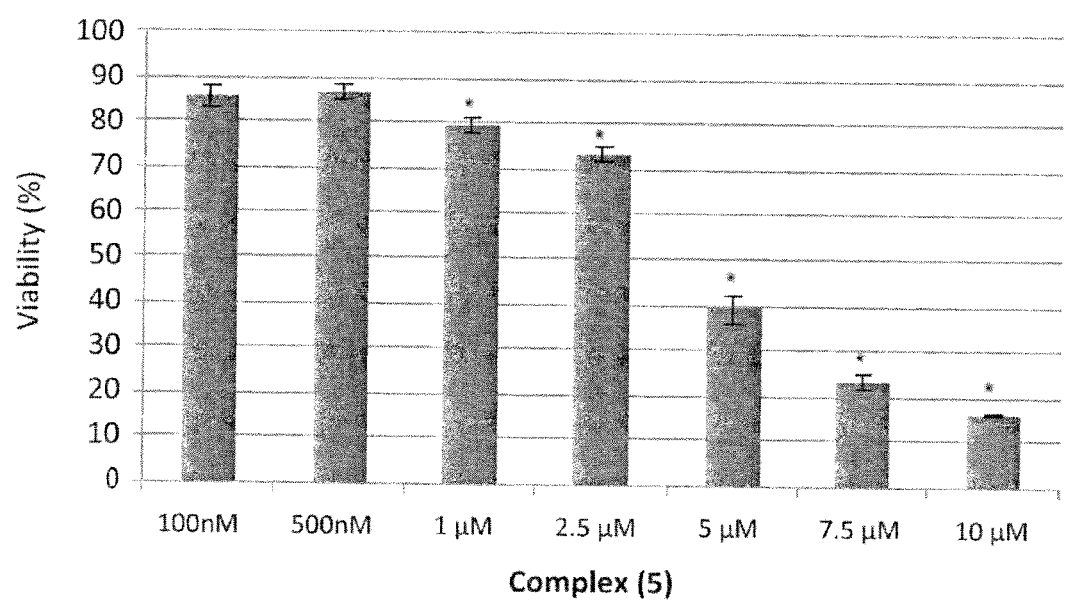
FIG. 1F: Graph depicting the dose dependant studies of complex (5) determined by the AlamarBlue® viability and proliferation assay. The SEM is indicated as error bars (n=9)

The dose dependant studies of complex (1) are shown in FIG. 1B. This Figure depicts the percentage viability of MCF-7 cells treated with various concentrations of complex (1) as determined by the AlamarBlue® viability and proliferation assay. Viability is represented as a percentage with the control at 100%. The asterisk indicates a significant difference between a sample and the control (P<0.001) as calculated with Student's T-test.

FIG. 1C to FIG. 1F represent the dose dependant studies of complexes (2) to (5), respectively. In each of these Figures, the percentage viability of MCF-7 cells treated with various concentrations of complexes (2) to (5) was determined by the AlamarBlue® viability and proliferation assay. Viability is represented as a percentage with the control at 100%. Cells were treated with different concentrations of complexes (2) to (5). The asterisk indicates a significant difference between a sample and the control (P<0.001) as calculated with Student's T-test.

The Trypan Blue Exclusion Assay of MCF-7 Breast Cancer Cells

The Trypan blue exclusion assay of complexes (1)-(5) for the MCF-7 breast cancer cells is depicted in FIGS. 2A to 2F.

Figure 2A:
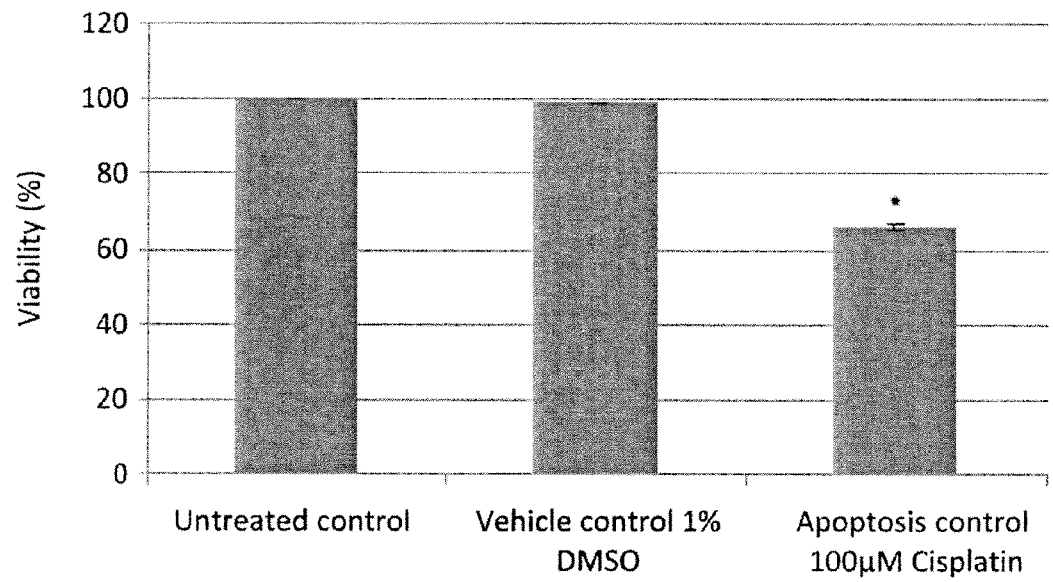
FIG. 2A: Graph depicting the percentage viability of MCF-7 cells determined by Trypan blue dye exclusion assay.
Figure 2A:
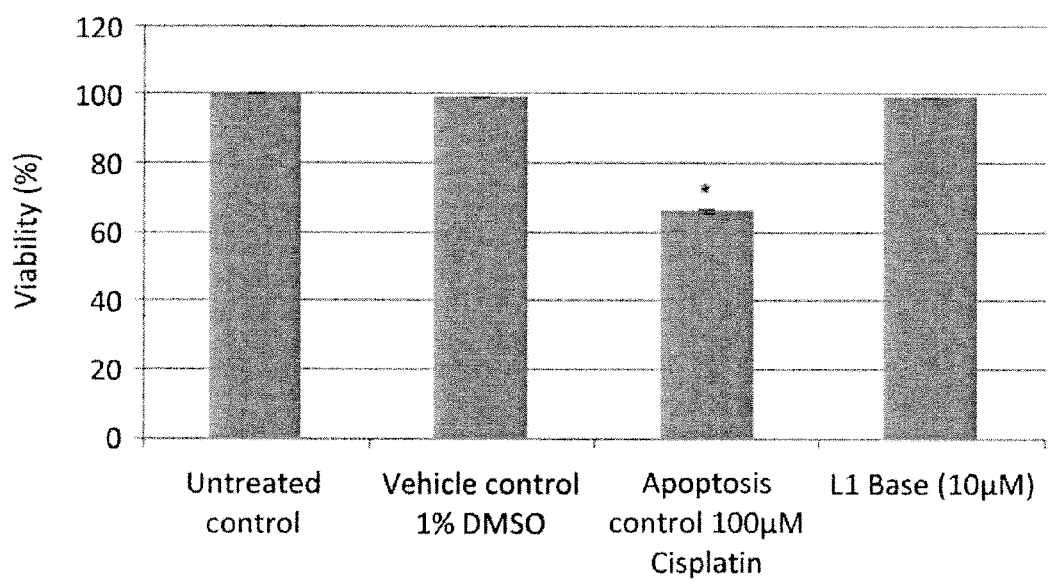

The percentage viability of MCF-7 cells determined by the Trypan blue dye exclusion assay is represented in FIG. 2A. MCF-7 cells were treated with 1% DMSO as a vehicle control as well as 100 µM Cisplatin as a positive apoptosis control. Untreated cells served as a negative control. The error bars represent the standard error of the mean (SEM n=6). A significant difference (P<0.001) between the control and the treated samples was calculated using Student's T-test and is indicated by an asterisk.

Figure 2B:
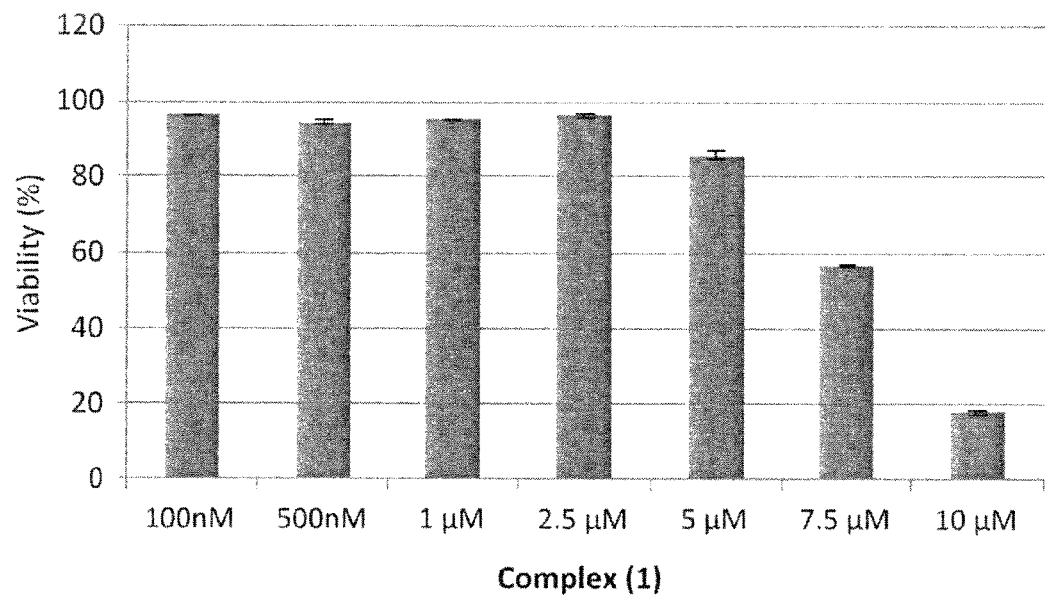
FIG. 2B: Graph depicting the dose dependant studies of complex (1) determined by Trypan blue dye exclusion assay. The error bars represent the standard error of the mean (SEM n=2)
Figure 2C:
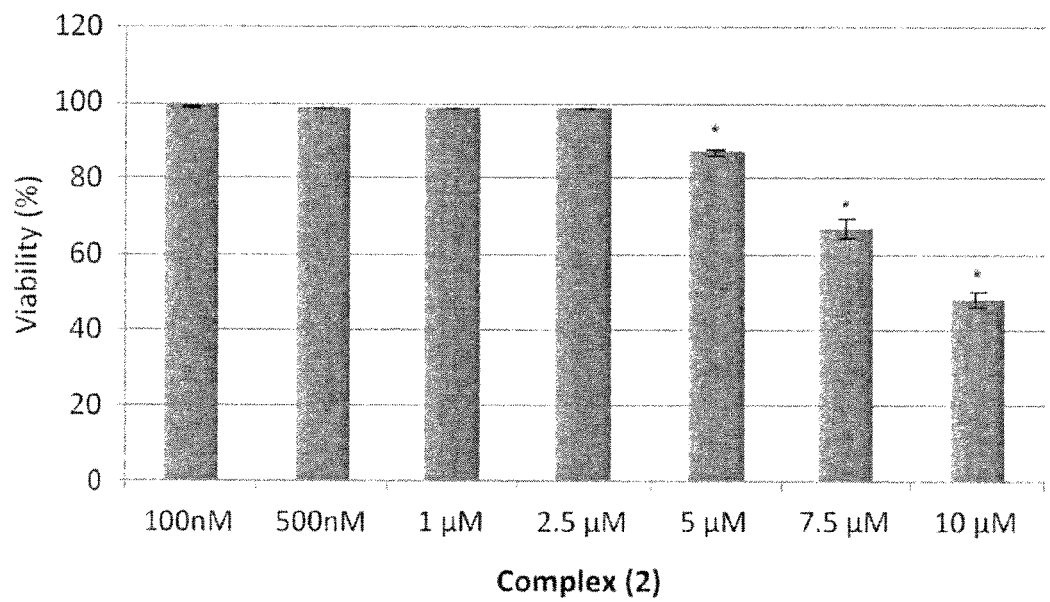
FIG. 2C: Graph depicting the dose dependant studies of complex (2) determined by Trypan blue dye exclusion assay. The error bars represent the standard error of the mean (SEM n=6)
Figure 2D:
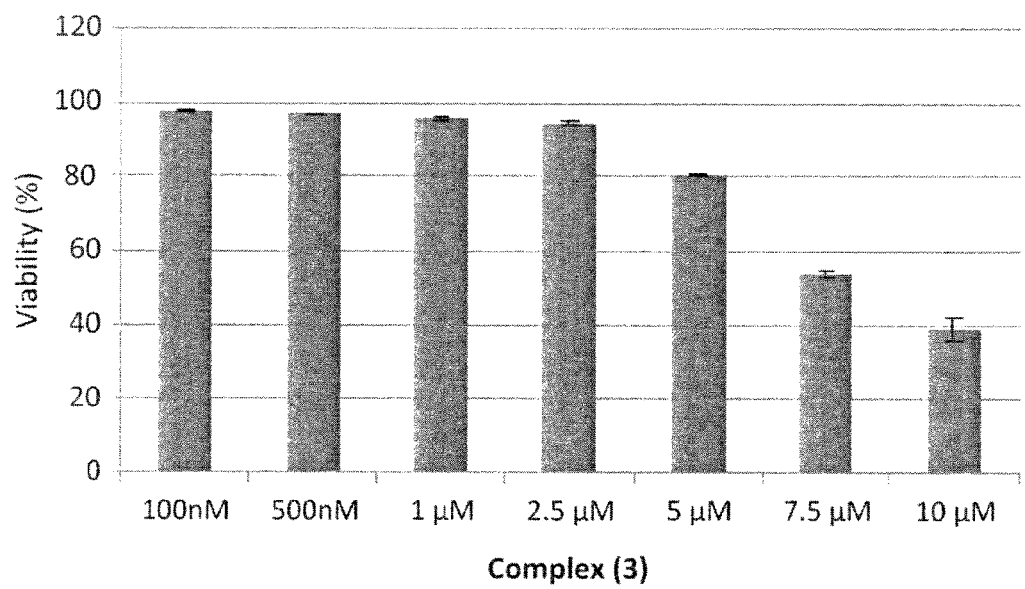
FIG. 2D: Graph depicting the dose dependant studies of complex (3) determined by Trypan blue dye exclusion assay. The error bars represent the standard error of the mean (SEM n=2)
Figure 2E:
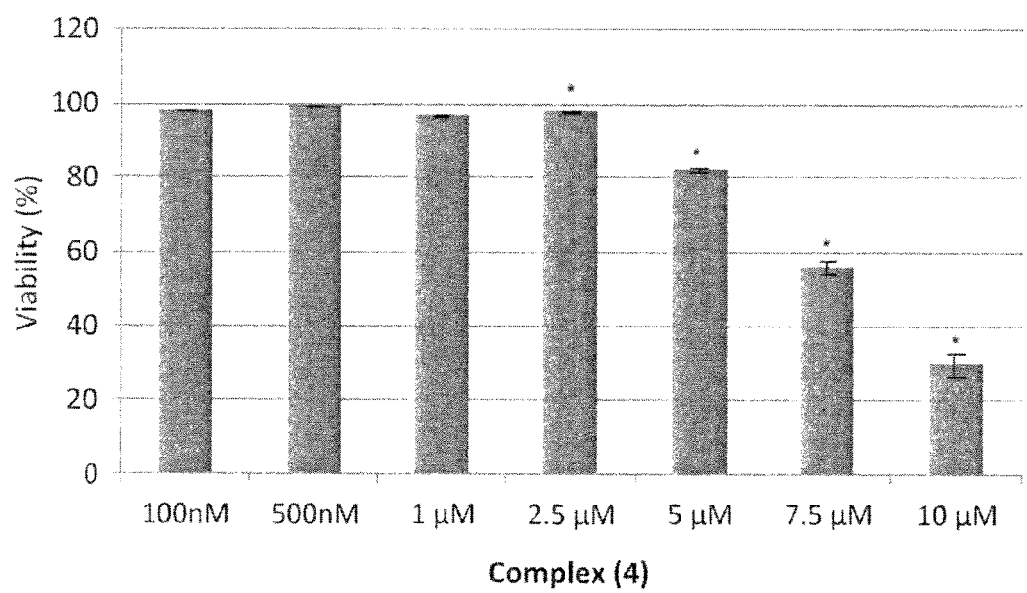
FIG. 2E: Graph depicting the dose dependant studies of complex (4) determined by Trypan blue dye exclusion assay. The error bars represent the standard error of the mean (SEM n=6)
Figure 2F:
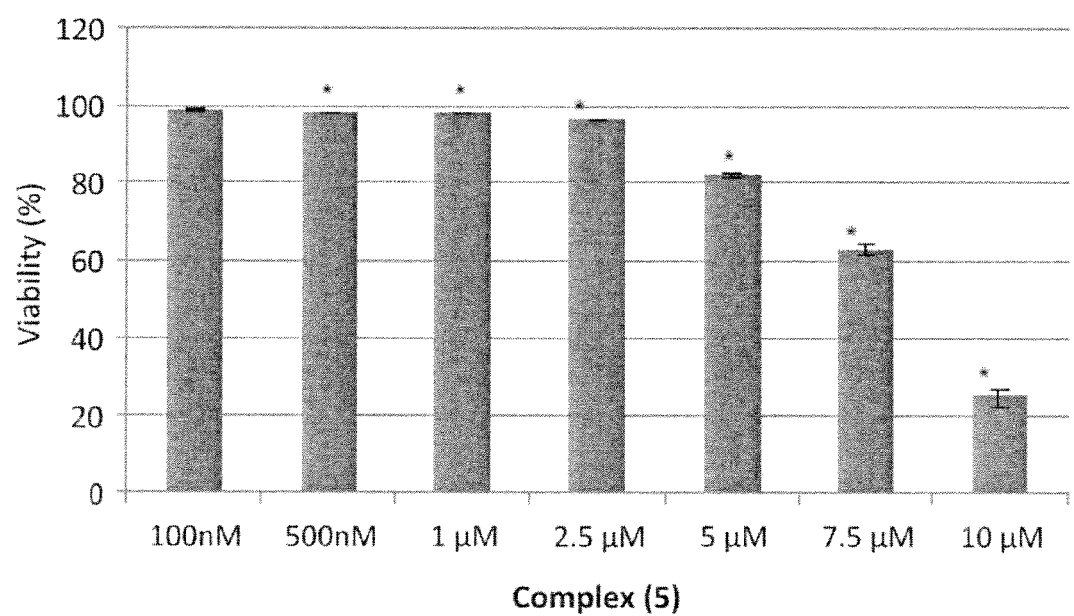
FIG. 2F: Graph depicting the dose dependant studies of complex (5) determined by Trypan blue dye exclusion assay. The error bars represent the standard error of the mean (SEM n=6)

The dose dependant studies of complex (1) are depicted in FIG. 2B. The percentage viability of MCF-7 cells was determined by the Trypan blue dye exclusion assay. MCF-7 cells were treated with different concentrations of complex (1).

FIGS. 2C to 2F show the dose dependant studies of complexes (2) to (5). In each of these Figures, the percentage viability of MCF-7 cells was determined by the Trypan blue dye exclusion assay. MCF-7 cells were treated with different concentrations of complexes (2) to (5). A significant difference (P<0.001) between the control and the treated samples was calculated using Student's T-test and is indicated by an asterisk.

Figure 3:
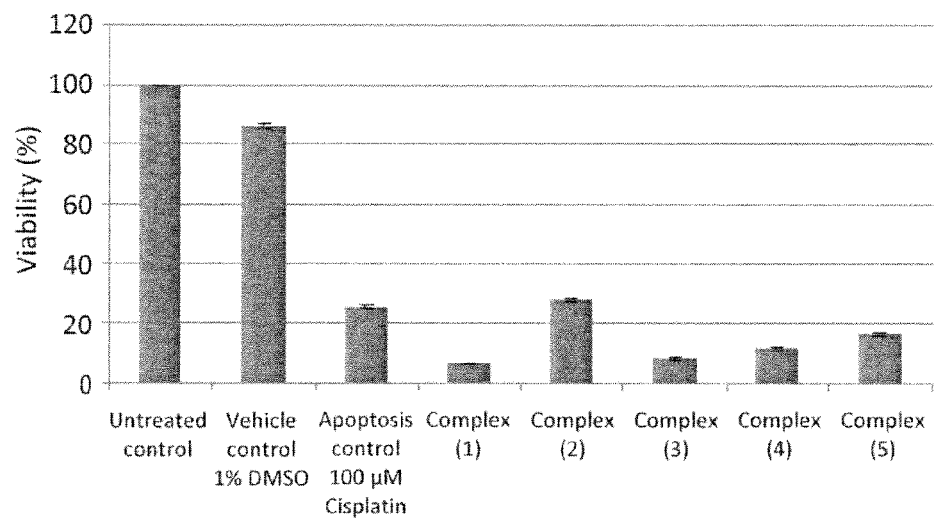
FIG. 3: Graphs depicting the percentage viability of differentially treated MCF-7 cells as determined by the AlamarBlue® viability and proliferation assay.
Figure 3:
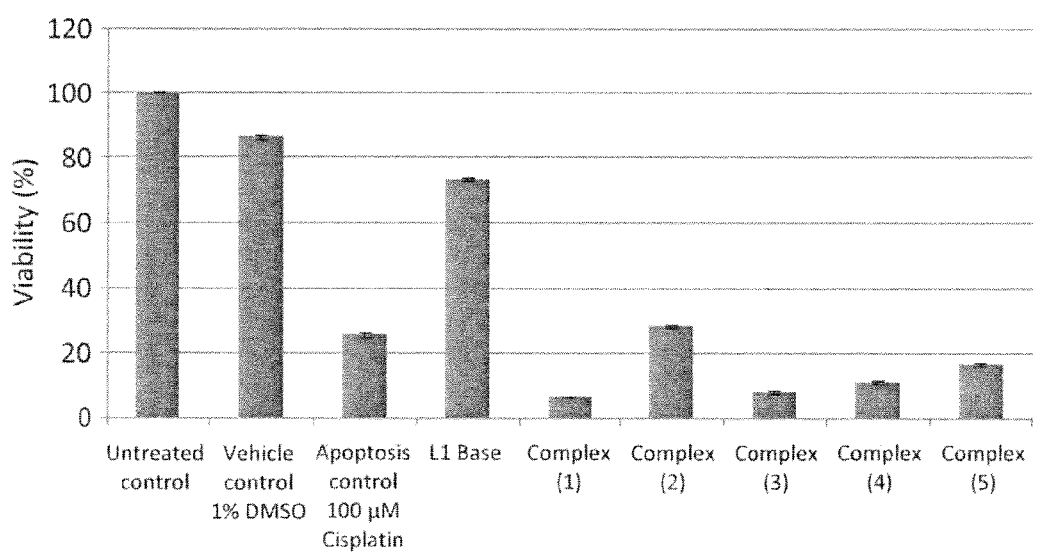

In addition hereto, the percentage viability of differentially treated MCF-7 cells as determined by the AlamarBlue® viability and proliferation assay is depicted in FIG. 3. Viability is represented as a percentage with the control at 100%. Cells were treated with various silver(I) thiocyanate phosphine complexes. Cells treated with 1% DMSO and 100 µM Cisplatin were used as a vehicle and an apoptotic control respectively. The SEM is indicated as error bars (n=9).

Figure 4:
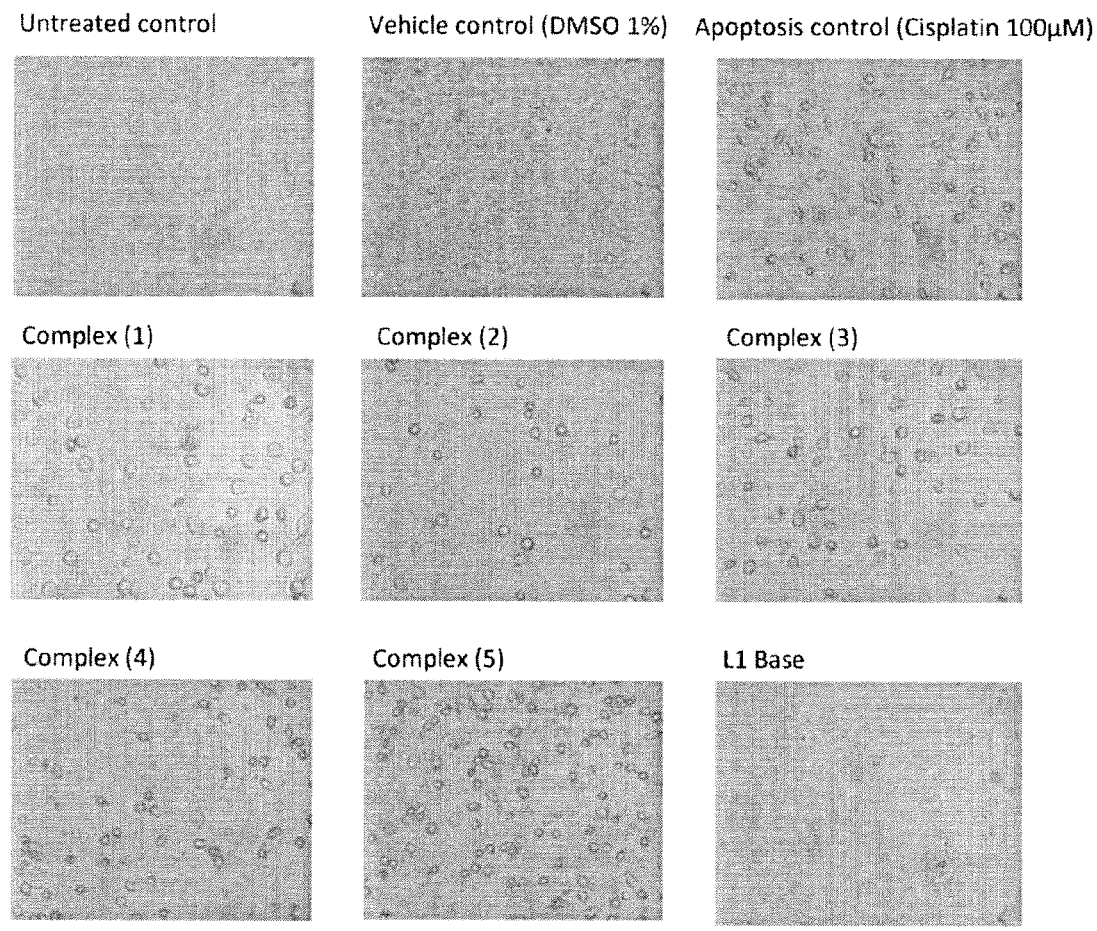
FIG. 4: Morphological features of MCF-7 cells following differential treatments as evaluated by inverse light microscopy.

Morphological Features of the MCF-7 Breast Cancer Cells Following Differential Treatments as Evaluated by Inverse Light Microscopy The morphological features of MCF-7 cells following differential treatments were evaluated by inverse light microscopy as depicted in FIG. 4. Untreated cells served as the control, while 1% DMSO served as the solvent control and 100 µM Cisplatin indicates apoptotic cells. Cells were exposed to 10 µM of complexes (1)-(5). Morphological changes of the cell indicative of apoptosis include cell shrinkage and blebbing.

Figure 5:
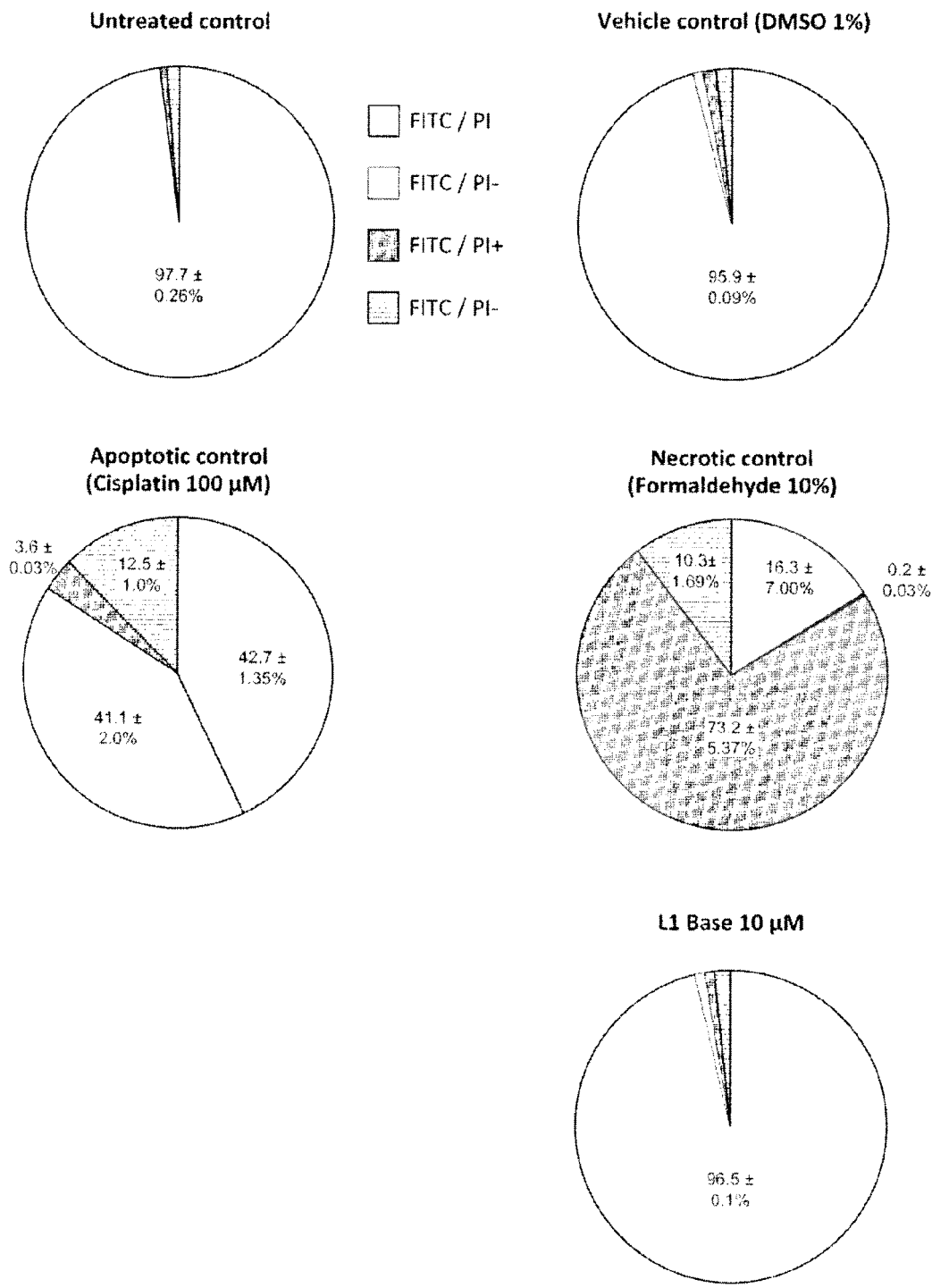
FIG. 5: Pie charts representing flow cytometric analysis to determine PS externalization and membrane integrity in differentially treated MCF-7 cells.
Figure 5:
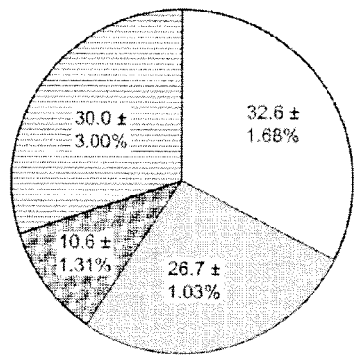
Figure 5:
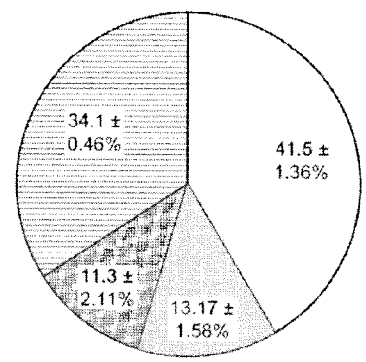
Figure 5:
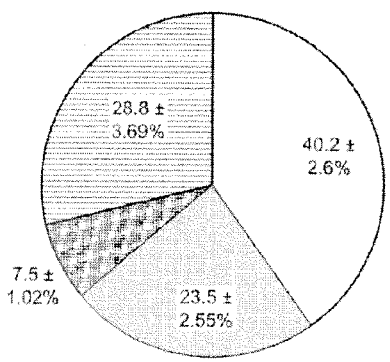
Figure 5:
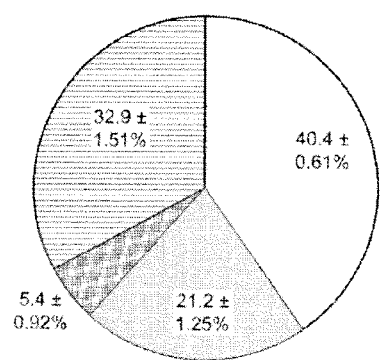
Figure 5:
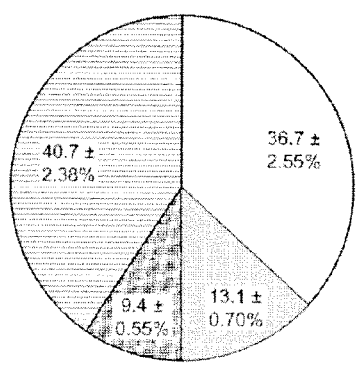
Figure 6:
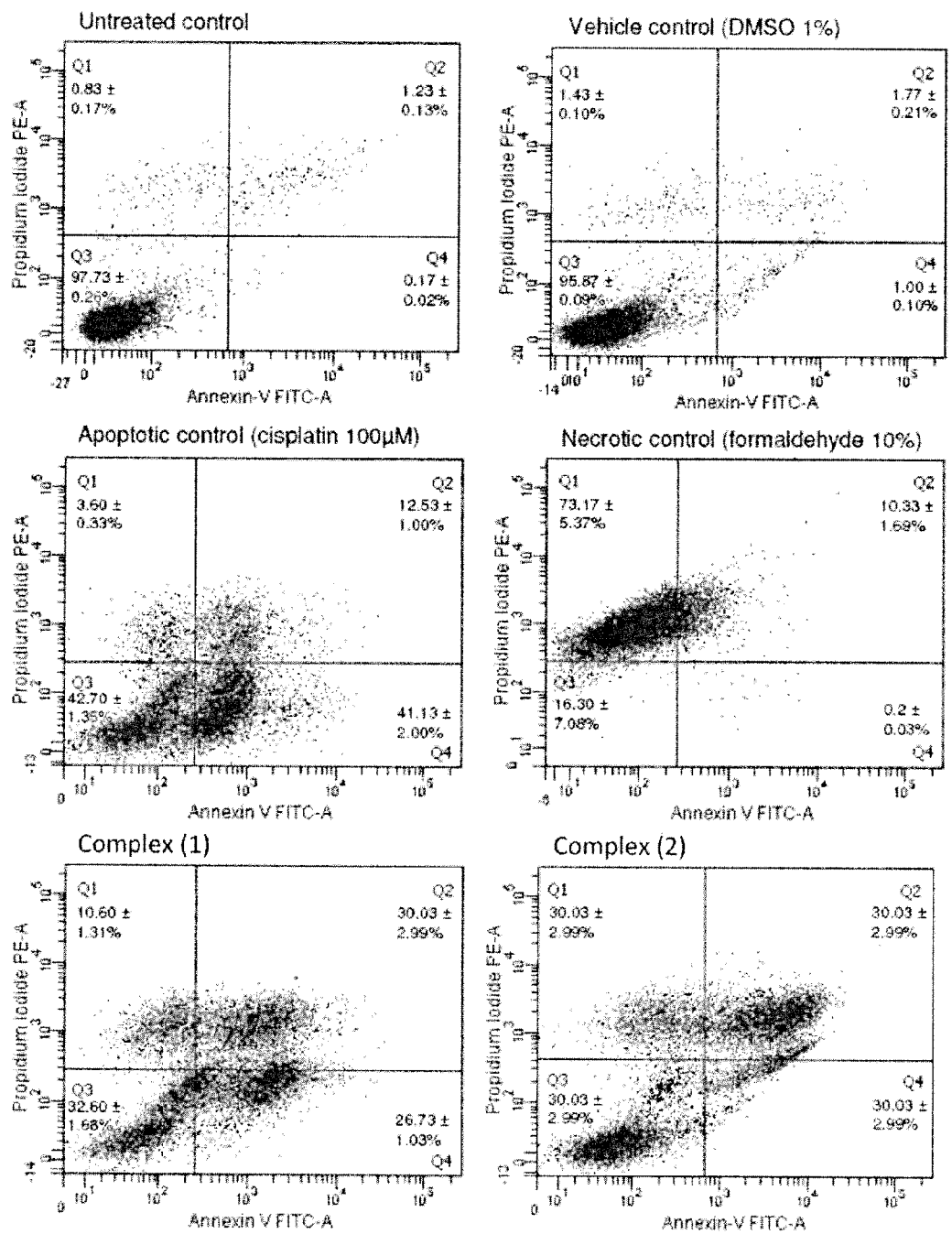
FIG. 6: Flow cytometric analysis to determine PS externalization and membrane integrity in differentially treated MCF-7 cells.
Figure 6:
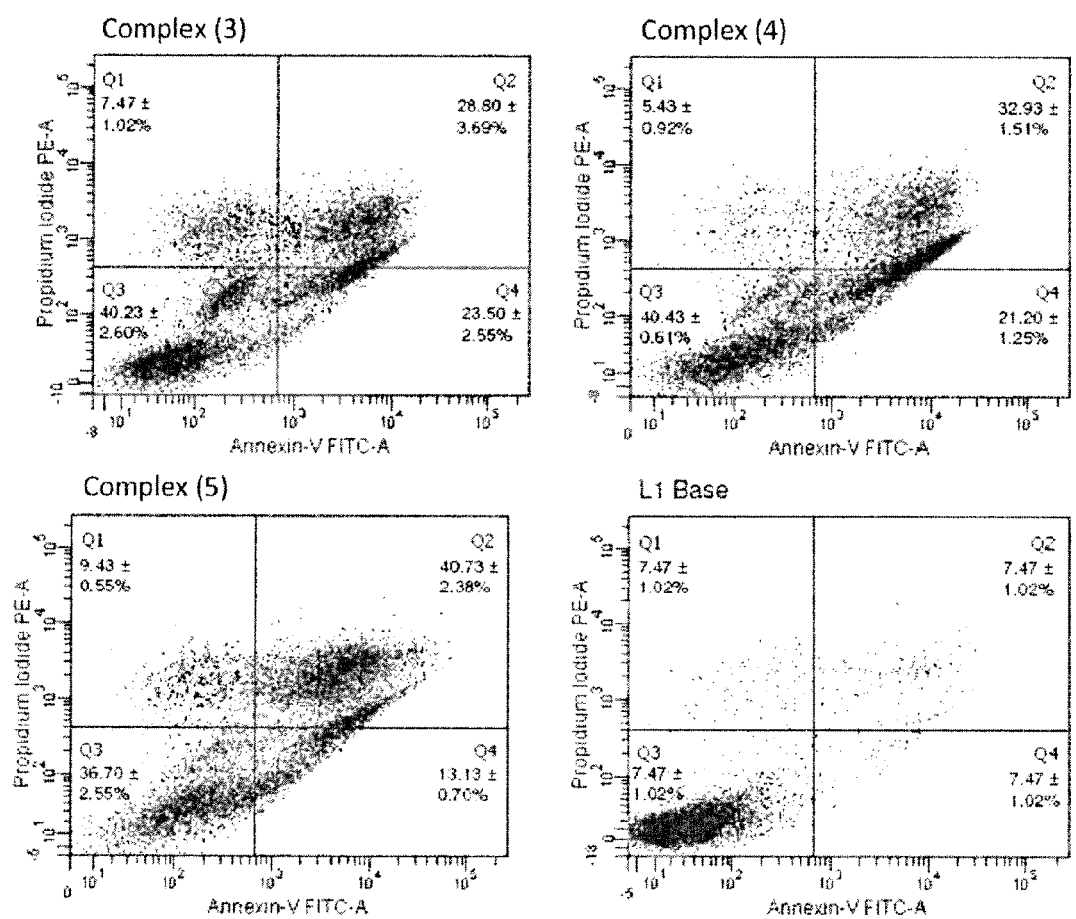

Flow Cytometric Analysis of Apoptosis and/or Necrosis for MCF-7 Breast Cancer Cells Flow cytometric analysis was conducted in order to determine PS externalization and membrane integrity in differentially treated MCF-7 cells (FIGS. 5 and 6).

Pie charts representing flow cytometric analysis to determine PS externalization and membrane integrity in differentially treated MCF-7 cells are depicted in FIG. 5. The MCF-7 cells were treated with complexes (1)-(5), 1% DMSO as a vehicle control, 100 µM Cisplatin as the apoptotic control and 10% formaldehyde as the necrotic control. Untreated cells served as a negative control.

FIG. 6 depicts flow cytometric analysis whereby the average percentages of cells in the respective quadrants are indicated as well as the SEM (n=3). Quadrant Q1 is positive for Annexin V-FITC and negative for PI. Cells in Quadrant Q2 are positive for Annexin V-FITC and PI. Quadrant Q3 cells are negative for both Annexin V-FITC and PI while cells in Quadrant Q4 are positive for PI and negative for Annexin V-FITC.

Discussion

The effects of the silver complexes of the present invention on the viability and proliferation of MCF-7 breast cancer cells were studied to determine if the complexes have cell death inducing capabilities. Cells treated with 10 µM of complex (1) or (3) showed more than a 90% decrease in viability and proliferation 24 hours after treatment when compared to the untreated control (FIG. 1A) and cells treated with 10 µM of complex (4) or (5) showed more than a 80% decrease in viability and proliferation 24 hours after treatment when compared to the untreated control. Complex (2) was the least toxic causing approximately a 70% decrease in viability.

The values obtained show strong cytotoxic activity, with complex (1), complex (3) and complex (4) being the strongest. Silver(I) bidentate pyridyl phosphine complexes have also shown in vitro cytotoxicity that strongly depends upon their lipophilicity.

In the light of the decreased viability, the morphology of the cells was studied 24 hours after treatment with 10 µM of complexes (1), (2), (3), (4) and (5) to determine if apoptotic or necrotic features were present. The morphology of the cells was compared to the apoptotic control treated with 100 µM Cisplatin (FIG. 4).

The morphology of the cells treated with the respective silver(I) complexes (1)-(5) reveal features comparable to the cells treated with the apoptotic inducer. Shrinkage of the cells, chromatin condensation as well as blebbing and formation of apoptotic bodies indicative of apoptosis were observed (FIG. 4). Cells treated with complex (1) however showed morphology characteristic of necrosis such as gain in cell volume and loss of intracellular contents (Kroemer et al., 2009). It is known that Cisplatin damage to DNA stimulates apoptosis via a p53-dependent pathway and Rackham et al. (2007) observed that the gold complex, [Au(d2-pypp)$_2$]Cl, at submicromolar concentrations induces apoptosis in breast cancer cells via the mitochondrial pathway.

4.2 SNO-Oesophageal Cancer Cell Assays

The AlamarBlue® Viability and Proliferation Assay of SNO-Oesophageal Cancer Cells An AlamarBlue® viability (Serotec, UK) assay was performed after a 24 hour treatment with complexes (1)-(5) and their ligands (Ligand-1 to Ligand-5, respectively) to evaluate the cellular effect the instant complexes (and their ligands) may have on the cancer cells. AlamarBlue® dye (10%) was incubated with trypsinized cells over a 2 hour period before the fluorescence was measured with a Synergy HT Multi-Detection Microplate reader (BioTek, Winooski, Vt.) at wavelengths of 530 nm and (excitation) and 590 nm (emission). This fluorescent based assay in particular involves the metabolic oxidation-reduction reaction of resazurin to a reduced resorufin product that is directly proportional to the amount of viable cells.

Figure 7:
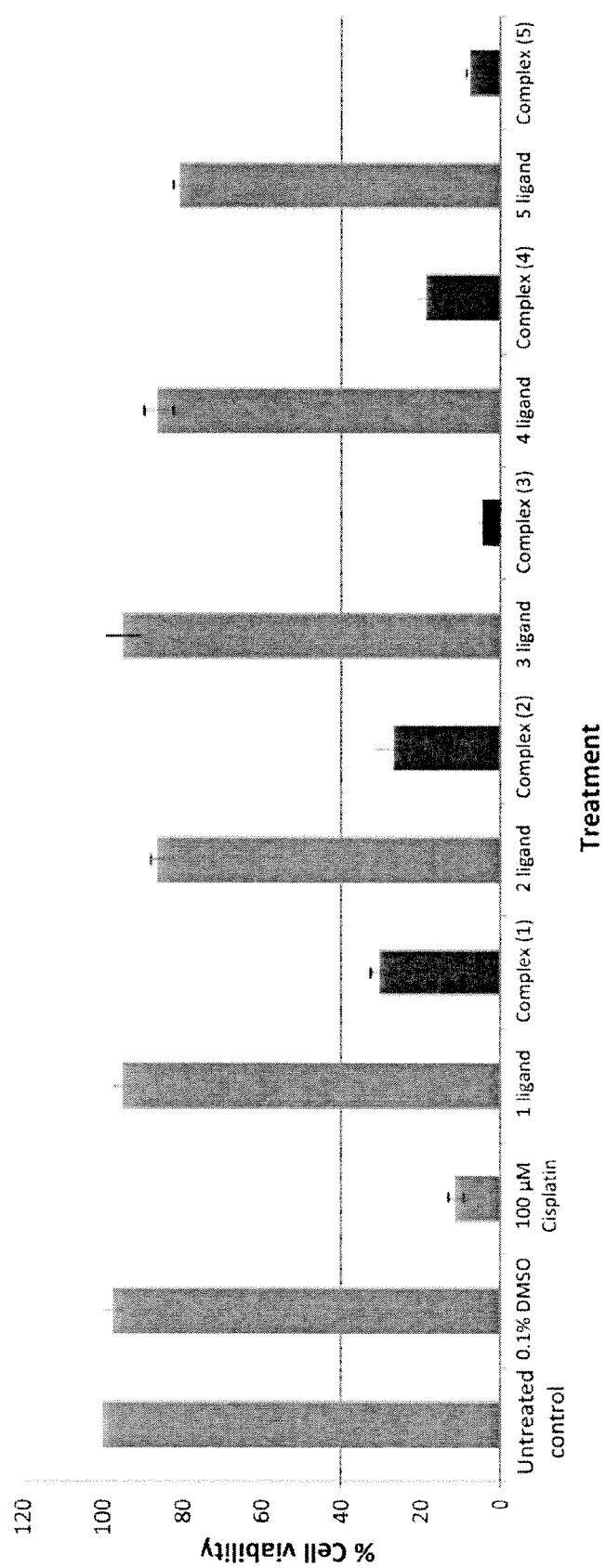
FIG. 7: Graph depicting the percentage cellular viability of differentially treated SNO-oesophageal cells, determined using an AlamarBlue® assay.

The percentage cellular viability of differentially treated SNO-oesophageal cells was determined using an AlamarBlue® assay, as depicted in FIG. 7. Different controls (grey)

were included: untreated, 0.1% DMSO solvent and apoptotic control (100 µM Cisplatin) as well as the corresponding ligands (10 µM) of complexes (1)-(5). Cells were treated with silver(I) thiocyanate phosphine complexes (1)-(5) at a concentration of 10 µM. The percentages were calculated with respect to the control and error bars were constructed on the basis of Standard Error of the Mean (SEM) where n=9 except for the ligand of compound 4 (n=8). The P-values (*P<0.001 and **P<0.0001) were determined with the Student's T-test to evaluate the significant difference.

Morphological Features of the SNO-Oesophageal Cancer Cells Following Differential Treatments as Evaluated by Inverse Light Microscopy Morphological studies were done by means of an Axiovert 25 inverted microscope (Carl Zeiss, Göttingen, Germany) with Axio Vision 3.1 software (Carl Zeiss, Göttingen, Germany) using an magnification of 100×. After 24 hours of treatment with complexes (1)-(5) including their ligands the cells were examined under said Axiovert 25 inverted light microscope. This was done to determine how the complexes of the present invention influence morphology which was compared to 100 µM Cisplatin (apoptotic control) and 15% $H_2O_2$ (necrotic control). These results would indicate whether apoptosis or necrosis was induced in the cells by complexes (1)-(5) of the present invention.

Figure 8:
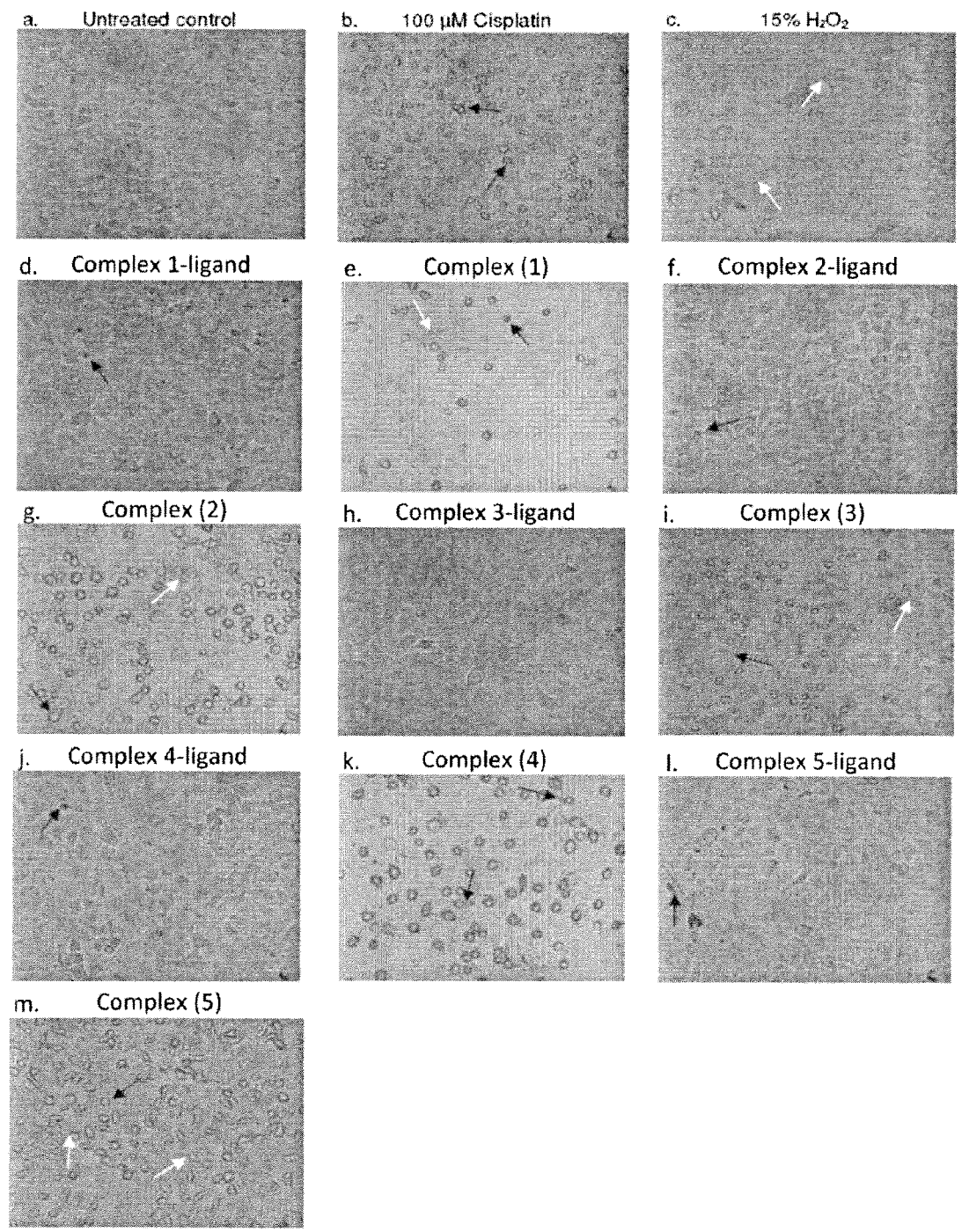
FIG. 8: Light microscope images indicating the morphology of the differentially treated SNO-oesophageal cancer cells.

Light microscope images indicating the morphology of the differentially treated SNO-oesophageal cancer cells is shown in FIG. 8. An untreated control (a) including 100 µM Cisplatin (b), an apoptotic control and 15% $H_2O_2$ (c), and a necrotic control was included. Cells were treated with 10 µM silver(I) thiocyanate phosphine complexes (1)-(5) as well as their separate ligands (Ligand-1 to Ligand-5, respectively) (FIGS. 8*d* to 8*m*). Black arrows represent signs of apoptosis, while the white arrows represent signs of necrosis.

Flow Cytometric Analysis of Apoptosis and/or Necrosis for SNO-Oesophageal Cancer Cells After the 24 hour treatment period the cells were analysed by means of flow cytometry to confirm if the cells had undergone apoptosis or necrosis.

To determine if either apoptosis or necrosis occurred, the cells were double labelled with Annexin-V FITC and Propidium Iodide (PI) by means of an Annexin-V FITC assay kit (Serotec, UK). This was done according to manufacturer's instructions with a few adjustments. Briefly, the cells ($\pm 3 \times 10^5$ cells/ml) were washed twice with cold phosphate buffered saline (PBS), followed by the addition of 100 µl 1× binding buffer. Two and a half microliters of Annexin-V along with 5 µl PI were added in the dark and was incubated for 15 minutes at room temperature. After incubation, 400 µl 1× binding buffer was added and cells were analysed using the FACSAria flow cytometer (BD Biosciences, San Jose, Calif.) with FACSDiva software (BD Biosciences, San Jose, Calif.) 492 nm (excitation) and 520 nm for Annexin and 488 nm and 575 nm (emission) for PI.

The cell membrane contains a negatively charged phosphatidylserine (PS) on the inner leaflet and is exposed when apoptosis or necrosis takes place. Annex n-V interacts with PS in both apoptotic and necrotic cells, making these cellular deaths undistinguishable. This is overcome by using PI as an alternative label that interacts with the exposed DNA of necrotic cells only, leading to the fluorescent detection of both these labels. Pie charts (FIG. 9) were constructed for all the controls (including Ligand-1 to Ligand-5) and the different silver(I) thiocyanate phosphine complexes (1)-(5).

Figure 9:
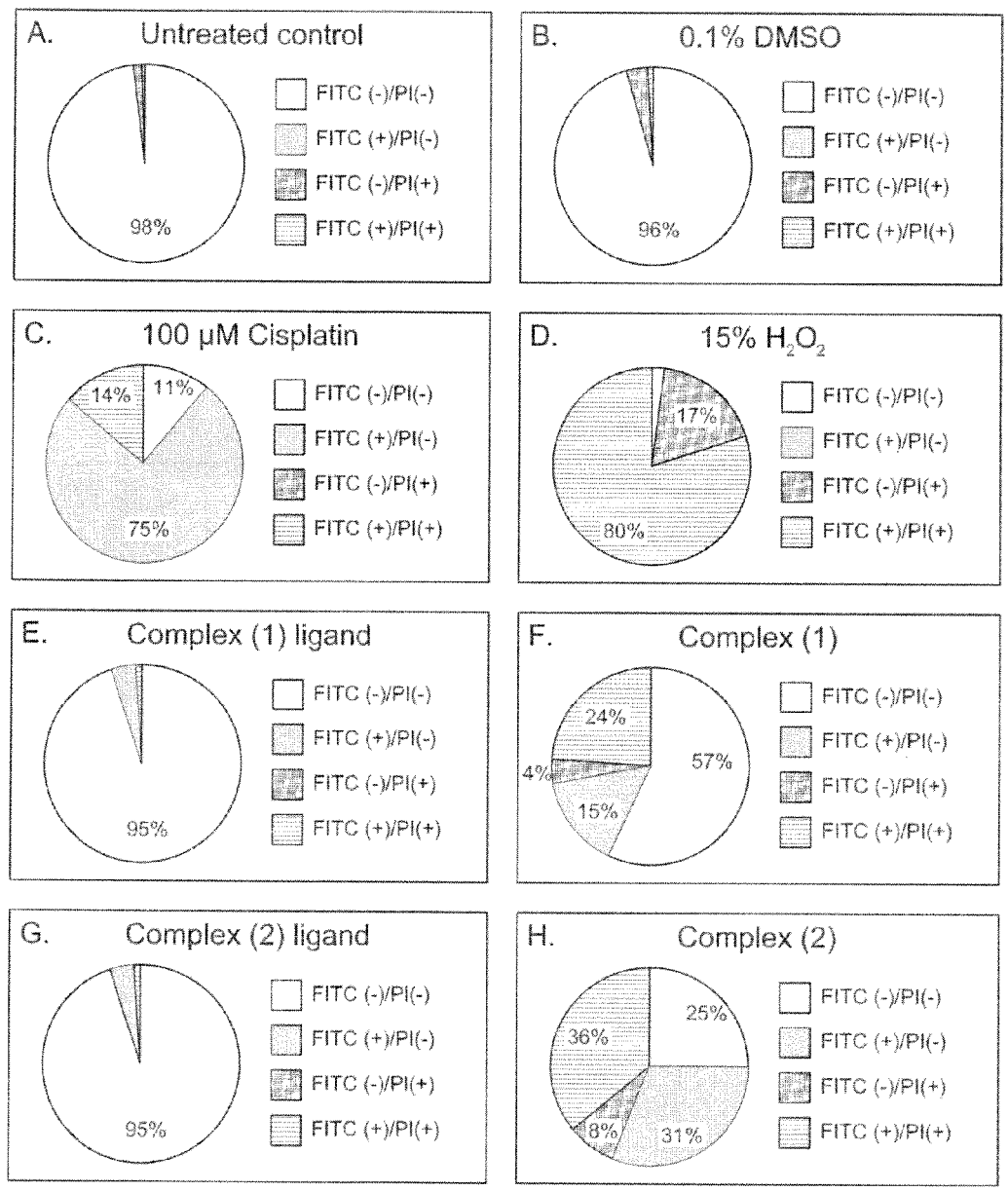
FIG. 9: Pie charts representing the four different flow cytometric quadrants of Annexin-V and FITC to determine the mode of cellular death induced in differentially treated SNO-oesophageal cells.
Figure 9:
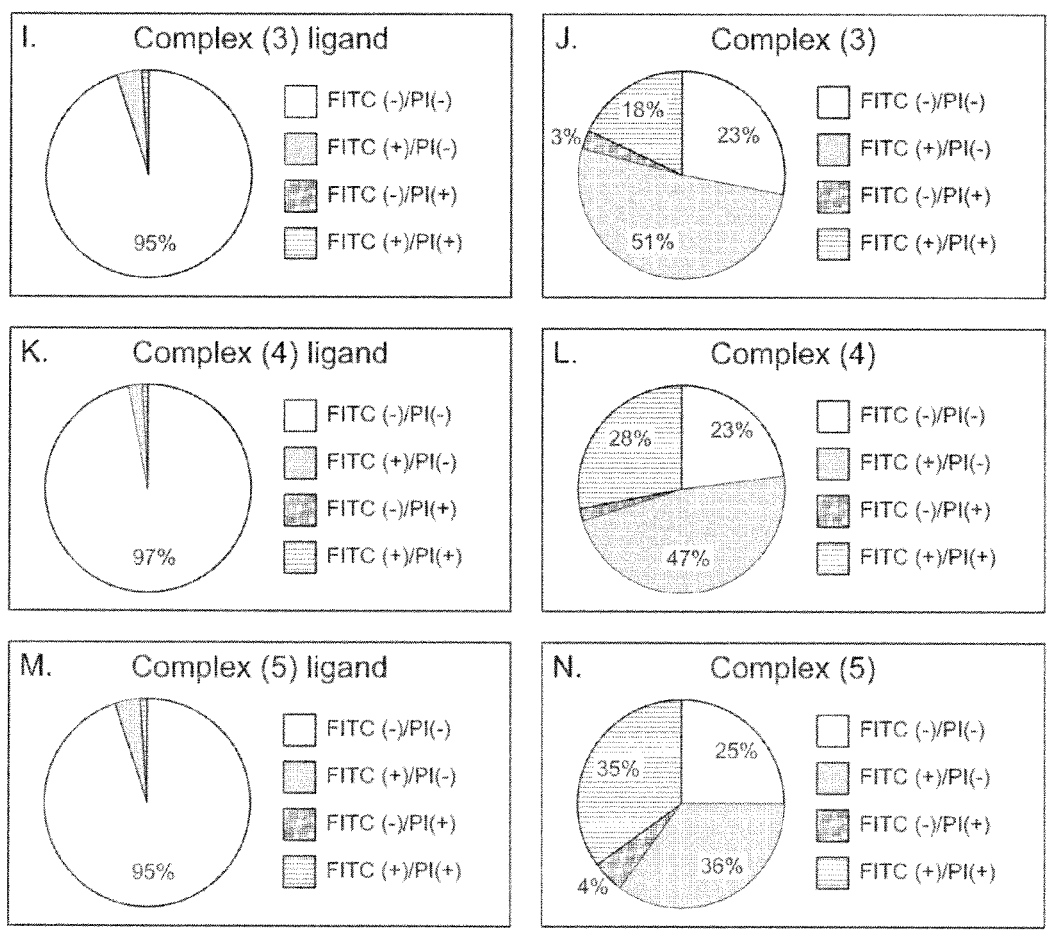

Pie charts representing the four different flow cytometric quadrants of Annexin-V and FITC to determine the mode of cellular death induced in differentially treated SNO-oesophageal cells are represented in FIG. 9. An untreated control (A), apoptotic control (B) and necrotic control (C) were included. Cells were treated with 10 µM of the different ligands including the silver(I) thiocyanate phosphine complexes (1)-(5). An average percentage was calculated for all segments where the SEM is n=3 for all treatments except for 15% $H_2O_2$ (n=2). The four segments represent the following: White segment—negative for FITC and PI, Light grey segment—positive for FITC but negative for PI, Dark grey segment—positive for PI but negative for FITC and Black segment—positive for both FITC and PI. Cells undergoing early apoptosis are represented by the light grey segment, while those of late apoptosis and primary necrosis are represented by the black segment. Necrotic cells are represented by the dark grey segment and intact viable cells are shown by the white segment.

Statistical Analysis

Data represented were expressed as the Standard Error of Mean (SEM) where at least 3 biological and 3 technical repeats were used. The Student's T-test was used to calculate the significant difference (*P<0.05 and P<0.001) of the treatments with respect to the untreated control except in the flow cytometric data.

Discussion

The effects of the silver (I) complexes (1)-(5) on the viability and proliferation of SNO-oesophageal cancer cells were studied to determine if the compounds have cell death inducing capabilities.

The various 10 µM silver(I) thiocyanate phosphine complexes (1)-(5) significantly (P<0.0001) decreased the percentage cellular viability when compared to the control. Complexes (3) and (5) appear to be highly toxic to the SNO-oesophageal cells followed by complexes (4), (2) and (1). The ligands of complexes (1)-(5) where included to evaluate their effects on the SNO-oesophageal cells in the absence of AgSCN and to determine if the same phenomena occurred as when the AgSCN main backbone is present.

Surprisingly the cells' viability ranged from 95-79% indicating the ligands low toxicity. Although the ligands of complexes (2) and (5) significantly decreased (P<0.001) the viability to 86.4% and 80.7% respectively it seems that the whole silver(I)thiocyanate phosphine complex (attached to its ligand) is required to induce cancer cell death. This is contradictory to Baguley et al. (2008) findings where the 2-pyridyl and 4-pyridyl ligands had similar toxicities in a range of ovarian cancer cells, than the entire silver or gold bidentate phosphine compounds. Complexes (1)-(5) and their ligands where dissolved in 0.1% DMSO that decreased the percentage viability with approximately 2.2% signifying its minimal influence in cancer cell growth.

As can be observed from the light microscope images indicating the morphology of the differentially treated SNO-oesophageal cancer cells (FIG. 8), the control cells are intact with no signs of cellular death, but when compared to complexes (1)-(5) multiple signs of apoptosis that involve blebbing and apoptotic body formation (as shown by the black arrow) can be seen. Necrotic cell death was also observed in complexes (1), (2), (3) and (5) (as shown by the white arrow) that resulted in the release of cellular content from the SNO-oesophageal cells. Cells that were treated with the respective ligands on the other hand showed no (Ligand-3) or minimal (Ligand-1, Ligand-2, Ligand-4 and Ligand-5) signs of apoptosis while necrosis was absent. Their morphology correlated with that of the control signifying their minimal influence in cancer cell growth.

As shown by the flow cytomtric analysis depicted in FIG. 9, the untreated control had minimal cell death consisting of an average viability of 98.2%. This was similar to the 0.1% DMSO solvent control and the respective ligands (Ligand-1 to Ligand-5) ranging from 96-95%. Although cellular death did occur as seen by externalization of phosphatidylserine in Quadrant Q1, Q2 and Q4 it did not influence the cells to a large extent. On the contrary apoptosis and necrosis was induced in the SNO-oesophageal cells treated with the different silver complexes (1)-(5) but early apoptosis was more apparent. Complex (1) toxicity was lower when compared to complexes (2)-(5) and ±57.47% cells were still viable where the other cells were in the stages of early apoptosis or necrosis. Complex (3) on the other hand induced apoptosis in more than half of the cancer cells although approximately 28% survived. This was followed by complexes (4), (5), (2) and (1). The necrotic control 15% $H_2O_2$ should be in Q1 but as seen from FIG. 9 the cells form a tight population and are destined for necrosis. In order to ensure that the whole population shifts into Q1, the concentration will be increased.

5. The Toxicity Effects of Complexes (1)-(5) on a Non-Cancerous Cell Line

To evaluate the relative toxicity on non-tumorigenic tissues, the ideal is to compare the effect of the compounds to a similar cell line that is non-cancerous. The Applicant is currently in the process of purchasing these cell lines and will evaluate the toxicity of the compounds in the near future. However, the Applicant did evaluate the effect of the complexes of the instant invention on peripheral blood mononucleocytes (PBMCs) isolated from fresh whole blood samples from a healthy donor. This already gives a good indication of the potential toxicity of complexes (1)-(5) in an in vivo environment.

Figure 10:
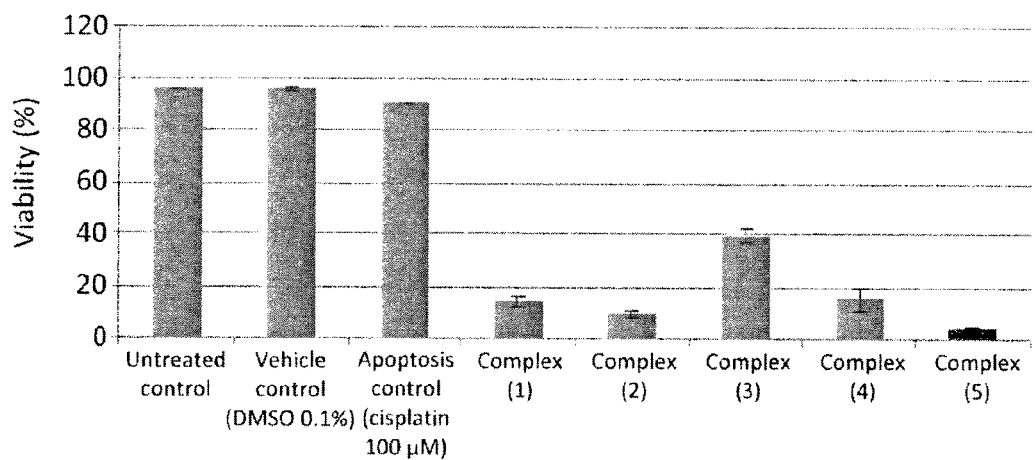
FIG. 10: Graph depicting the percentage viability of differentially treated PBMCs (peripheral blood mononucleocytes) as determined by the Trypan blue viability assay.

The percentage viability of differentially treated PBMCs (peripheral blood mononucleocytes) for complexes (1)-(5) was determined by the Trypan blue viability assay, as shown in FIG. 10. Cells were treated with complexes (1)-(5), Cells treated with 0.1% DMSO and 100 µM Cisplatin were used as a vehicle and apoptotic control respectively. The SEM is indicated as error bars (n=2). Although a varying extent of decrease in viability was observed with complexes (1)-(5), complex (3) indicated a much lower degree of toxicity than the other complexes. Furthermore, this specific complex showed to be the most lethal to both the MCF-7 and SNO-oesophageal cancer cells.

6. Conclusion

The Applicant has found that both the MCF-7 breast cancer cells and SNO-oesophageal cancer cells that were treated with the silver(I) thiocyanate phosphine complexes (1)-(5) of the present invention revealed a significant degree of induction of apoptosis, and to a certain extent, necrosis. When comparing the relative dosages used in comparison to the known chemotherapeutic drug, Cisplatin, the effective dosages inducing cell death are 10 times more effective. The PBMCs, used as a control non-tumorigenic reference, showed a lesser degree of induced cell death, and in the case of complex (3), a significantly lower degree of toxicity.

B: Silver(I) Nitrate Triphenylphosphine Complexes of the Invention and the Toxicity Evaluation Thereof on SNO-Oesophageal Cancer Cells 1. General Silver nitrate, triphenylphosphine, acetonitrile and ethanol, were obtained from Sigma-Aldrich. Infrared spectra were recorded on a Bruker Tensor 27 FT-IR spectrophotometer, using a Pike Golden Gate ATR accessory. $^1$H NMR (400 MHz) and $^{13}$C NMR (75 MHz) spectra were recorded on a BrukerAvance III 400 MHz spectrometer, using tetramethylsilane as an internal standard. Melting points were recorded on a Stuart Scientific Melting Point apparatus SMP10, and are uncorrected.

For the biological studies. SNO-oesophageal cancer cells were gifted by the University of Pretoria, RSA. Dulbecco's modified Eagles media (DMEM), Foetal Bovine Serum (FBS), antibiotic supplements were all purchased from Highveld Biological (Kelvin, RSA). Cell culture graded dimetyl sulpoxide (DMSO) were obtained from AppliChem (Darmstad, Germany). Cisplatin (CDDP) was purchased from Molekula (Dorset, UK) while hydrogen peroxide ($H_2O_2$) was purchased from Minema (Gauteng, RSA). AlamarBlue® dye and the Annexin-V FITC assay kit were obtained from Serotec (Oxford, UK). The CaspaseGlo® 3/7 assay was purchased Promega. All reagents were used as supplied.

2. Synthesis of Complexes

Preparation of Silver(I) Nitrate Triphenylphosphine Complexes of the Invention

Silver(I) nitrate triphenylphosphine complexes, referred to herein as complexes (6), (7), (8), (9), were prepared according to literature procedures. Microanalysis was performed by Mr. K. S. Mothwa in the Department of Chemical Technology, University of Johannesburg, RSA on a Thermo Flash 2000 series CHNS/O, Organic Elemental Analyser.

Example 1

AgNO$_3$(PPh$_3$) Complex (6)

AgNO$_3$ (0.60 g, 3.5 mmol) was added to a solution of PPh$_3$ (0.93 g, 3.5 mmol) in acetonitrile (50 cm$^3$). The mixture was heated under reflux until all the reagents dissolved. The solution was filtered while hot, and the solvent was reduced to 20 cm$^3$. The solution was allowed to cool to room temperature, after which colorless crystals were obtained. Yield: 61%; mp 174° C; IR: $v_{max}$/cm$^{-1}$: 1375, 1302, 1042, 812. $^1$H NMR: (400 MHz, CDCl$_3$): δ (ppm) 7.53 (t, $\delta_1$=7.542, $\delta_2$=7.525, $\delta_3$=7.511 $^1$J=6.2 Hz), 7.43 (t, $\delta_1$=7.457, $\delta_2$=7.429, $\delta_3$=7.411 $^1$J=9.2 Hz). $^{13}$C{H} NMR: (100 MHz, CDCl$_3$): δ (ppm) 133.4 (d, $\delta_1$=133.53, $\delta_2$=133.36, $^1$J(C—P)=12.7 Hz), 131.38, 131.0 (d, $\delta_1$=131.06, $\delta_2$=131.01, $^1$J=3.8 Hz), 129.3 (d, $\delta_1$=129.37, $\delta_2$=129.27, $^1$J=7.5 Hz). $^{31}$P(H) NMR: (161 MHz, CDCl$_3$): δ (ppm) 11.1 (d, $\delta_1$=13.24, $\delta_2$=9.03, $^1$J(P—Ag)=677.81 Hz). Elemental Analysis: (Anal. Calcd. For C$_{18}$H$_{15}$PAgNO$_3$: C, 50.03; H, 3.50; N, 3.24. Found: C, 50.12; H, 3.47; N, 2.48).

Example 2

AgNO$_3$(PPh$_3$)$_2$ Complex (7)

AgNO$_3$ (0.30 g, 1.7 mmol) was added to a solution of PPh$_3$ (0.93 g, 3.5 mmol) in acetonitrile (50 cm$^3$). The mixture was heated under reflux until all the reagents dissolved. The solution was filtered while hot, and the solvent was reduced to 20 cm$^3$. The solution was allowed to cool to room temperature, after which colourless crystals were obtained. Yield: 54%; mp 220° C.; IR: $v_{max}$/cm$^{-1}$: 1397, 1291, 1029, 817. $^1$H NMR: (400 MHz, CDCl$_3$): δ (ppm) 7.52 (t, $\delta_1$=7.539, $\delta_2$=7.521, $\delta_3$=7.503 $^1$J=7.2 Hz), 7.43 (t, $\delta_1$=7.448, $\delta_2$=7.430, $\delta_3$=7.411 $^1$J=7.4 Hz), 7.35 (t, $\delta_1$=7.369, $\delta_2$=7.345, $\delta_3$=7.325 $^1$J=8.8 Hz). $^{13}$C{H} NMR: (100 MHz, CDCl$_3$): δ (ppm) 133.5 (d, $\delta_1$=133.59, $\delta_2$=133.43, $^1$J(C—P)=12.0 Hz), 131.55, 131.27, 130.96, 129.3 (d, $\delta_1$=129.34, $\delta_2$=129.26, $^1$J=6.0 Hz). $^{31}$/P{H} NMR: (161 MHz, CDCl$_3$): δ (ppm) 8.9. Elemental Analysis: (Anal.

Calcd. For $C_{36}H_{30}P_2AgNO_3$: C, 62.26; H, 4.35; N, 2.02. Found: C, 62.22; H, 4.35; N, 1.20).

Example 3

AgNO₃(PPh₃)₃ Complex (8)

$AgNO_3$ (0.20 g, 1.17 mmol) was added to a solution of $PPh_3$ (0.93 g, 3.5 mmol) in acetonitrile (50 cm³). The mixture was heated under reflux until all the reagents dissolved. The solution was filtered while hot, and the solvent was concentrated to 20 cm³. The solution was allowed to cool to room temperature, after which colourless crystals were obtained. Yield: 72%; mp 233° C.; IR: $v_{max}$/cm⁻¹: 1382, 1308, 1027, 824. ¹H NMR: (400 MHz, CDCl₃): δ (ppm) 7.45 (t, $δ_1$=7.472, $δ_2$=7.454, $δ_3$=7.436 ¹J=7.2 Hz), 7.30 (t, $δ_1$=7.318, $δ_2$=7.300, $δ_3$=7.281 ¹J=7.4 Hz), 7.17 (t, $δ_1$=7.192, $δ_2$=7.168, $δ_3$=7.147 ¹J=9 Hz). ¹³C{H} NMR: (100 MHz, CDCl₃): δ (ppm) 133.3 (d, $δ_1$=133.36, $δ_2$=133.20, ¹J(C—P)=12.0 Hz), 132.18, 131.98, 130.47, 129.0 (d, $δ_1$=129.07, $δ_2$=128.98, ¹J=6.8 Hz). ³¹P{H} NMR: (161 MHz, CDCl₃): δ (ppm) 6.41. Elemental Analysis: (Anal. Calcd. For $C_{54}H_{45}P_3AgNO_3$: C, 67.79; H, 4.74; N, 1.46. Found: C, 67.83; H, 4.73; N, 0.68).

Example 4

AgNO₃(PPh₃)₄ Complex (9)

A solution of $AgNO_3$ (0.25 g, 1.5 mmol) in acetonitrile (5 cm³) was added to a solution of $PPh_3$ (1.93 g, 7.5 mmol) in ethanol (50 cm³). The mixture was heated under reflux for 24 hours. The solution was filtered while hot, and the solvent was concentrated to 20 cm³. The solution was allowed to cool to room temperature, after which colourless crystals were obtained. Yield: 73%; mp 225° C. IR: $v_{max}$/cm⁻¹: 1338, 829. ¹H NMR: (400 MHz, CDCl₃): δ (ppm) 7.43 (t, $δ_1$=7.445, $δ_2$=7.426, $δ_3$=7.408 ¹J=7.4 Hz), 7.27 (t, $δ_1$=7.292, $δ_2$=7.274, $δ_3$=7.255 ¹J=7.4 Hz), 7.13 (t, $δ_1$=7.149, $δ_2$=7.127, $δ_3$=7.106 ¹J=8.6 Hz). ¹³C{H} NMR: (100 MHz, CDCl₃): δ (ppm) 133.2 (d, $δ_1$=133.31, $δ_2$=132.82, ¹J(C—P)=12.8 Hz), 132.96, 132.82, 130.16, 128.9 (d, $δ_1$=128.98, $δ_2$=128.89, ¹J=6.8 Hz). ³¹P{H} NMR: (161 MHz, CDCl₃): δ (ppm): 3.9 (s) Elemental Analysis: (Anal. Calcd. For $C_{72}H_{60}P_4AgNO_3$: C, 70.94; H, 4.96; N, 1.15. Found: C, 70.41; H, 4.81; N, 0.00)

For ease of reference, the chemical structures of complexes (6)-(9) are provided herein below.

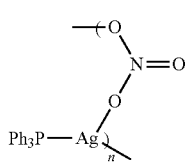

Complex (6)

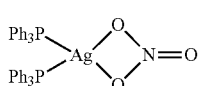

Complex (7)

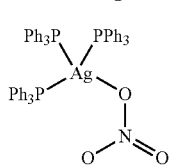

Complex (8)

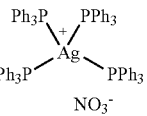

Complex (9)

TABLE 1

Infrared bands (cm⁻¹) for nitrate vibrational modes for complexes (6)-(9) where s = strong, m = medium and w = weak

| Assignment | (6) | (7) | (8) | (9) |
| --- | --- | --- | --- | --- |
| Asym N-O str. ($v_1$) | 1375 s | 1397 s | 1382 s | 1338 s |
|  | 1307 s | 1291 s | 1308 s | — |
| Sym N-O str. ($v_3$) | 1042 w | 1029 m | 1027 m | — |
| Out-of-plane def. ($v_2$) | 812 m | 817 m | 824 m | 829 w |

3. Cell Culturing and Treatment

The SNO-oesophageal cancer cells were cultured in Dulbecco's modified Eagles medium (DMEM) containing 10% Foetal bovine serum (FBS), 0.8% Penicillin/Streptomycin/Fungizone and 0.2% Gentamycin. The SNO-oesophageal cancer cells were subcultured every 48 hours and incubated at 37° C. under a 5% $CO_2$ humidified atmosphere. After 48 hours the cells were trypsinized and plated (6×10⁵ cells) in 3.5 cm culture dishes and left to cultivate for 24 hours.

The cells were thereafter treated with complexes (6)-(9) at a concentration of 10 μM prepared in 0.1% DMSO. Treatment with either 25% $H_2O_2$ or 100 μM CDDP served as controls for necrosis and apoptosis respectively. The CDDP was prepared in 0.9% NaCl while the $H_2O_2$ was diluted with supplemented DMEM prior to treatment.

Several assays were used to evaluate the effect of complexes (6)-(9) on cell death with respect to the SNO-oesophageal cancer cells. These included cell viability assays such as the AlamarBlue® viability and proliferation assay, microscopy to evaluate cell morphology and flow cytometric analysis of apoptosis and/or necrosis.

Figure 12:
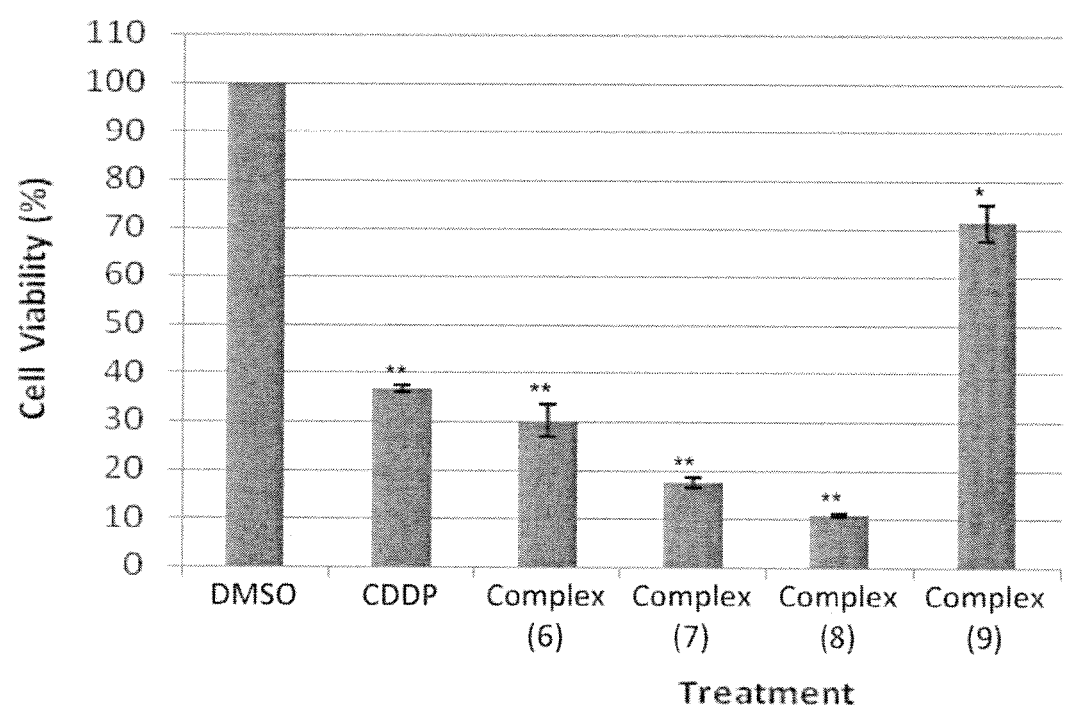
FIG. 12: Graph depicting the percentage viability of complexes (6)-(9) determined by the AlamarBlue® viability and proliferation assay. The SEM is indicated as error bars (n=9)

4. Cell Viability Determination and Morphological Studies
4.1 SNO-Oesophageal Cancer Cells Assays
The AlamarBlue® Viability and Proliferation Assay of SNO-Oesophageal Cancer Cells To determine whether complexes (6) to (9) exhibit toxic properties in SNO-oesophageal cancer cells, an AlamarBlue® fluorescent based assay was prepared (FIG. 12). A suspension (100 μl) of the differentially treated cells was added in triplicate to a microtiter plate. In the dark. AlamarBlue® dye (10 μl) was added to each well containing a sample, followed by a 2 hour incubation in a 5% $CO_2$ incubator at 37° C. The fluorescence was read on a Synergy HT Multi-Detection Microplate reader at a wavelength of 530 nm and (excitation) and 590 nm (emission). In terms of this study, the apoptotic control CDDP (100 μM) was included. Error bars represent the standard error of the mean (SEM) where n=9. The Student's T-test was used to determine the significant difference of the treatments with respect to DMSO (P*<0.05 and P**<0.001). The silver(I) nitrate phosphine complexes under evaluation decreased the cancer cell viability to a large extent compared to DMSO except complex (9).

Morphological Features of the SNO-Oesophageal Cancer Cells Following Differential Treatments as Evaluated by Inverse Light Microscopy An Axiovert 25 inverted microscope was used to examine if these complexes affect the morphological features of the malignant cells in any other way. This was done at a magnification of 100× with the use of Axio Version 3.1 software (Carl Zeiss, Gottingen, Germany).

Figure 13:
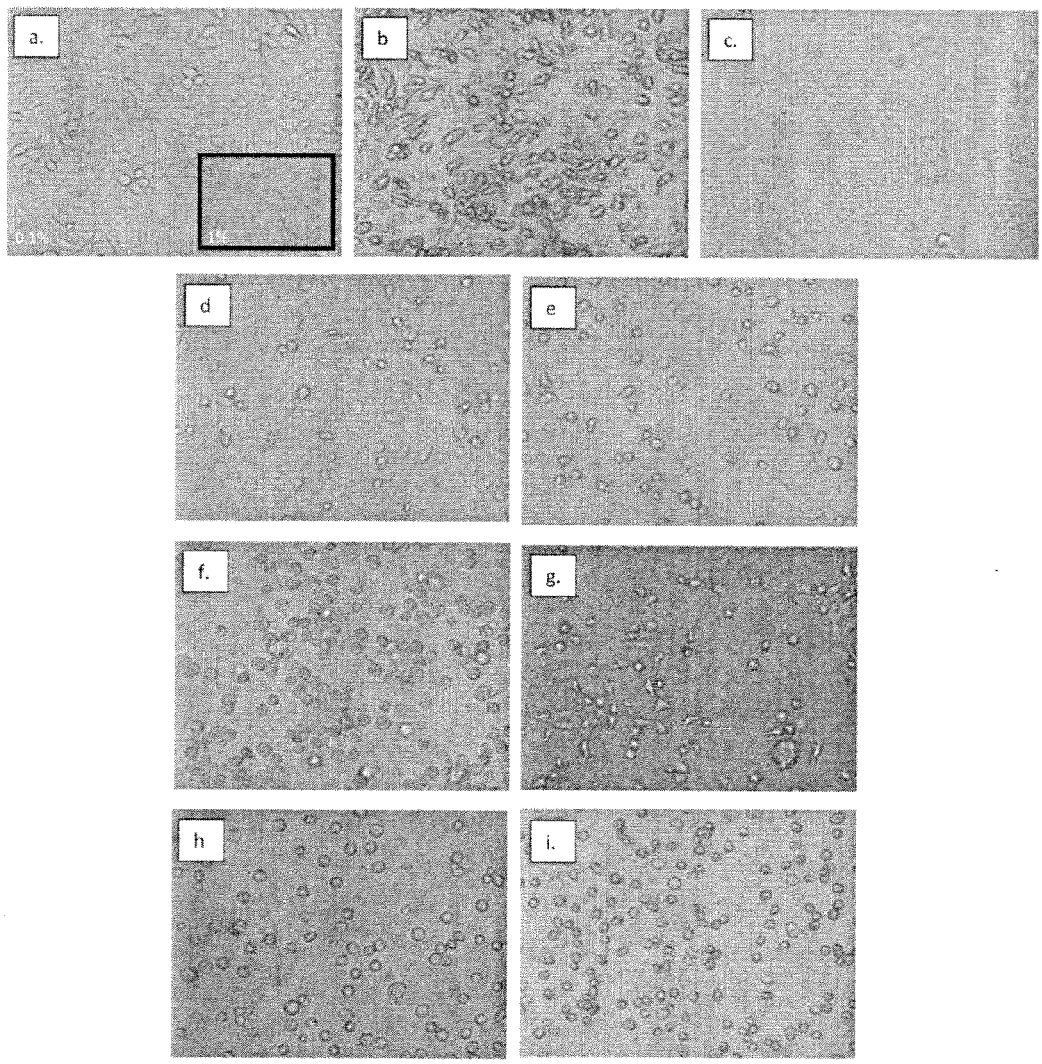
FIG. 13: Morphological analysis of SNO-oesophageal cancer cells following differential treatments as evaluated by inverse light microscopy.

FIG. 13 shows the morphological analysis done after 24 hours of treatment. FIG. 13(a) shows 0.1% DMSO treated cells including an image of 1% DMSO in bottom left corner, showing intact cells. FIG. 13 (b) shows SNO-oesophageal cancer cells treated with 100 μM COOP exhibiting the significant morphological features of apoptosis and FIG. 13(c) shows SNO-oesophageal cancer cells treated with 25% $H_2O_2$ exhibiting the significant morphological features of necrosis. FIG. 13(d-i) shows SNO-oesophageal cancer cells treated with 10 μM of complexes (6)-(9) respectively, whereby distinctive features of apoptosis can be observed.

Flow Cytometric Analysis of Apoptosis and/or Necrosis for SNO-Oesophageal Cancer Cells Approximately $3×10^5$ cells were washed with ice cold phosphate buffered saline solution (PBS). The cells were double labeled using an Annexin-V FITC assay kit adjusting the protocol. A 1× binding buffer (100 μl) was used to fix the cells, Annexin-V (2.5 μl) and Propidium Iodide (PI—5 μl) labels were added respectively followed by a 15 minute incubation, at room temperature, in the dark. After the incubation period, 400 μl of the 1× binding buffer was added, where counting of the cellular events was made using an FACSAria flow cytometer (BD Biosciences, San Jose, Calif.) with FACSDiva software (BD Biosciences, San Jose, Calif.). This technique in particular identifies whether predicted apoptotic cell death (or necrosis) was induced by these complexes.

Figure 14:
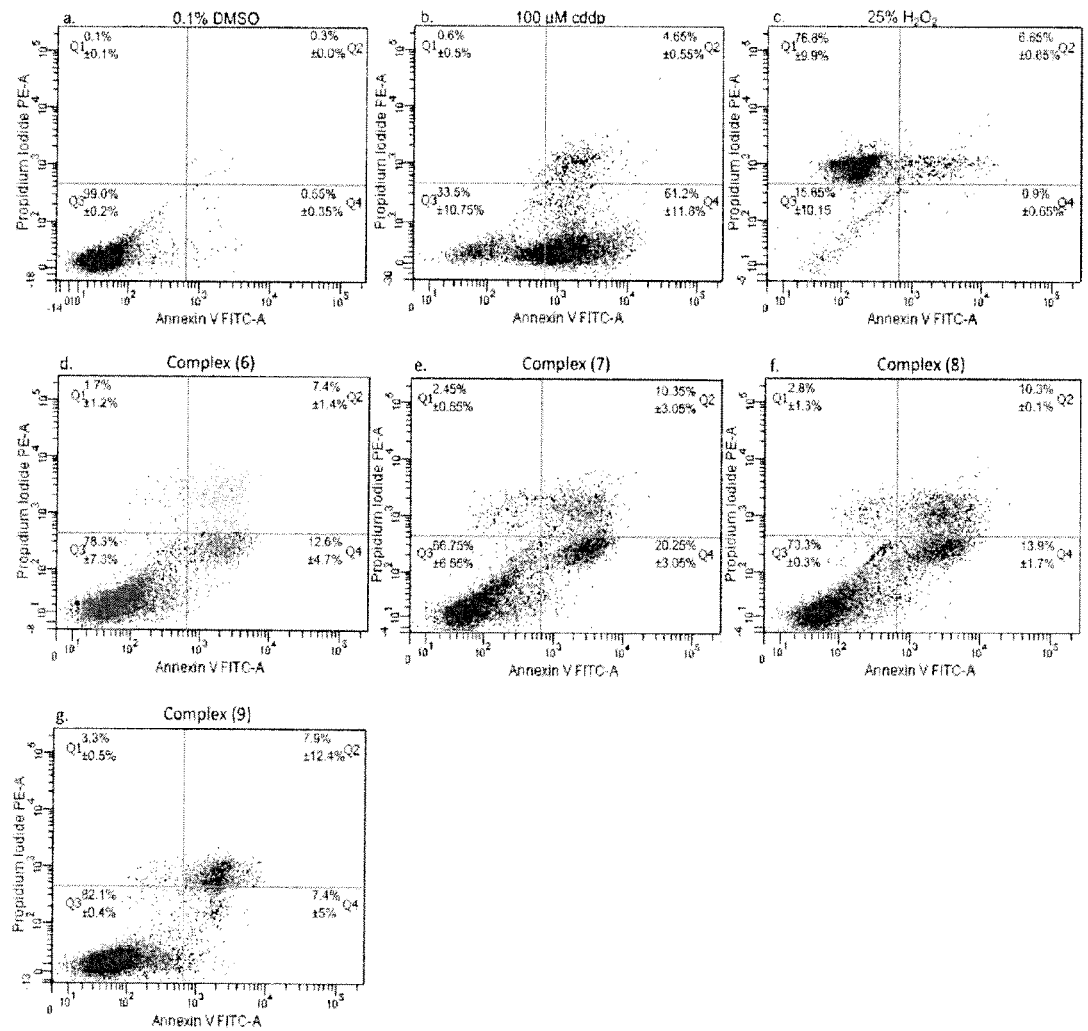
FIG. 14: Dot blots representing the mode of cellular death induced in SNO-oesophageal cancer cells following differential treatments.
Figure 15:
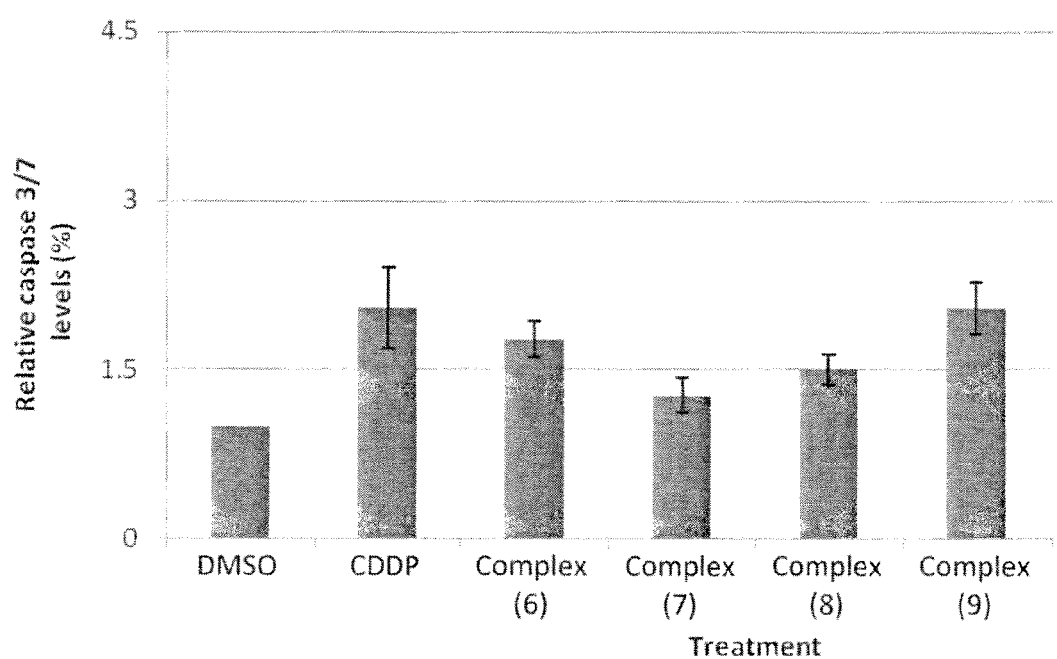
FIG. 15 Graph depicting Caspase-3/7 expression following differential treatments.
Figure 16:
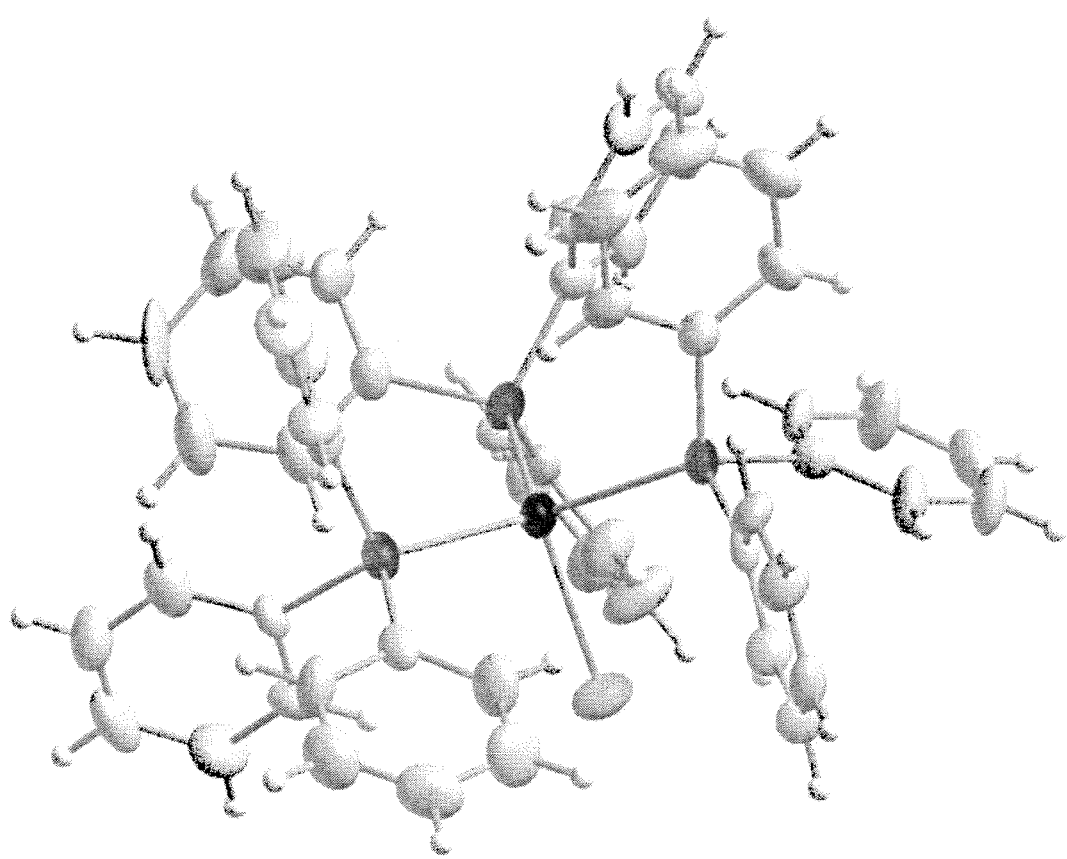
FIG. 16: Molecular diagram of complex (10)
Figure 17:
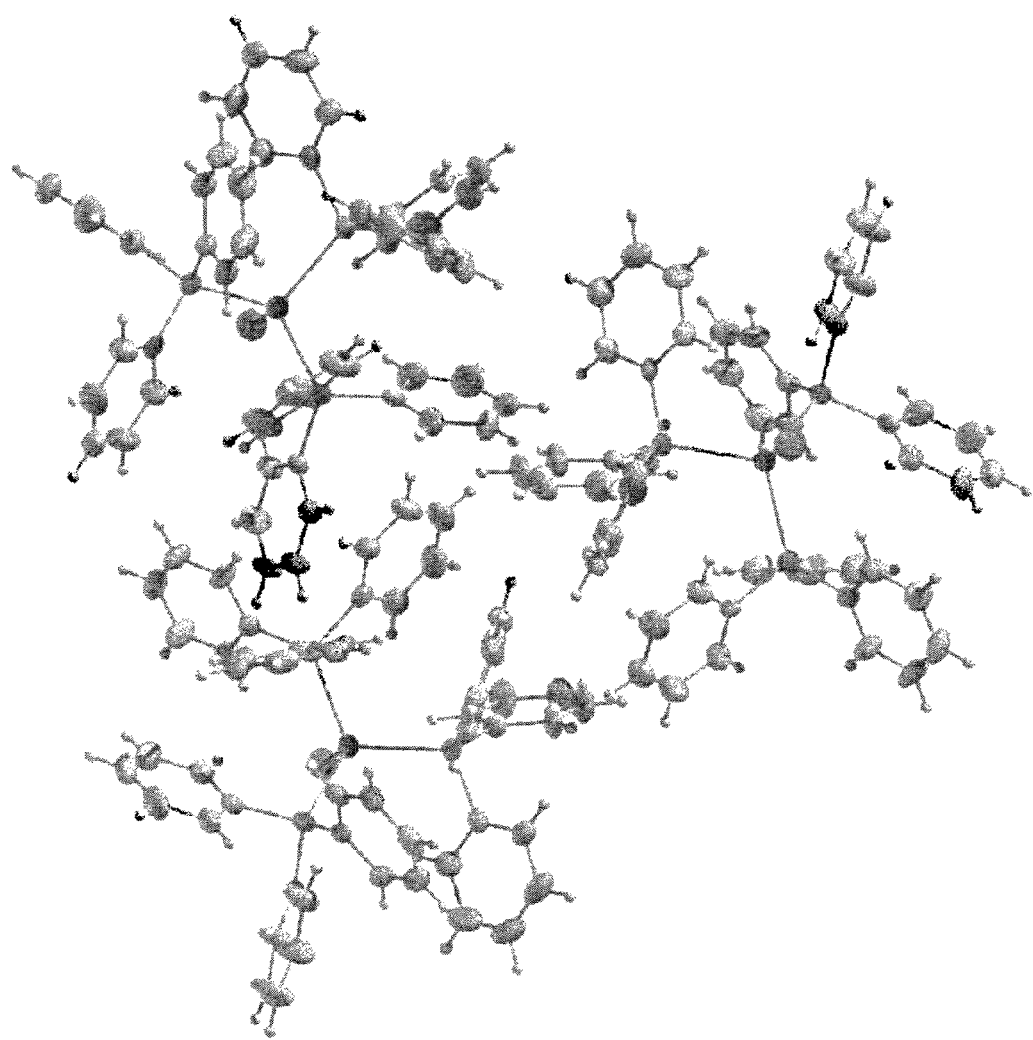
FIG. 17: Molecular diagram of complex (11)

As observed in FIG. 14, dot blots represent the mode of cellular death induced in the SNO-oesophageal cancer cells after 24 hours of treatment. FIG. 14(a): 0.1% DMSO, FIG. 14(b): 100 μM CDDP. FIG. 14(c): 25% $H_2O_2$, FIG. 14(d-i): complexes (6)-(9). An average percentage was calculated for all quadrants where the SEM is n=2 for all treatments. The four quadrants represent the following: Quadrant Q3 is negative for FITC and PI, Quadrant Q4 is positive for FITC but negative for PI, Quadrant Q1 is positive for PI but negative for FITC and Quadrant Q2 is positive for both FITC and PI. Cells undergoing early apoptosis are more likely to be found in Quadrant Q4 while those of late apoptosis and primary necrosis will be found in Quadrant Q2. Necrotic cell death is found in Quadrant Q1 while Quadrant Q3 indicates intact viable cells.

Apoptotic Pathway Investigation by Means of Caspase 3/7 Assay for SNO-Oesophageal Cancer Cells The Caspase-Glo®3/7 assay was used to confirm that the structural changes observed are due to apoptotic cell death. In this luminescent based assay, a 1:1 ratio of the Caspase-Glo® reagent was added to treated cells into a microtiter plate. The plate was gently agitated for 30 seconds and incubated for 30 minutes at room temperature. The whole luminescent intensity was measured using a Synergy HT Multi-Detection Microplate reader, where the intensity of the luminescence is proportional to the Caspase-3/7 concentration.

FIG. 7 shows Caspase-3/7 expression after 24 hours treatment with the relative complexes. The error bars where constructed based on the standard error of the mean (SEM) where n=6. The significant difference were calculated with respect to the vehicle control (P<0.001). A relative increase in expression was observed throughout.

Statistical Analysis

The data obtained was analyzed using Microsoft Excel, using the Student's T-test. All data is presented as the standard error of mean (±SEM), represented by the error bars and the p-value being significant at <0.05* and <0.01**, where n represents the number of biological repeats.

Chemical Analysis Discussion

The adducts of silver(I) nitrate and triphenylphosphine in a 1:1-1:4 ratio (complexes (6)-(9)) were prepared according to literature procedures. All complexes were spectroscopically characterized by IR, $^1H$, $^{13}C$ and $^{31}P$-NMR, and this data is in accordance with literature. In addition, microanalytical data provided proof of purity of the bulk sample. Since silver(I) nitrate phosphine complexes show a rich structural diversity, the identity of the prepared complexes was established by determining the unit cell for all complexes and comparing these with the literature values. All samples appeared to be identical to those reported previously.

Figure 11:
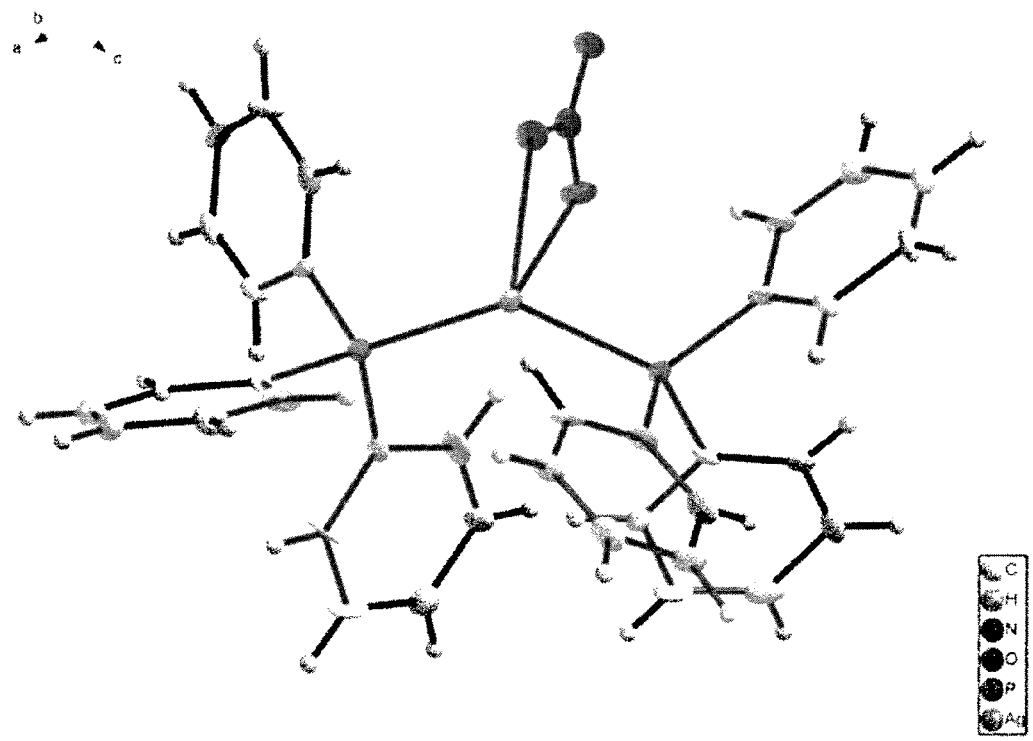
FIG. 11: Molecular diagram of complex (7)

Complex (6) is reported to be a polymeric compound, and complex (7) and (8) are coordinated complexes where the nitrate is found within the coordination sphere of the silver atom. Despite this solid-state behaviour, it was assumed that all complexes form separate cation-anion pairs in solution. A low-temperature re-determination of complex (7) confirms the nature of this complex as well as its coordination mode. The molecular diagram is presented in FIG. 11.

Biological Studies Discussion

Toxicity Profiles of Compounds

The silver(I) nitrate phosphine complexes (6)-(9) appeared to be highly toxic when compared to the vehicle control. The viability decreased especially when the cells were exposed to complexes (6)-(8), representing a ligand ratio of 1:1, 1:2 and 1:3 respectively. The degree of toxicity seems to increase as the ligand to metal ratio increases, but complex (9) on the other hand, with a ligand ratio of 1:4 only induced ±31.25% cancer cell death. There is currently no supporting literature and data on these observations based on the ratio, but does however confirm structure-activity relations in coordinated chemistry and toxicology (Reedijk, 2003).

Morphological Analysis

The morphological analysis by light microscopy gives insight to the structural changes including indication of the targeted cell death pathways like apoptosis or necrosis. As discussed herein before, apoptosis occurs when cellular damage has exceeded the capacity of repair (McCabe and Dlamini, 2005) leading to rapid condensation and budding of cells also known as apoptotic bodies. Necrosis results in cellular swelling, organelle dysfunction, mitochondrial collapse and disintegration (Kerr et al., 1994). Both an apoptotic (100 μM CDDP) and a necrotic (25% $H_2O_2$) control were included with complexes (6)-(9) (FIG. 13).

From FIG. 13a, the cells treated with both concentrations of DMSO were viable and intact. The cells exposed to 10 μM of complexes (6)-(9) (FIGS. 13d-13i) showed significant morphological changes after 24 hours treatment. All these complexes' morphology resembles that of apoptosis which is similar to Cisplatin, although a majority of cells are still viable in FIGS. 13d and 13g. Necrosis was absent in all treatments. To the Applicant's knowledge, this data is the first to show that these complexes target the apoptotic pathway in malignant cells specifically in SNO-oesophageal cancer cells.

Determination of the Mode of Cell Death

In apoptotic cells, the phospholipid phosphatidylserene (PS) is translocated from the inner to the outer layers of the plasma membrane exposing PS to the external environment (Elmore, 2007). Annexin-V is a calcium dependent phospholipid-binding protein, having a high affinity for PS and can be conjugated with FITC fluorochromes. It interacts with the PS of both apoptotic and necrotic cells making them undistinguishable. Propidium Iodide (PI) is an alternative fluorochrome which only binds to the PS of necrotic cells and acts as the discriminating label. In this case, an Annexin-V/PI assay was done to confirm the observations in FIG. 13. Dot blots where constructed and are represented in FIG. 14.

Flow cytometry showed that complexes (6)-(8) induced 20%, 30.6% and 24% apoptotic cell death respectively. These cellular events were observed in the early (Q4) and late Quadrants (Q2) with minimal or no necrotic cell death in (Q1). A large majority of the cancer cells where still viable and intact. Complex (9) had minimal cell death although 15.3% of the cells underwent apoptosis. The 1% DMSO (dot blot not included) had no affect on the cancer cells and 97.95% were still viable which was located in (Q3).

Confirmation of Apoptotic Cell Death by Monitoring Caspase-3 Cleavage

CaspaseGlo® 3/7 is an apoptotic assay and was utilized based on the principle that activated Caspases in apoptotic cells cleave the synthetic substances to release free chromophores measured spectrophotometrically. Other metals in cancer research, such as Iron and Copper have also been shown to activate Caspase-3, -6, and -7 as initiator Caspases (Jimenez and Velez-Pardo, 2004). Caspase-3/7 assay was utilised as confirmation of apoptosis.

Caspase induction was observed for the positive apoptotic control Cisplatin (2 fold increase), which has been shown to induce Caspase-3, -8 and -9 dependant apoptosis (Sadler and Guo, 1998). The levels of Caspase-3/7 increased with most treatments. Complex (9) had a low cytotoxicity (FIG. 12) and minimal PS externalisation (FIG. 14g) but showed a distinctive increase in Caspase-3/7 expression of 2.74%. This is higher than the (6)-(8) treatments even though they showed significant cytotoxicities (FIG. 12).

Complex (9) in particular could target other factors in the malignant cells which results in Caspase cleavage via an alternative mechanism. This therefore shows that apoptosis is induced and is Caspase dependent, however further studies are to be made in differentiating between the extrinsic and intrinsic pathways of apoptosis. Silver nanoparticles induce apoptosis via a mitochondria- and Caspase-dependent pathway. They decrease Bcl-2 expression and increase Bax expression in a time dependent manner. The change in the Bax/Bcl-2 ratio leads to the release cytochrome C from the mitochondria into the cytosol. These nanoparticles activate Caspase-9 and -3 in a time-dependent manner from 6 hours to 48 hours respectively (Piao et al., 2011). Silver induced mitochondrial membrane damage has shown to result in the induction of programmed cell death, resulting in decreased ATP production (Teodoro et al., 2011). It has also been shown that silver compounds enter fibroblasts and hepatocytes and cause DNA damage leading to the induction of apoptosis (Piao et al., 2010).

5. Conclusion

A number of silver(I) nitrate triphenylphosphine complexes were synthesised and their in vitro cytotoxicity has been assessed against SNO-oesophageal cancer cells. It was found that these complexes induce apoptosis as the mode of cell death based on microscopy as well as dye exclusion experiments. The cytotoxicity profile of the silver(I) complexes were found to be superior as compared to Cisplatin. The degree of apoptotic cell death has been observed to be dependent on the ratio of ligands bound to the metal. Flow cytometry experiments and Caspase analysis confirmed that the mode of cell death was apoptosis. A major barrier to the continued development of these compounds as anti-cancer agents is the lack of a defined mechanism.

C: Toxicity Evaluation of Silver(I) Chloride, Bromide and Cyanide Triphenylphosphine Complexes of the Invention and the Toxicity Evaluation Thereof on SNO-Oesophageal Cancer Cells 1. General Silver chloride, silver bromide and silver cyanide, triphenylphosphine, acetonitrile and ethanol were obtained from Sigma-Aldrich. Infrared spectra were recorded on a Bruker Tensor 27 FT-IR spectrophotometer, using an ATR accessory with a ZnSe crystal. $^1$H NMR (400 MHz) and $^{13}$C NMR (75 MHz) spectra were recorded on a Bruker Avance III 400 MHz spectrometer, using tetramethylsilane as an internal standard. Melting points were recorded on a Stuart Scientific Melting Point apparatus SMP10, and are uncorrected. Gentomycin. Hanks balanced salt solution and trypsin were obtained from Highveld Biological, Kelvin, RSA. AlamarBlue and Annexin-V FITC assay kits were obtained from Serotec, Oxford, UK. All reagents were used as supplied.

All compounds were prepared according to literature procedures. Microanalysis was performed by Dr Edith Antunes in the Department of Chemistry, Rhodes University, RSA on a Thermo Flash 2000 series CHNS/O, Organic Elemental Analyser.

2. Synthesis of Complexes

Preparation of Silver(I) Chloride, Bromide and Cyanide Triphenylphosphine Complexes of the Invention Example 1

AgCl(PPh$_3$)$_3$ Complex (10)

AgCl (0.50 g, 3.5 mmol) was added to a solution of PPh$_3$ (2.76 g, 10.5 mmol) in acetonitrile (50 ml). The mixture was refluxed until all the reagents dissolved. The solution was filtered while hot, and the solvent was concentrated to 20 ml. The solution was allowed to cool to room temperature, after which colourless crystals suitable for XRD were obtained. Yield: 65%, mp 190° C.; IR: $v_{max}$/cm$^-$: 3054 (w), 2117 (w), 2081 (w), 1978 (w), 1881 (w), 1831 (w), 1773 (w), 1664 (w), 1570 (w), 1478 (s), 1433 (s), 1326 (m), 1306 (m), 1281 (w), 1184 (w), 1156 (w), 1091 (s), 1069 (m), 1026 (w), 996 (w), 913 (w), 854 (w), 741 (s), 691 (s). $^1$H NMR: (400 MHz, CDCl$_3$): δ (ppm) 7.40 (t, J=7.2 Hz), 7.31 (t, J=7.2 Hz), 7.23 (t, J=8.2 Hz). $^{13}$C{$^1$H} NMR: (100 MHz, CDCl$_3$): δ (ppm) 133.3 (d, J(C—P)=13.5 Hz), 131.51, 129.47, 128.7 (d, J=3.0 Hz). $^{31}$P{$^1$H} NMR: (161 MHz, CDCl$_3$): δ (ppm) 25.62. Elemental Analysis: (Anal. Calcd. For C$_{54}$H$_{45}$AgClP$_3$: C, 69.73; H, 4.88; N, 0. Found: C, 69.74; H, 4.91; N, 0).

Example 2

AgBr(PPh$_3$)$_3$ Complex (11)

AgBr (0.30 g, 1.6 mmol) was added to a solution of PPh$_3$ (1.26 g, 4.8 mmol) in acetonitrile (50 ml). The mixture was refluxed until all the reagents dissolved. The solution was filtered while hot, and the solvent was concentrated to 20 ml. The solution was allowed to cool to room temperature, after which colourless needles suitable for XRD were obtained. Yield: 60%; mp 192° C.; IR: $v_{max}$/cm$^{-1}$: 3047 (w), 2113 (w), 1981 (w), 1955 (w), 1885 (w), 1805 (w), 1670 (w), 1584 (w), 1570 (w), 1477 (s), 1432 (s), 1382 (s), 1307 (s), 1181 (w), 1156 (w), 1095 (s), 1069 (m), 1024 (m), 996 (m), 920 (w), 841 (w), 739 (s), 689 (s). $^1$H NMR: (400 MHz, CDCl$_3$): δ (ppm) 7.59 (t, J=6.0 Hz), 7.65 (d, J=2.8 Hz), 7.35 (t, J=5.0

Hz). $^{13}C\{H\}$ NMR: (100 MHz, CDCl$_3$): δ (ppm) 134.0 (d, J(C—P)=12.4 Hz), 133.0 (d, J(C—P)=16.2 Hz), 130.72, 129.3 (d, J=6.8 Hz). $^{31}P\{H\}$ NMR: (161 MHz, CDCl$_3$): δ (ppm) 25.48. Elemental Analysis: (Anal. Calcd. For C$_{54}$H$_{45}$AgBrP$_3$: C, 66.55; H, 4.65; N, 0. Found: C, 65.20; H, 4.58; N, 0)

Example 3

AgCN(PPh$_3$)$_3$ Complex (12)

AgCN (0.15 g, 1.12 mmol) was added to a solution of PPh$_3$ (0.6 g, 2.24 mmol) in acetonitrile (50 cm$^3$). The mixture was heated under reflux for 48 hours. The solution was filtered while hot, and the solvent was reduced to 20 cm$^3$. The solution was allowed to cool to room temperature, after which colorless colorless needles suitable for XRD were obtained. Yield: 75%; mp 193° C.; IR: $v_{max}$/cm$^{-1}$: 3056 (w), 2323 (w), 2119 (m), 1891 (w), 1823 (w), 1670 (w), 1585 (w), 1478 (s), 1433 (s), 1309 (m), 1182 (w), 1182 (w), 1156 (w), 1092 (s), 1069 (m), 1026 (w), 997 (w), 917 (m), 849 (w), 740 (s), 691 (s). $^1$H NMR: (400 MHz, CDCl$_3$): δ (ppm) 719 (t, J=7.0 Hz), 7.18 (m, J=7.0 Hz), 3.33. $^{13}C\{H\}$ NMR: (100 MHz, CDCl$_3$): δ (ppm) 133.8 (d, J(C—P)=12.5 Hz), 133.4 (d, J=12.0 Hz), 130.58, 129.3 (d, J=14.9 Hz). $^{31}$P(1-1 NMR: (161 MHz, CDCl$_3$): δ (ppm) 25.53. Elemental Analysis: (Anal. Calcd. For C$_{37}$H$_{30}$AgNP$_2$: C, 67.49; H, 4.59; N, 2.13. Found: C, 67.07; H, 4.99; N, 2.11).

For ease of reference, the chemical structures of complexes (10)-(12) are provided herein below:

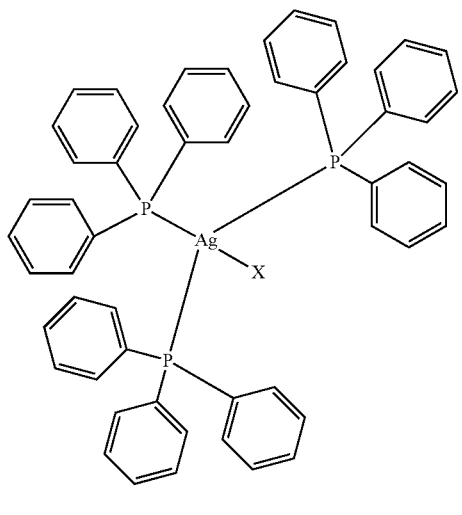

X = Cl$^-$ (10), Br$^-$ (11), CN$^-$ (12)

3. Cell Culturing and Treatment

SNO-oesophageal cancer cells were a gift from the University of Pretoria, RSA. They were cultured in Dulbecco's modified Eagles medium (DMEM) containing 10% Foetal bovine serum (FBS), 1.8% Penicillin/Streptomycin/Fungizone and 0.4% Gentamicin sulphate. The SNO-oesophageal cancer cells were subcultured every 48 hours and incubated at 37° C. under a 5% CO$_2$ humidified atmosphere. After 48 hours the cells were trypsinized and plated (6×10$^5$ cells) in 3.5 cm culture dishes and left to cultivate for 24 hours.

SNO-oesophageal cancer cells were treated with 14 μM silver(I) complexes (10)-(12) for 24 hours. The treatments were prepared in Dimethyl sulfoxide (DMSO) and didn't exceed 1%. For comparative purposes, 100 μM Cisplatin (CDDP) and 25% H$_2$O$_2$ was included which respectively serves as the apoptotic and necrotic controls. Cisplatin was prepared in 0.9% NaCl, whereas H$_2$O$_2$ was prepared in the supplemented DMEM media right before treatment. An untreated negative control (UC) was exposed to similar conditions as the treated cells and monitored during the experimental study.

Several assays were used to evaluate the effect of complexes (10)-(12) on cell death with respect to the SNO-oesophageal cancer cells. These included cell viability assays such as the AlamarBlue® viability and proliferation assay, microscopy to evaluate cell morphology and flow cytometric analysis of apoptosis and/or necrosis.

4. Cell Viability and Morphological Studies 4.1 SNO-Oesophageal Cancer Cells Assays The AlamarBlue® Viability and Proliferation Assay of SNO-Oesophageal Cancer Cells An AlamarBlue® (Serotec, UK) assay was done to investigate the proliferation capabilities of the differentially treated cells. AlamarBlue® dye (10%) was incubated with trypsinized cells over a 2-hour period before the fluorescence was measured with a Synergy HT Multi-Detection Microplate reader (BioTek, Winooski, Vt.) at wavelengths of 530 nm and (excitation) and 590 nm (emission). This assay, in particular involves the metabolic oxidation-reduction reaction of resazurin to a reduced resorufin product that is directly proportional to the amount of viable cells.

Figure 18:
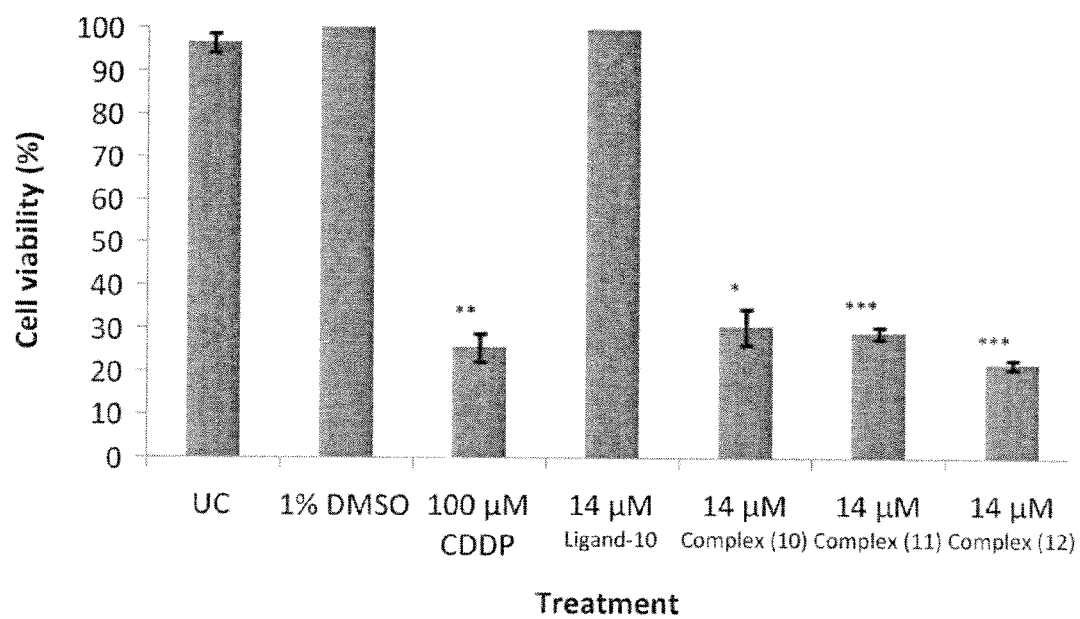
FIG. 18: Graph depicting the percentage viability of complexes (10)-(12) determined by the AlamarBlue® viability and proliferation assay. The SEM is indicated as error bars (n 3)

FIG. 18 shows the cellular viability of the SNO-oesophageal cancer cells after 24 hour treatment, determined by means of an AlamarBlue® assay. Cells were treated with 14 μM (10), (11) and (12) including Ligand-10. An untreated control (UC), 1% DMSO vehicle control and 100 μM Cisplatin (CDDP) serving as the positive control was included. The percentage viabilities were calculated with respect to 1% DMSO. Error bars were constructed based on the Standard Error of the Mean (SEM) where n=9 repeats (3 biological and 3 technical). The P-values (*P<0.05, P<0.001 and *P<0.00001) were calculated h the Student's T-test to evaluate the significant difference.

Figure 19:
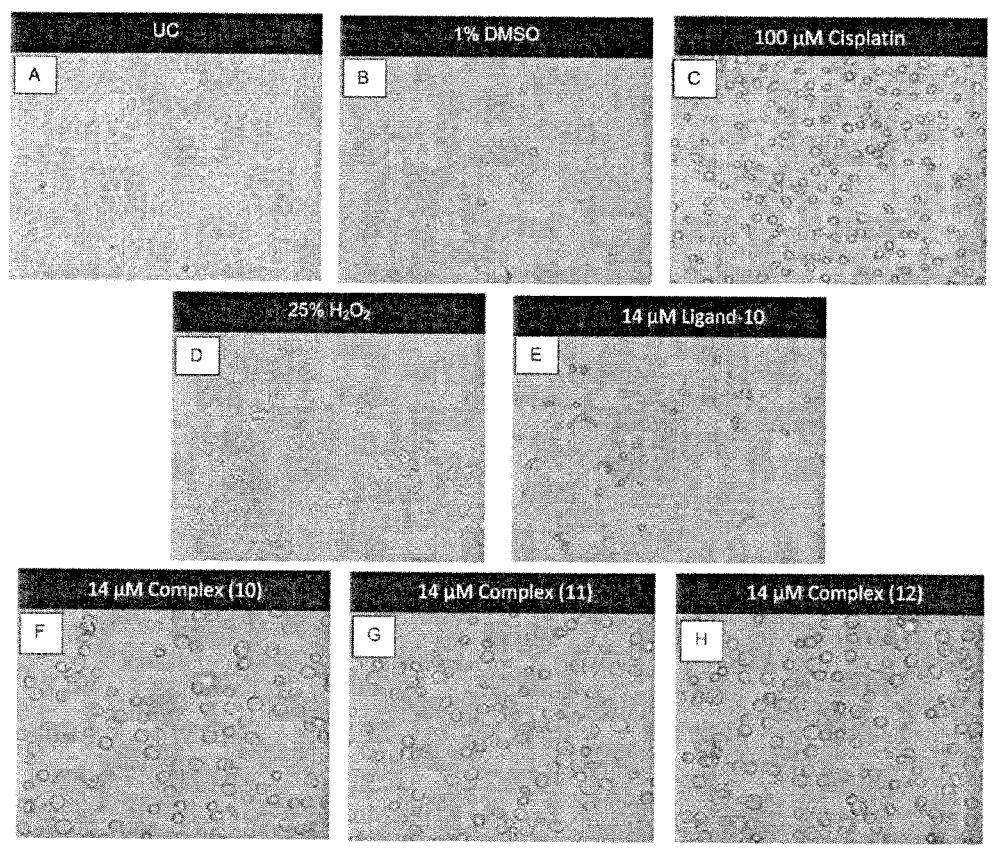
FIG. 19: Morphological analysis of SNO-oesophageal cancer cells following differential treatments of complexes (10)-(12) and Ligand-10 as evaluated by inverse light microscopy.

Morphological Features of the SNO-Oesophageal Cancer Cells Following Differential Treatment as Evaluated by Inverse Light Microscopy Morphological studies where done after 24 hours of treatment to determine how these compounds influence/change specific features of the malignant SNO-oesophageal cancer cells, compared to the untreated (UC) and 1% DMSO vehicle control. The treated cancer cells including their controls were examined under an Axiovert 25 inverted light microscope (Carl Zeiss, Göttingen, Germany) with Axio Vision 3.1 software (Carl Zeiss, Göttingen, Germany) using a 100× magnification. In FIG. 19, the morphology of the different controls including Ligand-10 and complexes (10)-(12) are represented. To predict the targeting mechanisms of these compounds, the treated cells were compared to 100 μM Cisplatin (apoptotic control) and 25% H$_2$O$_2$ (necrotic control). Thus, as shown in FIG. 19, cells were either untreated (A), treated with vehicle control (B), apoptotic control (C), necrotic control (D), Ligand-10 (E) or complexes (10)-(12) (F-H).

Flow Cytometric Analysis of Apoptosis and/or Necrosis for SNO-Oesophageal Cancer Cell Assays To determine if either apoptosis or necrosis occurred, the cells were double labelled with Annexin-V FITC and Propidium Iodide (PI) by means of an Annexin-V FITC assay kit (Serotec, UK). This was done according to manufactures instructions with a few adjustments. As mentioned herein above, Annexin-V FITC binds to the inner leaflet of PS when apoptosis and necrosis takes place, making the cellular deaths undistinguishable. This is overcome by using PI as an alternative label that interacts with exposed DNA of necrotic cells only, leading to the flow cytometric detection of both these labels.

The cells ($\pm 3 \times 10^5$ cells/ml) were washed twice with cold phosphate buffered saline (PBS), followed by the addition of 100 μl 1× binding buffer. Two and a half microliters of Annexin-V along with 5 μl PI were added in the dark and was incubated for 15 minutes at room temperature. After incubation, 400 μl 1× binding buffer was added and cells were analysed using the FACSAria flow cytometer (BD Biosciences, San Jose, Calif.) with FACSDiva software (BD Biosciences, San Jose, Calif.) 492 nm (excitation) and 520 nm for Annexin and 488 nm and 575 nm (emission) for Propidium Iodide.

Figure 20:
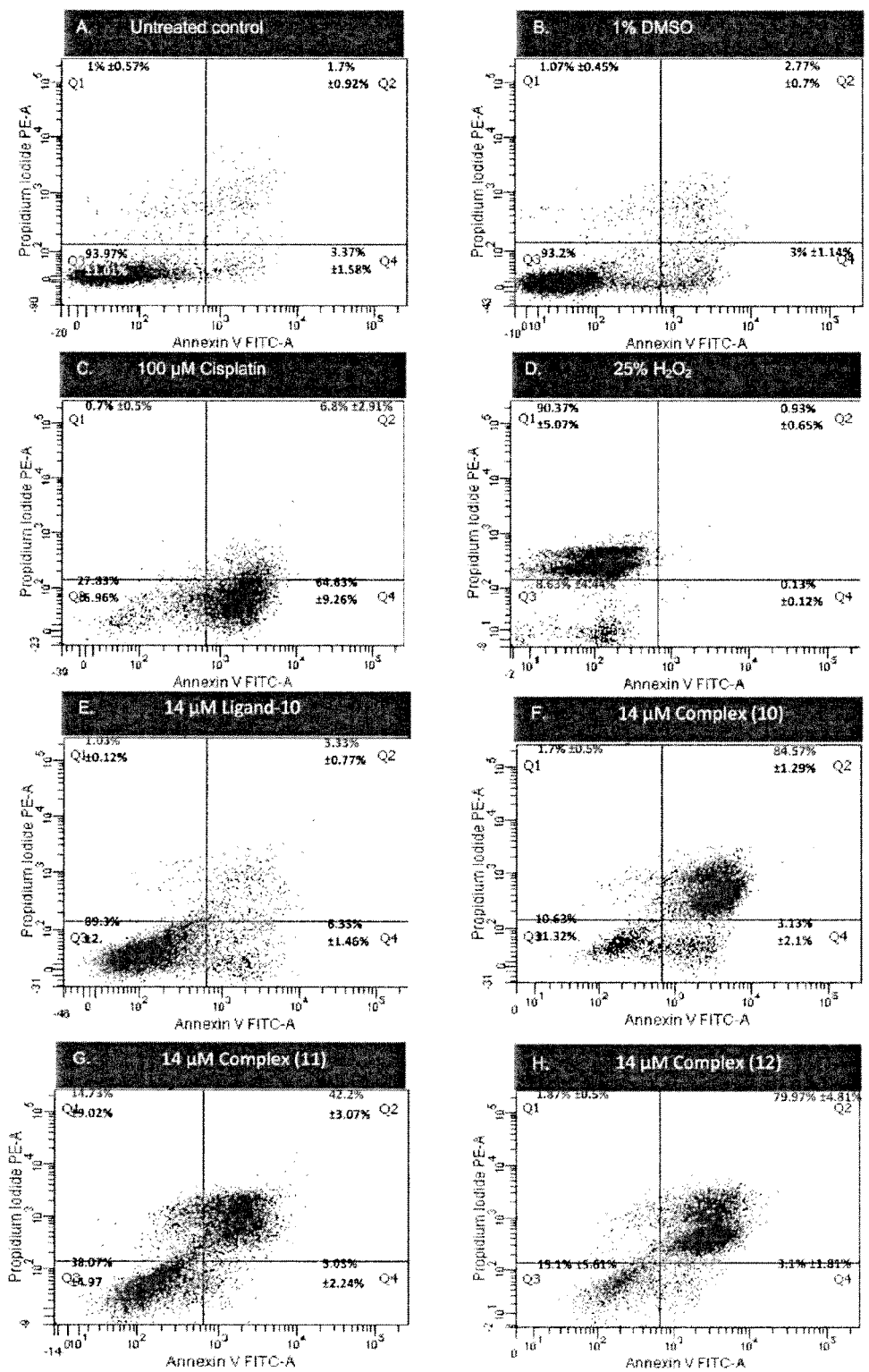
FIG. 20: Dot blots representing the mode of cellular death induced in SNO-oesophageal cancer cells following differential treatments of complexes (10)-(12) and Ligand-10.

SNO-oesophageal cancer cells were treated with complexes (10)-(12) including controls for 24 hours. Dot blots in FIG. 20 represent the mode of cellular death. As shown in FIG. 20, an untreated control (A), DMSO vehicle control (B), apoptotic (C) and necrotic control (D) was included. Cells were treated with Ligand-10 (E) including complexes (10), (11) and (12) (F—H). The average percentage was calculated for all quadrants (n=3) followed by the ±standard deviation. The four quadrants represent: Quadrant Q3 is negative for FITC and PI, Quadrant Q4 is positive for FITC but negative for PI, Quadrant Q1 is positive for PI but negative for FITC and Quadrant Q2 is positive for both FITC and PI. As discussed herein before, cells undergoing early apoptosis are more likely to be found in Quadrant Q4 while those of late apoptosis and primary necrosis will be found in Quadrant Q2. Necrotic cell death is found in Quadrant Q1 while Quadrant Q3 indicates intact viable cells.

The untreated control had minimal cell death consisting of an average viability of 93.97%. This was similar to the 1% DMSO vehicle control. Cellular death was minimal in the controls, but on the contrary apoptosis and necrosis was induced in the malignant cells treated with the different silver(I) complexes (10), (11) and (12). Late apoptotic cell death was more apparent. Complex (10) and (12) had the highest apoptotic SNO-oesophageal cancer cells with a total of over 80% (early and late stages). Complex (11) on the other hand induced apoptotic death in 47.23% (early and late stages) of the malignant cells while 38.07% of the cells seemed viable and intact. Necrotic cell death was minimal in these silver(I) treatments although complex (11) showed to have 14.73% necrotic cells positive for PI. Ligand-10 once again did not influence the cellular viability and PS externalisation like the respective treatments.

Statistical Analysis

Data represented were expressed as the Standard Error of Mean (SEM) where at least 3 biological and 3 technical repeats (except for the dot blots) were used. The Student's T-test was used to calculate the significant difference (*P<0.05, P<0.001 and *P<0.00001) of the treatments with respect to the untreated control except in the flow cytometric data where the standard deviation was calculated.

Biological Studies Discussion

Toxicity Profiles of Compounds

When compared to the vehicle control, all treatments with silver(I) complexes (10), (11) and (12) significantly induced cancer cell death, especially complex (11) and complex (12) (P<0.00001). These complexes were even more toxic than the platinum based compound. Cisplatin which killed ±74% cells at a high concentration of 100 μM. The Ligand-10 treatment on the other hand was less toxic with a viability of 99.03%. This signifies their minimal influence in cancer cell targeting on their own.

Morphological Analysis

The untreated control and 1% DMSO treatments (A and B) represent no signs of cellular death. When compared to complexes (10), (11) and (12) (F-H) multiple signs of apoptosis that involve blebbing and apoptotic body formation (Kerr et al., 1972) can be seen. As seen from the 25% $H_2O_2$ treatment (D), necrotic cancer cells can be characterized by extensive cell swelling and bursting, which results in the release of cellular content (Kroemer et al., 2009). Minimal necrotic cell death was observed in the cancer cells treated with complexes (10), (11) and (12). Ligand-10 (E) on the other hand showed minimal cell death similar to apoptosis although the majority seems viable.

5. Conclusion

Theses silver(I) phosphine compounds, $Ag(PPh_3)_3Cl$ (10), $Ag(PPh_3)_3Br$ (11) and $Ag(PPh_3)_3CN$ (12) were used to treat SNO-oesophageal cancer cells. All complexes were found to be highly toxic to the cancer cells. AlamarBlue® fluorescence assays combined with morphological studies confirmed that the silver(I) complexes (10), (11) and (12) resulted in apoptosis of the SNO-oesophageal cancer cells. These results were confirmed by flow cytometric analysis.

Example D

Silver(I) Bromide Triphenylphosphine and Silver(I) Nitrate Triphenylphosphine Complexes of the Invention and the Toxicity Evaluation Thereof on A375 Malignant Melanoma Cancer Cells 1. General Silver bromide, silver nitrate, triphenylphosphine, acetonitrile and ethanol were obtained from Sigma-Aldrich. Infrared spectra were recorded on a Bruker Tensor 27 FT-IR spectrophotometer, using an ATR accessory with a ZnSe crystal. $^1H$ NMR (400 MHz) and $^{13}C$ NMR (75 MHz) spectra were recorded on a Bruker Avance III 400 MHz spectrometer, using tetramethylsilane as an internal standard. Melting points were recorded on a Stuart Scientific Melting Point apparatus SMP10, and are uncorrected. Gentomycin. Hanks balanced salt solution and trypsin were obtained from Highveld Biological, Kelvin, RSA. AlamarBlue and Annexin-V FITC assay kits were obtained from Serotec, Oxford, UK. All reagents were used as supplied.

All compounds were prepared according to literature procedures. Microanalysis was performed by Dr Edith Antunes in the Department of Chemistry, Rhodes University, RSA on a Thermo Flash 2000 series CHNS/O, Organic Elemental Analyser.

2. Synthesis of Complexes

Example 1

$AgBr(PPh_3)_3$ Complex (13)

AgBr (0.30 g, 1.6 mmol) was added to a solution of $PPh_3$ (1.26 g, 4.8 mmol) in acetonitrile (50 ml). The mixture was refluxed until all the reagents dissolved. The solution was filtered while hot, and the solvent was concentrated to 20 ml. The solution was allowed to cool to room temperature, after which colourless needles suitable for XRD were obtained. Yield: 60%; mp 192° C.; IR: $v_{max}/cm^{-1}$: 3047 (w), 2113 (w), 1981 (w), 1955 (w), 1885 (w), 1805 (w), 1670 (w), 1584 (w), 1570 (w), 1477 (s), 1432 (s), 1382 (s), 1307 (s), 1181

(w), 1156 (w), 1095 (s), 1069 (m), 1024 (m), 996 (m), 920 (w), 841 (w), 739 (s), 689 (s). $^1$H NMR: (400 MHz, CDCl$_3$): δ (ppm) 7.59 (t, J=0.0 Hz), 7.65 (d, J=2.8 Hz), 7.35 (t, J=5.0 Hz). $^{13}$C{H} NMR: (100 MHz, CDCl$_3$): δ (ppm) 134.0 (d, J(C—P)=12.4 Hz), 133.0 (d, J(C—P)=16.2 Hz), 130.72, 129.3 (d, J=6.8 Hz). $^{31}$P{H} NMR: (161 MHz, CDCl$_3$): δ (ppm) 25.48. Elemental Analysis: (Anal. Calcd. For C$_{54}$H$_{45}$AgBrP$_3$: C, 66.55; H, 4.65; N, 0. Found: C, 65.20; H, 4.58; N, 0).

Example 2

AgNO$_3$(PPh$_3$)$_3$ Complex (14)

AgNO$_3$ (0.20 g, 1.17 mmol) was added to a solution of PPh$_3$ (0.93 g, 3.5 mmol) in acetonitrile (50 cm$^3$). The mixture was heated under reflux until all the reagents dissolved. The solution was filtered while hot, and the solvent was concentrated to 20 cm$^3$. The solution was allowed to cool to room temperature, after which colourless crystals were obtained. Yield: 72%; mp 233° C.; IR: $v_{max}$/cm$^{-1}$: 1382, 1308, 1027, 824. $^1$H NMR: (400 MHz, CDCl$_3$): δ (ppm) 7.45 (t, δ$_1$=7.472, δ$_2$=7.454, δ$_3$=7.436 $^1$J=7.2 Hz), 7.30 (t, δ$_1$=7.318, δ$_3$=7.300, δ$_3$=7.281 $^1$J=7.4 Hz), 7.17 (t, δ$_1$=7.192, δ$_2$=7.168, δ$_3$=7.147 $^1$J=9 Hz. $^{13}$C{H} NMR: (100 MHz, CDCl$_3$): δ (ppm) 133.3 (d, δ$_1$=133.36, δ$_2$=133.20, $^1$J(C—P)=12.0 Hz), 132.18, 131.98, 130.47, 129.0 (d, δ$_1$=129.07, δ$_2$=128.98, $^1$J=6.8 Hz). $^{31}$P{H} NMR: (161 MHz, CDCl$_3$): δ (ppm) 6.41. Elemental Analysis: (Anal. Calcd. For C$_{54}$H$_{45}$P$_3$AgNO$_3$: C, 67.79; H, 4.74; N, 1.46. Found: C, 67.83; H, 4.73; N, 0.68).

For ease of reference, the chemical structures of complexes (13) and (14) are provided herein below:

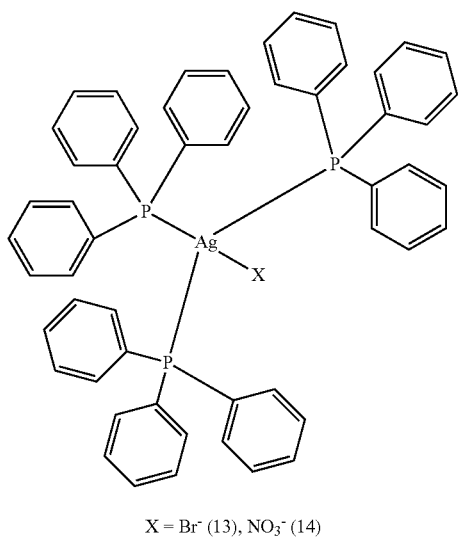

X = Br$^-$ (13), NO$_3^-$ (14)

3. Cell Culturing and Treatment

A375 melanoma cancer cells originate from an immortal cell line from human malignant melanoma from skin (ATCC no CRL-1619).

A375 malignant melanoma cancer cells were cultured in Dulbecco's Modified Eagle's Medium (DMEM), 13.53 g/L with sodium bicarbonate (NaHCO3), 3.7 g/L supplemented with 10% fetal bovine serum (FBS), and 1% Penicillin/Streptomycin/Fungizone in 75 cm$^3$ sterile culture flasks. Cells were incubated at 37° C. with 5% CO$_2$ in a humidified atmosphere and were subcultured twice a week. Cells were subcultured every 48 hours and used between Passages 3 and 7. For experiments, cells were trypsinized and plated at a concentration of 2×10$^5$ cells/mL using 3.0 mL supplemented DMEM in 3.5 cm$^3$ culture dishes and left to cultivate for 24 hours.

Complexes (13) and (14) under investigation were dissolved in 1.0% Dimethyl sulfoxide (DMSO). DMSO alone (vehicle control/VC) had minimal influence on cancer cell proliferation with a small decrease in the viability of approximately 6.0%. For comparative purposes, 100 μM Cisplatin (CDDP) and 25% H$_2$O$_2$ was included to serve as positive apoptotic and necrotic controls respectively. Cisplatin was prepared in 0.996 NaCl, whereas H$_2$O$_2$ was prepared in the supplemented DMEM media right before treatment. An untreated negative control (UT) was exposed to similar conditions as all treated cells were monitored throughout the experimental study. The silver(I) bromide triphenylphosphine complex (13) and silver(I) nitrate triphenylphosphine complex (14) were tested with concentration ranges from 0 μM (1.0° A DMSO Vehicle Control/VC) to 10 μM.

Several assays were used to evaluate the effect of complexes (13) and (14) on cell death with respect to the A375 malignant melanoma cancer cells. These included cell viability assays such as the AlamarBlue® viability and proliferation assay and the Trypan blue exclusion assay, microscopy to evaluate cell morphology and flow cytometric analysis of apoptosis and/or necrosis.

4. Cell Viability and Morphological Studies
4.1 A375 Malignant Melanoma Cancer Cells Assays
The AlamarBlue® Viability and Proliferation Assay of A375 Malignant Melanoma Cancer Cells An AlamarBlue® (Serotec, UK) assay was done to investigate the proliferation capabilities of the differentially treated cells. AlamarBlue® dye (10%) was incubated with trypsinized cells over a 2-hour period before the fluorescence was measured with a Synergy HT Multi-Detection Microplate reader (BioTek, Winooski, Vt.) at wavelengths of 530 nm and (excitation) and 590 nm (emission).

Biological repeats were then combined into 1 standard curve to determine IC50 value for the respective complex.

Figure 21:
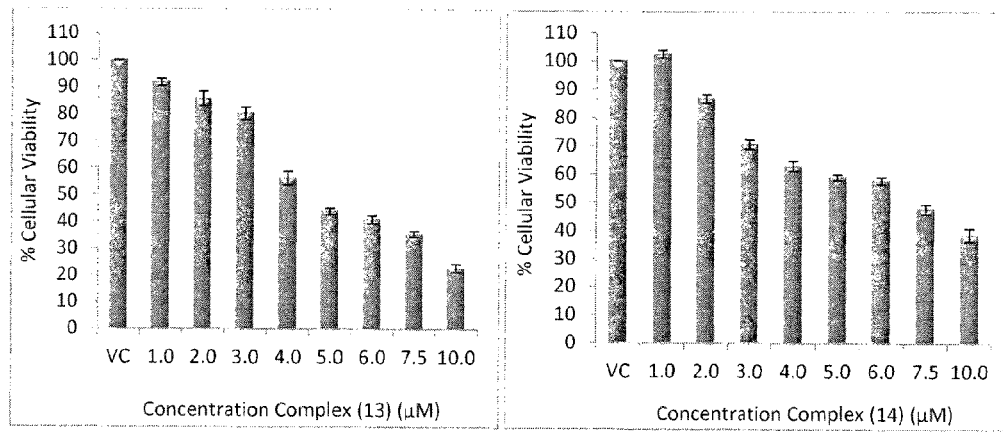
FIG. 21: Bar chart showing percentage cellular viability of A375 malignant melanoma cancer cells treated with a concentration range of complex (13) and complex (14)

FIG. 21 is a bar chart showing percentage cellular viability of 2×10$^5$ A375 malignant melanoma cancer cells/mL treated with a concentration range (1.0 μM-10.0 μM) of complex (13) (left) and complex (14) (right) using the AlamarBlue® cell viability assay. Treatment volumes were 1.0 μL of 1-10 μM range of stock solutions. Fluorescence was measured with 530 nm excitation wavelength and 590 nm emission wavelength. FIG. 21 represents 3 biological repeats measured in triplicate. DMEM reference blanks were averaged and subtracted from all readings and cellular viability values were calculated as percentage of the 1.0% DMSO vehicle control (VC). Error bars shown as standard error of the mean (SEM) with Student's T-test statistics representing significant p-values referenced between VC and respective treatment; outlier values excluded (n=9) (*p<0.05; p<0.001; *p<0.0001). Significant dose-dependent response/trend is visible as increased drug concentration decreases A375 cellular viability.

Figure 22:
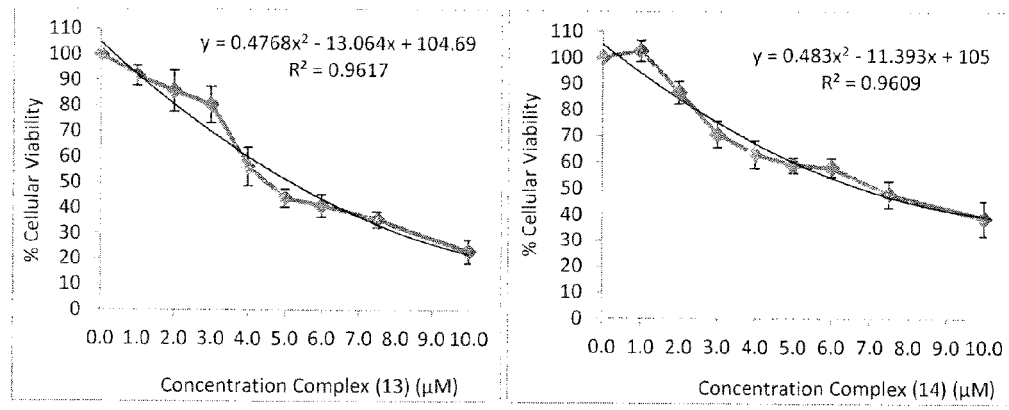
FIG. 22: Polynomial line graph showing percentage cellular viability of A375 malignant melanoma cancer cells treated with a concentration range of complex (13) and complex (14)

FIG. 22 is a polynomial line graph showing percentage cellular viability of 2×10$^5$ A375 malignant melanoma cancer cells/mL treated with a concentration range (1.0 μM-10.0 μM) of complex (13) (left) and complex (14) (right) using the AlamarBlue® cell viability assay. Treatment volumes were 1.0 μL of 1-10 μM range of stock solutions. Fluorescence was measured with 530 nm excitation wavelength and 590 nm emission wavelength. FIG. 22 represents 3 biological repeats measured in triplicate. DMEM reference blanks were averaged and subtracted from all readings and cellular viability values were calculated as percentage of the 1.0% DMSO vehicle control (VC). Error bars shown as standard deviation (STDEV). Significant dose-dependent response/trend is visible as increased drug concentration decreases A375 cellular viability. $IC_{50}$ value was calculated as 5.16 μM+/−0.55 μM for complex (13) and 6.77 μM+/−1.12 μM for complex (14) as determined with 96.0% confidence/reliability, using the quadratic equation formula $$= \frac{-b \pm \sqrt{b^2 - 4a0}}{2a},$$

for both.

The Trypan Blue Exclusion Assay of A375 Malignant Melanoma Cancer

The Trypan blue dye exclusion assay [Sigma. USA] works on the principle that viable cells exclude the diazo dye as their cellular membranes are intact, whereas, dead cells absorb and are stained blue by the dye, therefore, it is a cellular viability indicator. Approximately 10 μL of a cell to Trypan blue reagent (1:1, 10%) mixture was pipetted onto Bio-Rad slide and counted with Bio-Rad Cell Counter [Bio-Rad, USA]. Whole cell number, live/viable cell number and % viability recorded.

Figure 24:
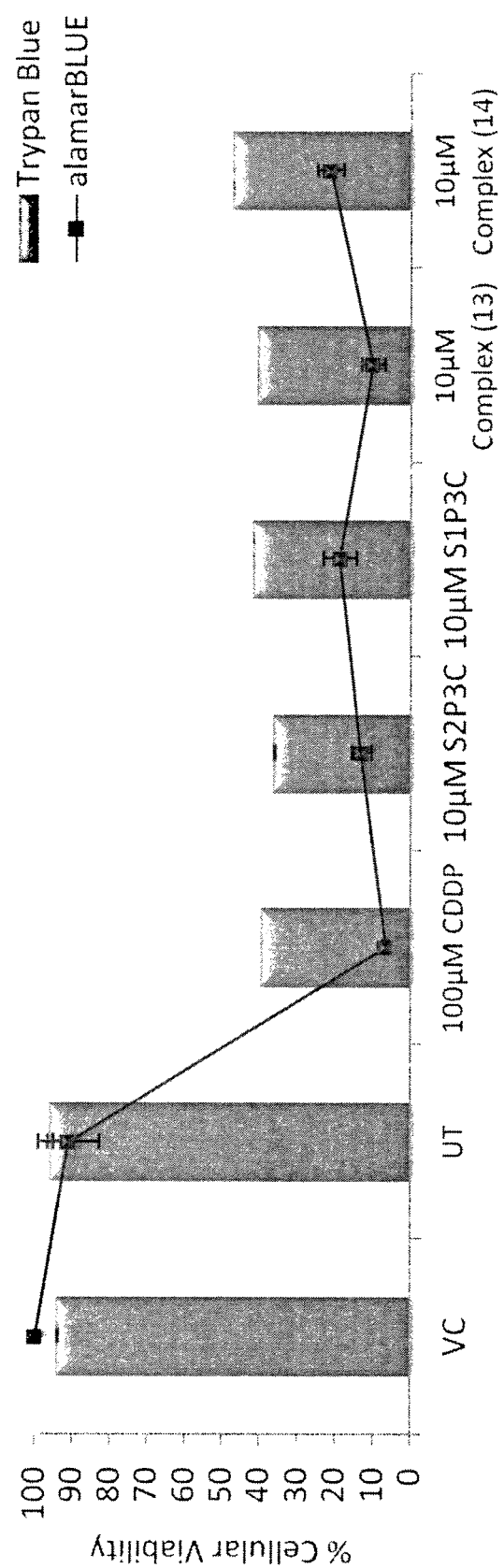
FIG. 24: Bar graph depicting cellular viability analyses of A375 malignant melanoma cancer cells following differential treatments of complex (13) and complex (14)

FIG. 24 depicts cellular viability analyses of A375 malignant melanoma cancer cells after treatments of complex (13) and (14): VC=1.0% DMSO Vehicle Control (VC); UT=Untreated Negative Control; CDDP=100 μM Cisplatin Positive Apoptotic Control and then 10 μM concentrations of silver(I) complexes (13) and (14). Viability determined using AlamarBlue® and Trypan blue viability assays. FIG. 24 represents 3 biological repeats measured in triplicate. DMEM reference blanks were averaged and subtracted from all readings and cellular viability values were calculated as percentage of VC. Error bars shown as standard error of the mean (SEM) for Trypan blue and standard deviation (STDEV) used for AlamarBlue® error bars. Student's T-test statistics represent significant p-values referenced between VC and respective treatment for Trypan blue assay (n=9) (*p<0.05; p<0.001; *p<0.0001). All p-values<0.0001 for AlamarBlue® assay (not shown). A significant decrease in cellular viability is clearly visible in all treatments compared to both VC and UT.

Morphological Features of the Following Differential Treatments as Evaluated by Inverse Light Microscopy Morphological studies were conducted using a Zeiss Axiovert 25 Inverted Light Microscope [Carl Zeiss, Germany] with photographs taken with an Axio Cam Camera and Axio Vision 3.1 software [Carl Zeiss, Germany] at 100× magnification.

Figure 23:
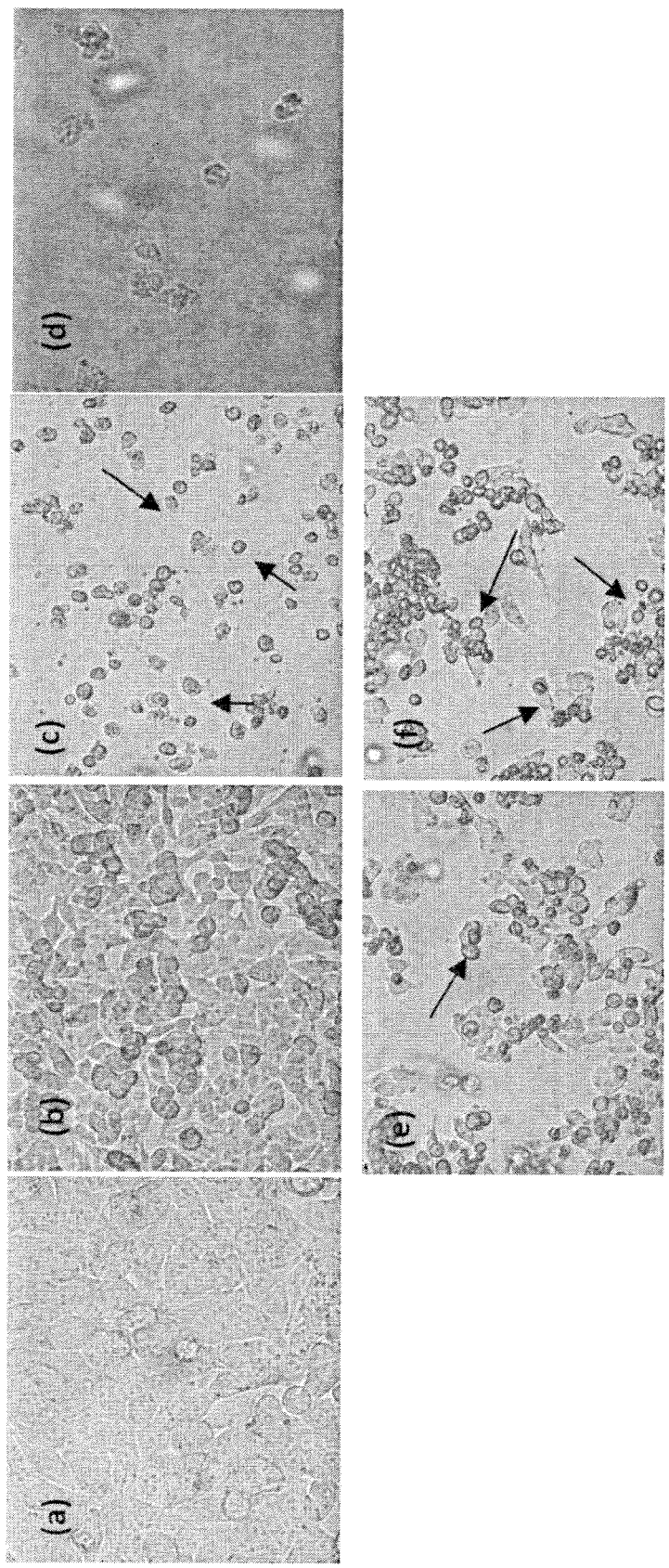
FIG. 23: Morphological analysis of A375 malignant melanoma cancer cells following differential treatments of complex (13) and (14) as evaluated by inverse light microscopy.

Morphological features of A375 malignant melanoma cancer cells evaluated by inverse light microscopy following differential treatments are indicated in FIG. 23: (a)=Untreated Negative Control; (b)=1% DMSO Vehicle Control (VC); (c)=100 μM Cisplatin (CDDP) Positive Apoptotic Control; (d)=Hydrogen Peroxide Positive Necrotic Control; (e)=10 μM complex (13); and (f)=10 μM complex (14). Cells were visualised with Zeiss Axiovert 25 Inverted Light Microscope with photographs taken at 100× magnification. Morphology of A375 cancer cells after differential treatments resembled that of the positive apoptotic control with characteristic apoptotic cellular morphology such as blebbing, rounding and cell shrinkage being observed (indicated by black arrows).

Celltitre-Glo™ luminescent cell viability assay for A375 malignant melanoma cancer cells For purposes of the Celltitre-Glo™ Luminescent Cell Viability [Promega, USA] assay, a 1:1 mixture of cell sample to Celltitre-Glo™ substrate/buffer mix reagent, in duplicate, was added to 96-well black plate, shaken for 30 seconds at room temperature and then further incubated for 30 minutes. Whole luminescence was than measured with a Synergy HT Multi-Detection Microplate Reader. The CytoTox-ONE™ Homogenous Membrane Integrity [Promega, USA] assay is a rapid fluorescent assay that measures the level of lactate dehydrogenase leaked from damaged membranes, therefore, the amount of fluorescence measured is directly proportional to the amount of lysed/damaged cells. In triplicate, a 1:1 cell sample to CytoTox-ONE™ substrate/buffer mix reagent was added to a 96-well clear plate, shaken for 30 seconds followed by incubation for 10 minutes. A CytoTox-ONE™ stop solution was added to each sample followed by a further 30 second shake on an orbital shaker. A positive control consisting of untreated cells lysed with a lysis solution for 1 hour was used, i.e. provided maximum LDH levels. The fluorescence was then measured with a Synergy HT Multi-Detection Microplate Reader at an excitation wavelength of 530 nm and emission wavelength of 590 nm.

Figure 25:
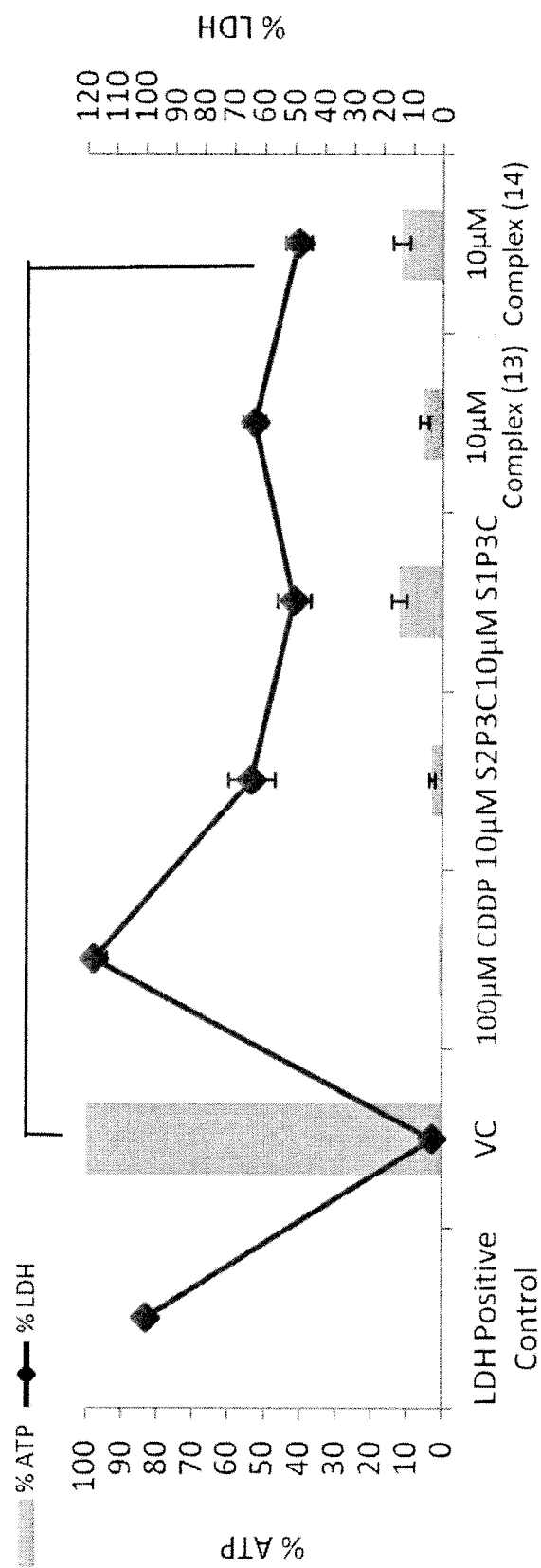
FIG. 25: Graph depicting percentage ATP and Lactate Dehydrogenase (LDH) measured in differentially treated A375 malignant melanoma cancer cells as determined by the Celltitre-Glo™ Luminescent Cell Viability Assay and Cyto-Tox-ONE™ Membrane Integrity Assay respectively.

FIG. 25 depicts the percentage ATP and Lactate Dehydrogenase (LDH) measured in differentially treated A375 malignant melanoma cancer cells as determined by the Celltitre-Glo™ Luminescent Cell Viability Assay and CytoTox-ONE™ Membrane Integrity Assay respectively. ATP levels represented as a percentage of 1.0% DMSO Vehicle Control (VC) at 100%. LDH Levels represented as a percentage of LDH Positive Control (maximum LDH) set at 100%. Cells treated with: CDDP=100 μM Cisplatin Positive Apoptotic Control and then 10 μM concentrations of complex (13) and complex (14). Standard Error of the Mean (SEM) represented as error bars for ATP assay and standard deviation (STDEV) used for LDH error bars. Student's T-test statistics represent significant p-values referenced between VC and respective treatment for ATP assay (n=9) (*p<0.05; p<0.001; *p<0.0001). All p-values<0.0001 for LDH assay (not shown). A significant decrease in cellular ATP levels is noted in all treatments compared to VC and a significant increase in LDH levels is noted compared to the VC.

Apoptopic Pathway Investigation by Means of Caspase 3/7 Assay for A37 malignant Melanoma Cancer Cells Caspase-GLO™ 3/7, 8 and 9 Assays are luminescent assays that measure Caspase activities, which have key effector functions in intrinsic and extrinsic apoptosis, therefore the amount of luminescence measured is proportional to the amount of Caspase activity present. The assays are based on the principle that after Caspase cleavage, a substrate containing the tetrapeptide DEVD sequence binds with Caspase and is released for a luminescent reaction with a thermostable luciferase enzyme. In duplicate, a 1:1 cell sample to Caspase-Glo™ substrate/buffer mix reagent was added into 96-well black plates, then shaken for 30 seconds at room temperature followed by a 1 hour incubation. Whole luminescence was then measured with a Synergy HT Multi-Detection Microplate Reader.

Figure 26:
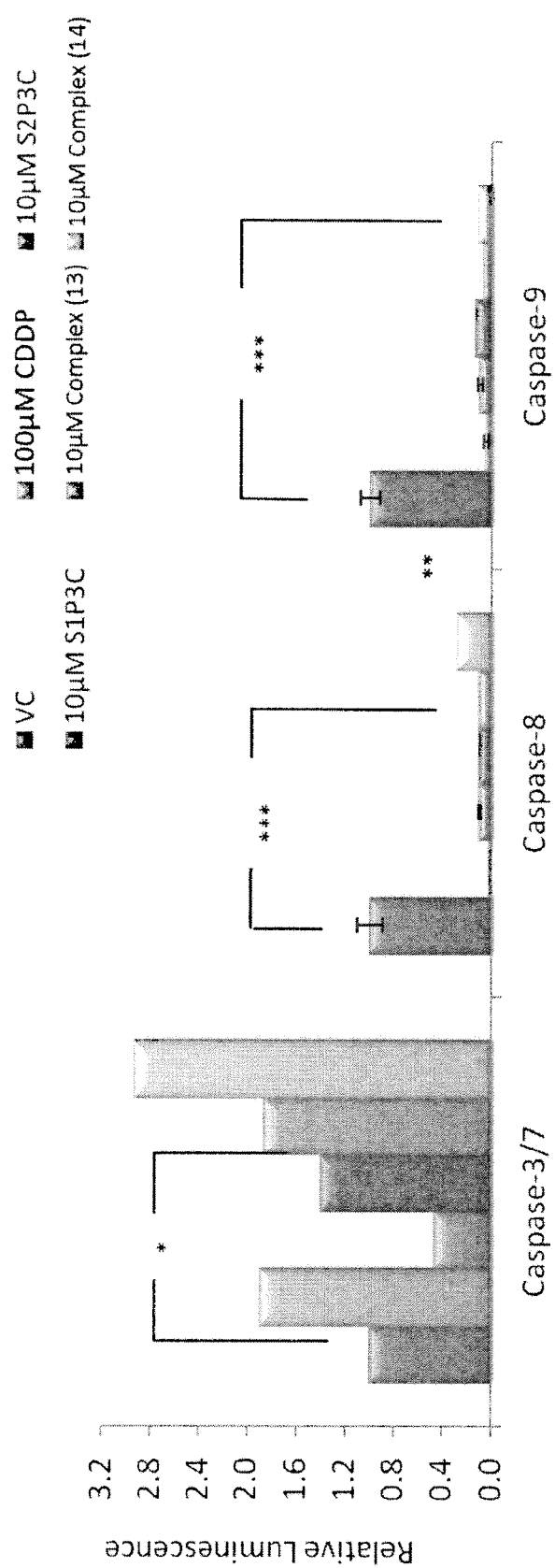
FIG. 26: Graph depicting Caspase 3/7, 8 and 9 levels in differentially treated A375 malignant melanoma cancer cells as determined by relative luminescence recorded using Caspase-GLO™ assays.

FIG. 26 depicts Caspase 3/7, 8 and 9 levels in differentially treated A375 malignant melanoma cancer cells as determined by relative luminescence recorded using Caspase-GLO™ assays. Caspase levels represented as a percentage of 1.0% DMSO Vehicle Control (VC) set at 100%. Cells treated with: CDDP=100 µM Cisplatin Positive Apoptotic Control and than 10 µM concentrations of complex (13) and complex (14). Standard Error of the Mean (SEM) represented as error bars with Student's T-test statistics representing significant p-values referenced between VC and respective treatment for each Caspase assay (n=9) (*p<0.05; p<0.001; *p<0.0001). A significant increase in Caspase 3/7 levels is visible in all treatments, when compared to the VC, indicating apoptosis is occurring, whereas, no conclusions can be drawn from significantly decreased Caspase 8 and 9 levels compared to VC.

Flow Cytometric Analysis of Apoptosis and/or Necrosis for A375 Malignant Melanoma Cancer Cells To determine if either apoptosis or necrosis occurred, the cells were double labelled with Annexin-V FITC and Propidium Iodide (PI) by means of an Annexin-V FITC assay kit (Serotec, UK). This was done according to manufacture's instructions with a few adjustments. The cells ($\pm 3 \times 10^5$ cells/ml) were washed twice with cold phosphate buffered saline (PBS), followed by the addition of 100 µl 1× binding buffer. Two and a half microliters of Annexin-V along with 5 µl PI were added in the dark and was incubated for 15 minutes at room temperature. After incubation, 400 µl 1× binding buffer was added and cells were analysed using the FACSAria flow cytometer (BD Biosciences, San Jose, Calif.) with FACSDiva software (BD Biosciences, San Jose, Calif.) 492 nm (excitation) and 520 nm for Annexin and 488 nm and 575 nm (emission) for Propidium Iodide.

The CBAO77 Innocyte™ Flow Cytometric Cytochrome C Release Kit [Merck, RSA] with anti-cytochrome C primary antibody and anti-IgG FITC secondary antibody was used, as per manufacturer's instructions, to determine the relocalisation of cytochrome C from the mitochondria to the cytoplasm in order to analyze the regulation of apoptotic signalling in cells in all test samples and controls; this assay is based on the selective permeabilisation of the cellular membrane for the release of cytosolic components whilst leaving the mitochondrial membrane intact and a FACSAria™ flow cytometer and FACSDiva™ software was used for the analyses. This assay also indicates whether the intrinsic apoptotic pathway is being activated as cytochrome C is associated with this pathway. A mouse IgG antibody was used as an isotype control.

Statistical Analysis

Data represented were expressed as either the Standard Error of Mean (SEM) for bar charts or as the Standard Deviation (STDEV) for line graphs. At least 3 biological with 3 technical repeats (n=9) were used for all studies. The Student's T-test [Microsoft™ Excel 2010, USA] was used to calculate the significant difference (*p<0.05; p<0.001; p<0.0001) of the treatments with respect to the vehicle control except in the flow cytometric data.

Biological Studies Discussion

Cellular Viability

Cellular viability, i.e. complex (13) and complex (14)-induced toxicity in both controls and differentially treated A375 malignant melanoma cancer cells, was determined by measuring metabolic mitochondrial activity using an AlamarBlue® Cell Viability Assay. All values were normalised and represented as percentages of the 1.0% DMSO Vehicle Control (VC) that was set to 100%. Representative bar graphs in FIG. 21 were constructed to show dose responsive effects of the two silver(I) complexes (13) and (14), whereas, $IC_{50}$ values were determined using the quadratic formula from standard curves produced in FIG. 22. As can be seen in FIG. 21, cellular viability did decrease in a dose dependent manner, i.e. as the concentration of both silver(I) complexes (13) and (14) was increased, A375 malignant melanoma cellular viability decreased. $IC_{50}$ values were calculated using the quadratic formula and calculated to be 5.16 µM+/−0.55 µM for complex (13) and 677 µM+/−1.12 µM for complex (14).

Morphological Analysis

A375 cancer cell morphology, after various treatments, were compared to the untreated negative control as well as to the positive apoptotic and necrotic controls in order to determine if the various treatments were causing cell death and whether apoptosis was occurring. The morphology of the A375 malignant melanoma cancer cells (FIGS. 23 (e) to (h)) resemble that of the apoptotic positive control (FIG. 23 (c)), indicating that these treatments appear to induce apoptosis in the A375 cancer cell line. A few necrotic cells were also visible in each treatment as compared to the necrotic positive control. Characteristic apoptotic blebbing, rounding and cell shrinkage is visible in FIG. 23 as indicated by arrows. The treated cells were clearly dead when compared to the untreated negative control and the vehicle control (showing healthy viable cells) as shown in FIGS. 23 (a) and (b) respectively. The DMSO used to dissolve the complexes does not interfere in assays nor does it cause drastic cell death as indicated, i.e. the vehicle control consisting of 1.0% DMSO resembles that of the untreated control.

Cellular Viability and Cytotoxicity Investigation

Cellular viability, i.e. silver complex-induced toxicity, in both controls and differentially treated A375 malignant melanoma cancer cells, was determined by measuring metabolic mitochondrial activity using the AamarBlue® Cell Viability Assay, membrane integrity Trypan Blue Viability Assay as well as ATP levels being measured using the Celltitre-Glo™ Luminescent Cell Viability Assay. Included is the Cytolox-ONE™ Membrane Integrity LDH Assay as this cytotoxicity assay goes hand in hand with analysing ATP levels.

As can be seen in FIG. 24, a significant decrease in cellular viability was recorded with both viability assays measuring less than 50% viability in all treatments compared to both UC and VC controls.

In FIG. 25, ATP levels, therefore cellular viability, did decrease significantly (less than 20% viable) in A375 cancer cells treated with silver(I) complexes (13) and (14) as indicated by asterisks with statistical significance set to *p-value<0.05 calculated with Student's T-test. This is in line with the decrease in cellular viability indicated in both the AlamarBlue® and Trypan blue viability assays shown in FIG. 24. With the decrease in ATP levels, it is expected that LDH levels would be high in treatments compared to the VC as cellular viability, therefore, membrane integrity is lost. This was seen as shown in FIG. 25, since there is a significant increase in LDH levels compared to the VC with a concomitant decrease in ATP levels, indicating that cellular viability is decreased substantially after A375 cancer cells are treated with complexes (13) and (14) and that these complexes do exhibit significant cytotoxicity in this cancer cell line.

It is difficult to compare these results to those in literature concerning cellular viability and mode of programmed cell death (PCD), in the malignant melanoma cell line, due to the fact that the silver(I)complexes (13) and (14) are under investigation with no reported studies on these compounds being available. With that said, comments can be made on anticancer metal complexes, in general, on biochemical changes observed and recorded in cancer cells. Conventional cytotoxic chemotherapies used, in conjunction with adjuvants such as interferon and interleukin inhibitors, to treat malignant melanomas are alkylating agents dacarbazine (DITC), carmustine, temozolomide as well as Pt-based analogues.

Apoptotic Pathway Investigation

Caspase-GLO™ 3/7, 8 and 9 assays were performed, not only to confirm apoptosis was occurring, but to also deduce whether intrinsic or extrinsic apoptosis was occurring, i.e. these assays were performed to more closely examine the mode of PCD. Caspase 8 plays a key initiator role in the extrinsic apoptotic pathway, whereas Caspase 9 is a key initiator in the intrinsic apoptotic pathway, therefore, measuring their relevant levels in differentially treated A375 cancer cells might shed light as to which apoptotic pathway is occurring. Caspase 3/7 assay is performed to confirm whether apoptosis is occurring as these enzymes play key effector roles in the apoptotic pathway.

It can be clearly seen in FIG. 26, that Caspase 3/7 levels have increased compared to the VC indicating that apoptosis is in fact occurring in A375 cancer cells treated with silver(I) complexes (13) and (14). However, no conclusive deductions can be made from both the Caspase 8 and 9 assays even though their levels are significant compared to the VC; it was expected that either Caspase 8 or 9 or both levels would increase after treatments but this was not detected.

Caspases form the central component of the apoptotic proteolytic system and can be divided into 3 sub groups namely: 1) initiator Caspases such as 8 and 9 that are initiators of the extrinsic and intrinsic apoptotic pathways respectively, 2) apoptotic executioners such as Caspases 3 and 7 and 3) and Caspases that participate in cytokine maturation such as Caspases 1 and 4 (Lin et al., 2000; Rao et al., 2002). Therefore, it could be deduced that 24 hour treatments might be too long a time for Caspase 8 and 9 detection, i.e. apoptosis is already in its late stages as indicated by the increased levels of Caspase 3/7. Caspase 3/7 enzymes are involved later in the apoptotic pathway, therefore it makes sense that these enzyme levels are increased in A375 cancer cells. Intracellular substrates are cleaved by effector Caspases like 3 and 7, resulting in cell death and the typical morphological and biochemical features of apoptosis as seen in FIG. 23 through to FIG. 26.

Example E

Various Ratios of Silver(I) Nitrate Triphenylphosphine Complex Prepared According to Example B and the Toxicity Evaluation Thereof on Fibroblast Cells and A-549 Lung Cancer Cells 1. General The silver(I) nitrate triphenylphosphine complexes under investigation in this study were synthesized according to the procedure set forth in Example B (complexes (6)-(9)). For purposes of this study, the toxicity evaluation of various molar ratios of silver(I) nitrate salt:phosphine ligand on fibroblast cells and A-549 lung cancer cells was assessed.

For the biological studies, fibroblasts (Sigma-Aldrich) were maintained with FM (ScienCell Research Laboratories). Lung cancer (A-549) cells were obtained from the University of Pretoria, RSA.

2. Cell Culturing and Treatment

A-549 lung cancer cells were maintained in DMEM supplemented with 10% fetal calf serum (FCS), 1 mM pyruvate, 2 mM L-glutamine (Highveld Biological, Kelvin, RSA), 1% antibiotics (penicillin, streptomycin, amphotericin (Highveld Biological, Kelvin, RSA) and gentamycin (Invitrogen Life Technologies, Eugene, Oreg.)).

Cells ($1\times10^4$ cells/well) were plated in 96-well flat-bottomed plates and incubated for 24 h at 37° C. with 5% $CO_2$. All compounds were preheated for 30 min prior treatment. After 24 h compounds (2.5 µM) were mixed with supplemented media and incubated for 24 h. For the untreated control supplemented media was used. Since all compounds were dissolved in DMSO, a 1% DMSO was used as a vehicle control.

Several assays were used to evaluate the effect of complexes (6)-(9) (whereby molar ratios of 1:1, 1:2, 1:3 and 1:4 were evaluated) on cell death with respect to the fibroblast cells and A-549 lung cancer cells. These included cell viability assays such as the AlamarBlue® viability and proliferation assay and microscopy to evaluate cell morphology.

3. Cell Viability and Morphological Studies 3.1 A-549 Lung Cancer Cell Assays

The AlamarBlue® Viability and Proliferation Assay of A-549 Lung Cancer Cells

The A-549 lung cancer cells were incubated at 37° C. for 3 h in the presence of 10% AlamarBlue® viability and proliferation assay (Invitrogen Life Technologies, Eugene, Oreg.). This was performed on the untreated and treated cells to determine viability. Fluorescence was measured at 530-560 nm (excitation) and 590 nm (emission).

Figure 27:
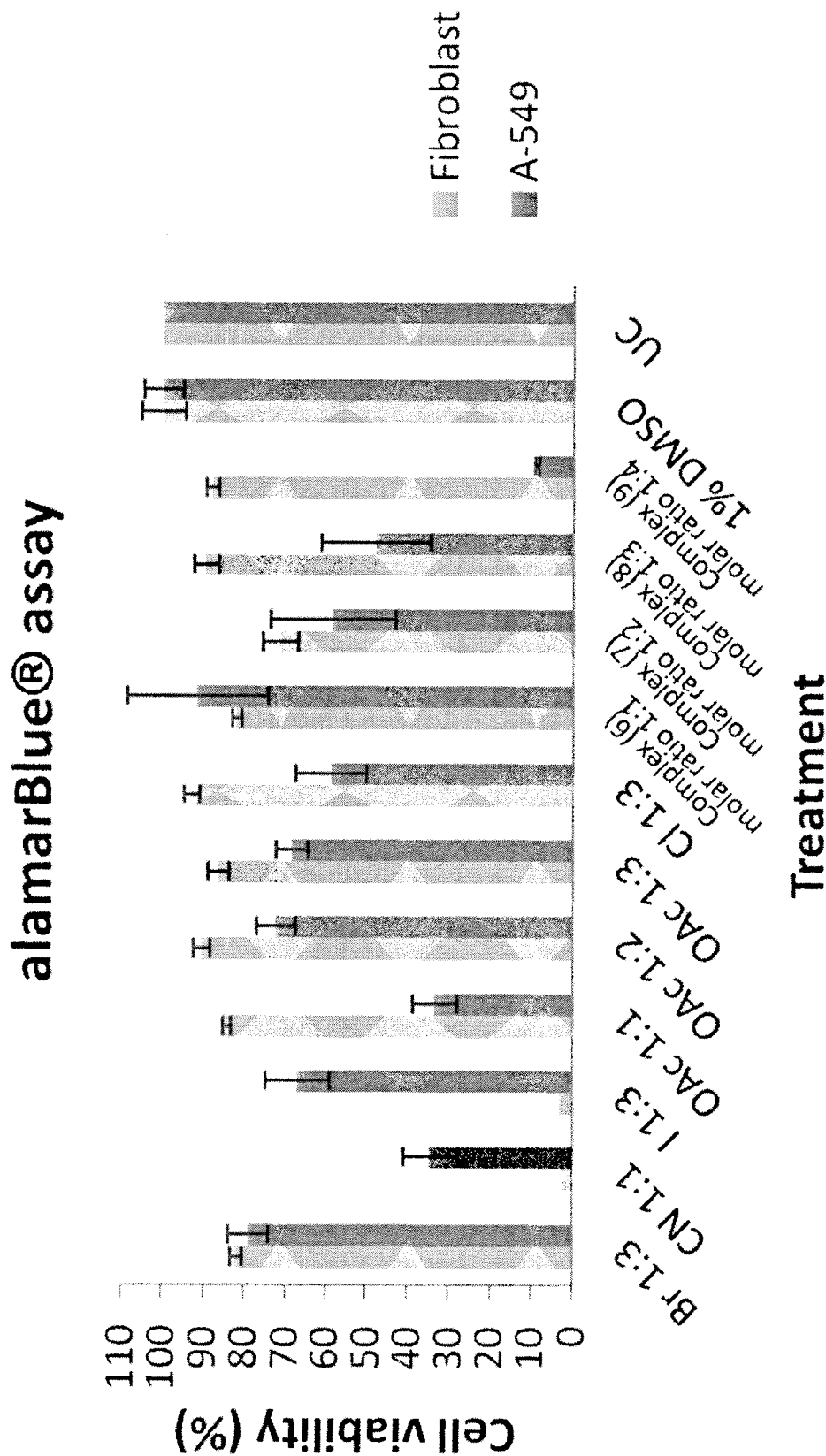
FIG. 27: Bar graph depicting cellular viability analyses of fibroblast cells and A-549 lung cancer cells following differential molar ratios of silver(I) nitrate salt:phosphine ligand (complexes (6)-(9))

FIG. 27 is a bar chart showing percentage cellular viability of fibroblast cells and A-549 lung cancer cells treated with various molar ratios (complexes (6)-(9)) using the AlamarBlue® cell viability assay whereby the molar ratio of the silver(I) nitrate salt:phosphine ligand of 1:1, 1:2, 1:3 and 1:4 was assessed. Fluorescence was measured with 530 nm excitation wavelength and 590 nm emission wavelength. Cellular viability values were calculated as percentage of the 1.0% DMSO vehicle control (VC) and the untreated control (UC). Error bars shown as standard error of the mean (SEM) with Student's T-test statistics representing significant p-values.

Morphological Features of the A-549 Lung Cancer Cells Following Differential Treatments as Evaluated by Inverse Light Microscopy Morphological studies were conducted using a Zeiss Axiovert 25 Inverted Light Microscope [Carl Zeiss, Germany] with photographs taken with an Axio Cam Camera and Axio Vision 3.1 software [Carl Zeiss, Germany] at 100× magnification.

Figure 28:
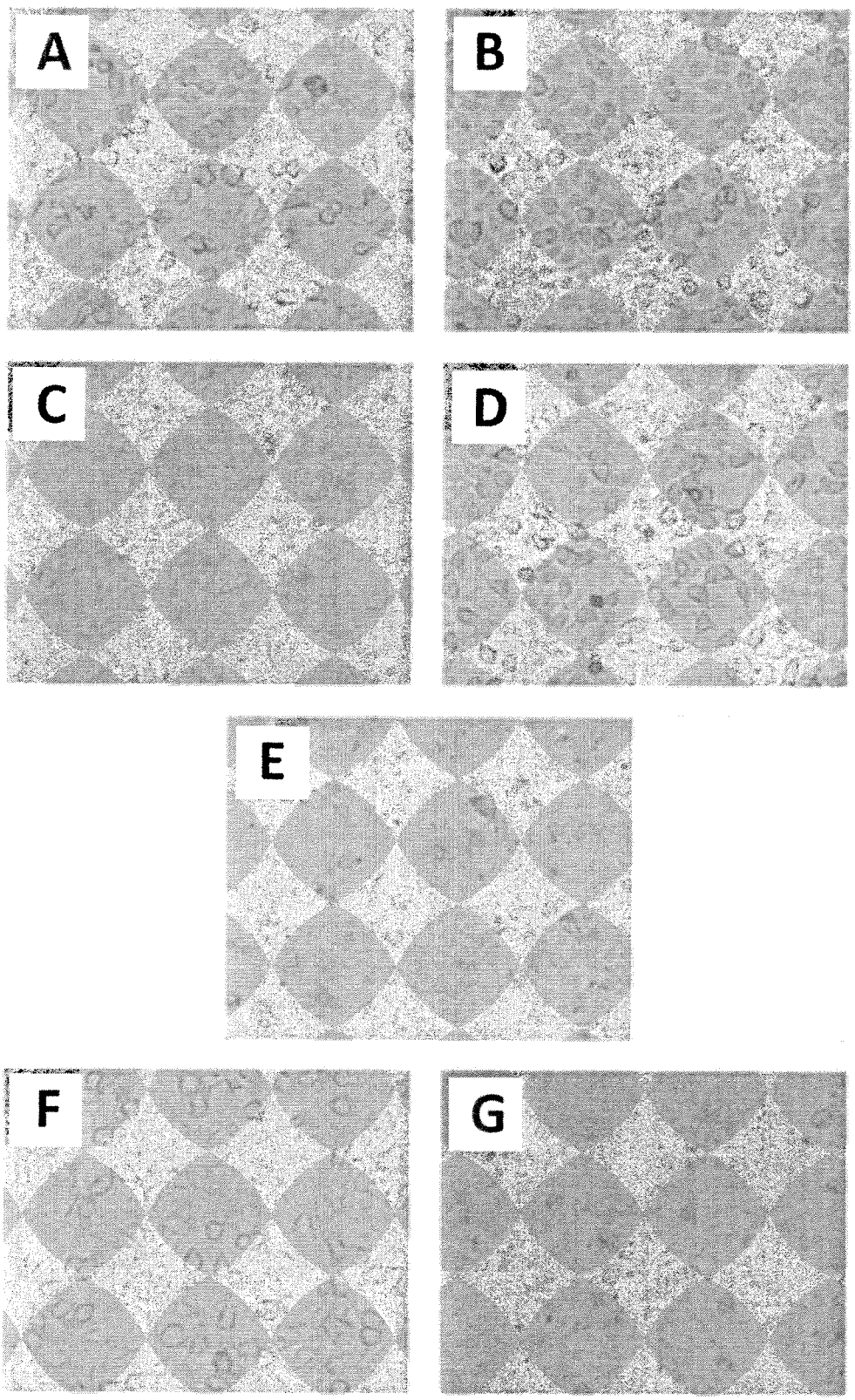
FIG. 28: Morphological analysis of A-549 lung cancer cells following differential molar ratios of silver(I) nitrate salt:phosphine ligand (complexes (6)-(9)) as evaluated by inverse light microscopy.

Morphological features of A-549 lung cancer cells evaluated by inverse light microscopy following differential treatments are indicated in FIG. 28: (A)=Untreated Negative Control; (B)=1% DMSO Vehicle Control (VC); (C)=100 µM Cisplatin (CDDP) Positive Apoptotic Control; (D)=Hydrogen Peroxide Positive Necrotic Control; (E)=complex (6) having a molar ratio of 1:1; (F)=Triphenylphosphine Ligand; (G)=complex (9) having a molar ratio of 1:4. Cells were visualised with Zeiss Axiovert 25 Inverted Light Microscope with photographs taken at 100× magnification. Morphology of A-549 lung cancer cells after differential treatments resembled that of the positive apoptotic control with characteristic apoptotic cellular morphology such as blebbing, rounding and cell shrinkage being observed.

FIG. 28 (C)-(G) showed signs of apoptosis although complex (9) having a 1:4 molar ratio was the more effective. The untreated and vehicle control showed no cell death.

Biological Studies Discussion
Cellular Viability

Silver(I) nitrate triphenylphosphine adducts were prepared with silver(I) nitrate to phosphine ligand molar ratios of 1:1 to 1:4 (complexes (6)-(9)) and used to treat A-549 lung cancer cells. All 1:1, 1:2, 1:3 and 1:4 molar ratios were found to be toxic to the A-549 lung cancer cells however the 1:4 molar ratio (complex (9)) was observed to have a higher toxicity level in relation to the other ratios. Morphological studies, combined with AlamarBlue® cell viability assay confirmed that ratios of 1:1, 1:2, 1:3 and 1:4 (complexes (6)-(9)) resulted in apoptosis of the A-549 lung cancer cells.

Final Conclusion

Metal-based drugs have important roles in cancer chemotherapy. The platinum based drugs Cisplatin and carboplatin have a wide range of applications in cancer chemotherapy and other metals such as gold(I) and silver(I) are known to possess anti-tumour activity. The interplay of parameters such as the geometrical flexibility of silver(I), bite angle, electronic properties of the phosphine ligand and the coordination mode of the supporting ligands consequently make the study of silver(I) chemistry very attractive. The Applicant has prepared silver(I) monophosphine complexes having anticancer properties for selectively inhibiting the activity of cancer cells. These results indicate that the silver(I) complexes of the present invention may represent the first, promising step in the designing of target-specific chemotherapeutic drugs. Further studies to investigate the mode of apoptotic cell death of these complexes, validated by the data presented herein.

REFERENCES

Baguley, B. C.; Berners-Price, S. J.; Bowen. R. J.; Farr, A.; Galettis, P.; Liu, J. J.; Maharaj, L.; McGechan, A. C.; McKeage, M. J.; Samarasinha, H.; (2008) In vitro anti-tumor and hepatotoxicity profiles of Au(I) and Ag(I) bidentate pyridyl phosphine complexes and relationships to cellular uptake. Journal of Inorganic Biochemistry 102: 303-310.

Barnard, P. J.; Berners-Price, S. J.; (2007) Targeting the mitochondrial cell death pathway with gold compounds. Co-ordination Chemistry Reviews 251 (13-14): 1889-1902.

Bayir, H.; Kagan. V. E.; (2008) Bench-to-bedside review: Mitochondrial injury, oxidative stress and apoptosis—there is nothing more practical than a good theory. Critical Care 12: 206

Bello, B. O.; Fadahun, et al. (2011). "Trends in lung cancer mortality in South Africa: 1995-2006." BMC Public Health 11(1): 209

Berners-Price, S. J.; and Sadler P. J.; (1988) Structure and bonding. Phosphine and metal phosphine complexes: Relationship of chemistry to anticancer and other biological activity. Bioinorganic Chemistry, Springer Berlin/Heidelberg, 70 p 27-102

Berners-Price, S. J.; Bowen, R. J.; Galettis, P.; Healy, P. C.; McKeage, M. C.; (1999) Structural and solution chemistry of gold(I) and silver(I) complexes of bidentate pyridyl phosphines: selective antitumour agents: Coordination Chemistry Reviews 185-186, 823-836

Berners-Price, S. J.; Bowen, R. J.; Harvey, P. J.; Healy, P. C.; Koutsantonis, G. A.; (1998) J. Chem. Soc., Dalton Transactions (11): 1743-1750

Bird-Lieberman, E. L.; Fitzgerald R. C.; (2009) Early diagnosis of oesophageal cancer. British Journal of Cancer 101: 1-6

Bold, R. J.; Termuhlen, P. M.; McConkey, D. J; (1997) Apoptosis, cancer and cancer therapy. Surgical Oncology 6; 133-142

Brandys, M. C.; Puddephatt R. J.; (2002), Polymeric complexes of silver(I) with diphosphine ligands: self-assembly of a puckered sheet network structure. Journal of the American Chemical Society 124(15): 3946-3950.

Bressac-de-Paillerets, B.; Avril, M. F.; Chompret, A.; Demenais, F; (2002) *Genetic and environmental factors in cutaneous malignant melanoma.* Biochimie 84(1): 67-74

Cancer Facts & Figures; (2007). Atlanta, Ga.: American Cancer Society.

Chabner, B. A.; Roberts T. G.; (2005) Chemotherapy and the war on cancer. Nature Reviews 5: 65-72

Chowdhury, I.; Tharakan, B.; Bhat, G. K.; (2008) Caspases—an update. Comparative Biochemistry and Physiology. Part B. 151: 10-27

Cotter, T. G.; (2009) Apoptosis and cancer: the genesis of a research field, Nature Reviews Cancer 9(7): 501-507

Dania, N. N.; Korsmeyer, S. J.; (2004) Cell death: critical control points. Cell 116: 205-219

Elmore, S.; (2007) Apoptosis: A Review of Programmed Cell Death: Toxicological Pathology 35: 495-516

Enzinger, P. C.; Mayer R. J.; (2003) Esophageal Cancer. National English Journal of Medicine, 349: 2241-52

Ferlay, J.; Shin H. R.; Bray F.; Forman D.; Mather s C.; and Parkin, D. M.; Globocan (2008) v1.2, Cancer Incidence and Mortality Worldwide: IARC CancerBase No. 10 [Internet]. Lyon, France: International Agency for Research on Cancer; 2010. Available from: http://globocan.iarc.fr, accessed on 18 Apr. 2012. Cancer Incidence and Mortality Worldwide Ferlay, J.; Shin, et al; (2010). "Estimates of worldwide burden of cancer in 2008: GLOBOCAN 2008". International Journal of Cancer 127(12): 2893-2917

Festjens, N.; Vanden Berghe, T.; Vandenabeele, P.; (2006) Necrosis, a well-orchestrated form of cell demise: Signalling cascades, important mediators and concomitant immune response. Biochimica et Biophysica Acta. 1757: 1371-1387

Fischer, S. J.; Benson, L. M.; Fauq, A.; Naylor, S.; Winderbank, A. J.; (2008) Cisplatin and dimethyl sulfoxide react to form an adducted compound with reduced cytotoxicity and neurotoxicity: Neurotoxicology 29: 444-452

Fischer, U.; Schulze-Osthoff K.; (2005) Apoptosis-based therapies and drug targets, Cell Death and Differentiation 12: 942-961.

Garbe, C.; Peris, K.; Hauschild A.; Salag, P.; Middleton, M.; Spatz, A.; Grob, J. J.; Malvehy, J.; Newton-Bishop, J.; Stratigos, A.; Pehamberger, H.; Eggermont, A.; (2010) Diagnosis and treatment of melanoma: Europeanconsensus-based interdisciplinary guideline. European Journal of Cancer 46: 270-283.

Garcia, M.; Jemal A.; Ward E. M.; Center M. M.; Hao Y.; Siegel R. L.; and Thun M. J.; (2007) Global Cancer Facts & Figures 2007. Atlanta, Ga.: American Cancer Association.

Giblin, A. V.; Thomas, J. J.; (2007) Incidence, morality and survival in cutaneous melanoma. Journal of Plastic, Reconstructive and Aesthetic Surgery 60(1): 32-40.

Golstein, P.; Kroemer, G.; (2007) Cell death by necrosis: Towards a molecular definition. Trends in Biochemical Sciences 32: 37-43

Hanahan, D.; Weinburg R. A.; (2000) The hallmarks of cancer, Cell 100: 57-70

Holdenrieder, S.; Stieber, P.; (2004) Apoptotic markers in cancer. Clinical Biochemistry 37: 605617

Jimenez Del Rio, M.; and Velez-Pardo, C.; (2004) Transition metal induced apoptosis in lymphocytes via hydroxyl radical generation, mitochondria dysfunction and caspase-3 activation: an in vitro model for neurodegeneration. Medical Research 35(3): 185-193

Kerr, J. F. R.; Wyllie A. H.; Currie A. R.; (1972) Apoptosis: a basic biological phenomenon with wide-ranging implication in tissue kinetics. British Journal of Cancer 26: 239-257

Kerr, J. F. R.; (1994) Apoptosis: Its significance in cancer and cancer therapy. Cancer 73 (8): 2013-2022

Khumalo, N. M.; Meijboom, R.; Muller, A.; Omondi, B.; (2010) Acta Cryst., E66, m451

King, K. L.; Cidlowski, J. A.; (1998) Cell cycle regulation and apoptosis. Annual Review of Physiology 60: 601-617

Kroemer, G.; Galuzzi, L.; Brenner, C.; (2007) Mitochondrial membrane permeabilization in cell death. Physiological Reviews 87: 99-163

Kroemer, G.; Galluzzi L.; Vandenabeele P.; Abrams J.; Alnemri E. S.; Baehrecke E. H.; Blagosklonny M. V.; El-Deiry W. S.; Golstein P.; Green D. R.; Hengartner M.; Knight R. A.; Kumar S.; Lipton S. A.; Malorni W.; Nunez G.; Peter M. E.; Tschopp J.; Yuan J.; Piacentini M.; Zhivotovsky B.; and Melino G.; (2009) Classification of cell death: recommendations of the Nomenclature Committee on Cell Death 2009. Cell Death and Differentiation 16: 3-11

Lin, A. W.; Lowe, S. W.; (2000), Apoptosis in cancer. Carcinogenesis 21: 485-495.

Liu, J. J.; Galettis, P.; Farr, A.; Maharaj, L.; Samarasinha, H.; McGechan, A. C.; Baguley, B. C.; Bowen, R. J.; Berners-Price, S. J.; McKeage, M. J.; (2008) In vitro antitumour and hepatotoxicity profiles of Au(I) and Ag(1) bidentate pyridyl phosphine complexes and relationships to cellular uptake. Journal of Inorganic Biochemistry 102(2): 303-310

Lowe, S. W.; Cepero, E.; Evan, G.; (2004) Intrinsic tumour suppression. Nature 432: 307-315

Mann, F. G.; Wells, A. F.; Purdue, D.; (1937) J. Chem. Soc. 1828.

McCabe, M. L.; Dlamini, Z.; (2005) The molecular mechanisms of oesophageal cancer. International Pharmacology 5: 1113-1130

Meijboom, R.; Bowen, R. J.; Berners-Price, S. J.; (2009) Coordination complexes of silver(I) with tertiary phosphine and related ligands. Coord. Chem. Rev., 253, 325-342

Mizushima, N.; (2004) Methods for monitoring autophagy. The International Journal of Biochemistry & Cell Biology 36: 2491-2502

Nguyen, J. T.; Wells J. A.; (2003) Direct activation of the apoptosis machinery as a mechanism to target cancer cells. Proceedings of the National Academy of Sciences 100: 7533-7538

Omondi, B.; Meijboom, R.; (2010) Acta Cryst., B66, 69. A third polymorph has also been observed. R. Meijboom, Omondi, unpublished results.

Piao, M. J.; Kim, K.; Choi, J.; Choi, J.; Won Hyun, J.; (2010) Silver nanoparticles down-regulate Nrf2-mediated 8-oxoguanine DNA glycosylase 1 through inactivation of extracellular regulated kinase and protein kinase B in human Chang liver cells. Toxicology Letters 207:143-148

Piao, M. J.; Ah Kang, K.; Lee, I. K.; Kim, H. S.; Kim, S.; Choi, J-Y et al; (2011) Silver nanoparticles induce oxidative cell damage in human liver cells through inhibition of reduced glutathione and induction of mitochondria-involved apoptosis: Toxicology Letters 201: 92-100

Pitot, H. C.; (2002) Fundamentals of Oncology. 4th Ed Marcel Dekker Inc, NY USA, pp 27. 901

Rackham, D.; Nichols, S. J.; Leedman, P. J.; Berners-Price, S. J.; Filipovska, A.; (2007) Gold(I) phosphine complex selectivity induces apoptosis in breast cancer cells: Implication for Anti-cancer therapeutics targeted to mitochondria. Biochemical Pharmacology 74: 992-1002

Reed. J. C.; (1999) Dysregulation of apoptosis in cancer, Journal of Clinical Oncology 17: 2941-2953

Reedijk, J.; (2003) New clues for platinum antitumor chemistry: Kinetically controlled metal binding to DNA, Proceedings of the National Academy of Sciences (100) 7: 3611-3616

Sadler, P. J.; and Guo, Z.; (1998) Metal complexes in medicine: Design and mechanism of action. Pure and Applied Chemistry 70 4 863-875

Sawamura, M.; Hamashima, H.; Ito, Y.; (1990) The asymmetric aldol reaction of tosylmethyl isocyanide and aldehydes catalyzed by chiral silver(I) complexes. Journal of Organic Chemistry. 55(24), 5935-5936

Scherer, D.; Kumar R.; (2010) Genetics of pigmentation in skin cancer—A review. Mutation Research 705: 141-153

Segapelo, T. V.; Gozei, I. A.; Spencer, L. C.; Van Zyl, W. E.; (2009) (Pyrazolylmethyl) Pyridine platinum (II) and gold (III) complexes: synthesis structures and evaluation as anticancer agents. Inorganica Chemica Acta 362: 3316-3324

Simstein, R.; Burow, M.; Parker, A.; Weldon, C.; Beckman, B.; (2003) Apoptosis, chemoresistance and breast cancer: Insights from the MCF-7 cell model system. Experimental Biology and Medicine 228: 995-1003

Teodoro, J. S.; Simoes A. M.; Duarte, F. V.; Rolo, A. P.; Murdoch, R. C.; Hyussain, S. M.; Palmeira, C. M.; (2011) Assessment of the toxicity of silver nanoparticles in vitro: A mitochondrial perspective. Toxicology in vitro 25664-670

Venter, G. J. S.; Meijboom, R.; Roodt, A.; (2007) Acta Cryst., E63, m3076

Vogelstein, B.; Kinzler, K. W.; (2004) Cancer genes and the pathways they control, Nature Medicine 10 (8): 789-799

Vorobiof, D. A.; Sitas, F.; Vorobiof, G.; (2001) Breast cancer incidence in South Africa. Journal of Clinical Oncology 19: 125s-127s Wang, Z.-B.; Liu, Y.-Q.; Cui, Y.-F.; (2005) Pathways to caspase activation. Cell Biology International 29: 489-496

Zartilas, S.; Hadjikalas et al. (2009) Tetrameric 1:1 and monomeric 1:3 complexes of silver (I) halides with tri 9p-tolyl) phosphine: a structural and biological study. Inorganica Chemica Acta 362:1003-1010

Zhang, A.; Wu, Y.; Lai, H. W. L.; Yew, D. T.; (2004) Apoptosis A Brief Review. Neuroembryology 5 (3): 47

Zhivotovsky, B.; Kroemer G.; (2004) Apoptosis and genomic instability. Nature Reviews Molecular Cell Biology 5: 752-762

Zimmermann, K. C.; Bonzon C.; Green D. R.; (2001) The machinery of programmed cell death. Pharmacology and Therapeutics 92: 57-70

Zong, W.-X.; Thompson, C. B.; (2006) Necrotic death as a cell fate. Genes and Development 20:1-15

The invention claimed is:

1. A pharmaceutical composition comprising Complex (5), represented by the following formula:

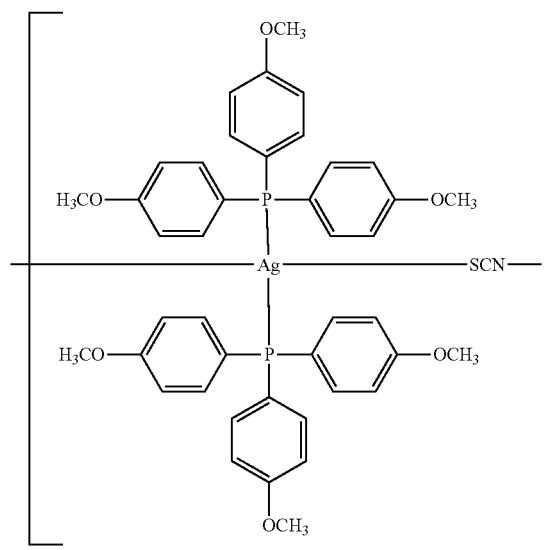

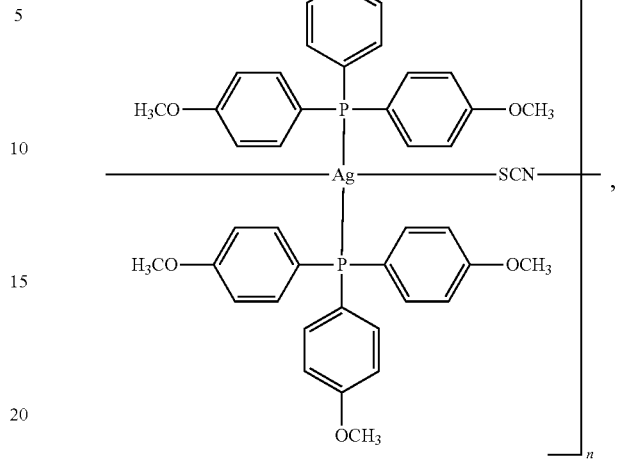

or a pharmaceutically acceptable salt or polymorph thereof; wherein n is an integer from 1 to 100.

2. The pharmaceutical composition of claim 1, wherein the pharmaceutical composition comprises one or more of a pharmaceutically acceptable excipient, additive or carrier.

3. A method for manufacturing the pharmaceutical composition according to claim 1, comprising combining Complex (5) with one or more pharmaceutically acceptable excipients, additives or carriers.

4. A method for treating or diagnosing cancer, comprising administering to a patient suffering from cancer an effective amount of Complex (5), represented by the following formula:

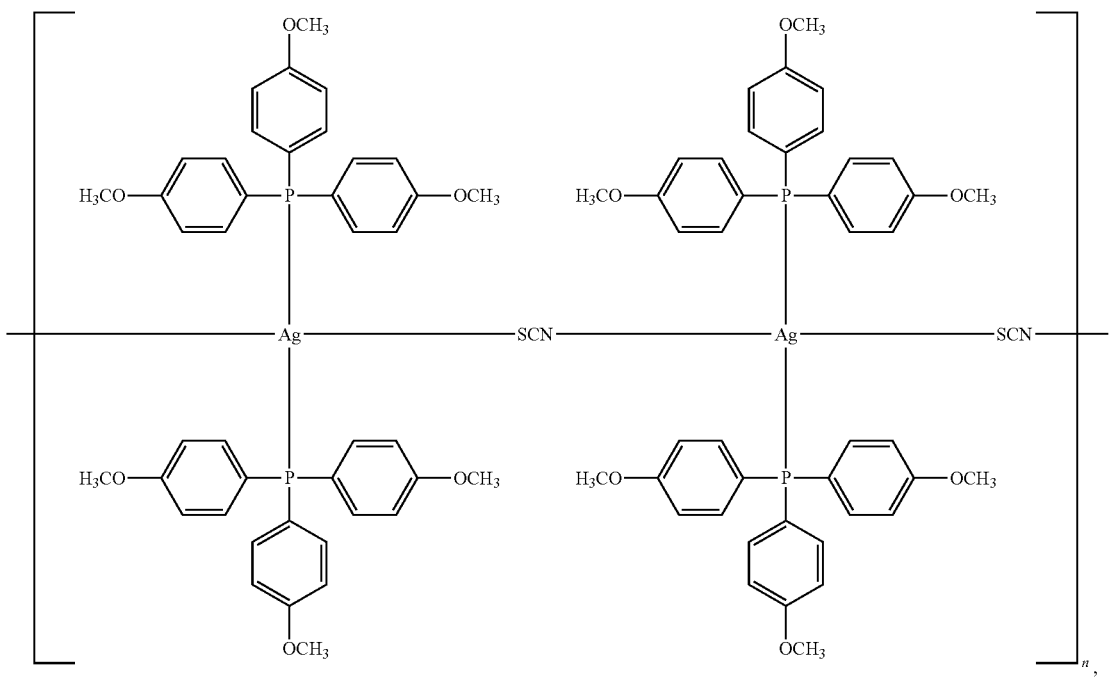

a pharmaceutically acceptable salt, or polymorph thereof; wherein n is an integer from 1 to 100.

5. The method according to claim 4, wherein the treating comprises selectively inhibiting the activity of cancer cells.

6. The method according to claim 4, wherein the cancer is selected from the group consisting of breast cancer, esophageal cancer, lung cancer, colon cancer, ovarian cancer, leukemia, renal cancer, melanoma cancer, prostate cancer, CNS cancer, carcinoma, lymphoma, blastoma, sarcoma, leukemia, gastric or stomach cancer, gastrointestinal cancer, pancreatic cancer, glioblastoma, cervical cancer, ovarian cancer, liver cancer, bladder cancer, cancer of the urinary tract, hepatoma, rectal cancer, colorectal cancer, endometrial or uterine carcinoma, salivary gland carcinoma, vulval cancer, thyroid cancer, hepatic carcinoma, anal carcinoma, and penile carcinoma.

7. The method according to claim 4, wherein the treating comprises inhibiting metastasis of cancer.

8. The method according to claim 4, wherein the treating comprises reducing cell growth of cancer.

* * * * *